(12) United States Patent
Yu et al.

(10) Patent No.: US 6,316,438 B1
(45) Date of Patent: Nov. 13, 2001

(54) FUSED PYRIDOPYRIDAZINE INHIBITORS OF CGMP PHOSPHODIESTERASE

(75) Inventors: Guixue Yu, West Windsor; John Macor, Flemington; Soojin Kim, West Orange; Hyei-Jha Chung, Plainsboro; Michael Humora, Cranbury; Kishta Katipally, East Brunswick; Yizhe Wang, Monmouth Junction, all of NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/526,162

(22) Filed: Mar. 15, 2000

Related U.S. Application Data

(60) Provisional application No. 60/148,009, filed on Aug. 10, 1999, and provisional application No. 60/125,488, filed on Mar. 22, 1999.

(51) Int. Cl.[7] ............... C07D 237/26; C07D 413/04; C07D 243/08; A61K 31/495; A61K 31/535

(52) U.S. Cl. .............. 514/212.08; 544/234; 544/115; 514/248; 514/232.8; 514/218; 514/217.05; 540/599; 540/575; 540/524

(58) Field of Search .................................. 544/234, 115; 514/248, 232.8, 217.05, 218, 212.08; 540/599, 575, 524

(56) References Cited

U.S. PATENT DOCUMENTS

| | | | |
|---|---|---|---|
| 3,669,950 | 6/1972 | Hoehn et al. | 260/295.5 |
| 3,787,430 | 1/1974 | Hoehn et al. | 260/296 H |
| 4,072,681 | 2/1978 | Denzel et al. | 260/256.4 |
| 5,250,534 | 10/1993 | Bell et al. | 514/258 |
| 5,874,437 | 2/1999 | Garvey et al. | 514/258 |
| 6,087,368 | 7/2000 | Macor et al. | 514/267 |

FOREIGN PATENT DOCUMENTS

| | | |
|---|---|---|
| 491477 | 6/1992 | (EP) . |
| 702555B | 3/1998 | (EP) . |
| 6-281581 | * 1/1994 | (JP) . |
| WO 98/56785 | 12/1998 | (WO) . |
| WO98/56785 | 12/1998 | (WO) . |
| 98/56785 | * 12/1998 | (WO) . |
| WO00/15222 | 3/2000 | (WO) . |

OTHER PUBLICATIONS

Bowman et al., Br. J. Pharmac. (1984) 81, 665–674.
Bos et al., J. Med. Chem., 40, 2762–2769 (1997).
Rajfer et al., New England Jour. of Med., Jan. 9, 1992, 90–94.
Trigo-Rocha et al., Am. Journ or Physiol, 1993, vol. 264, H419–H422.
Martel et al., Drugs of the Future, 1997, vol. 22, p. 138–143.

* cited by examiner

*Primary Examiner*—Mukund J. Shah
*Assistant Examiner*—Hong Liu
(74) *Attorney, Agent, or Firm*—Stephen B. Davis

(57) ABSTRACT

Compounds of the formula (I)

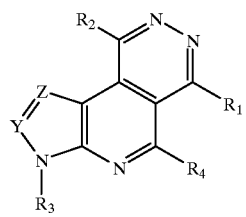

are useful as inhibitors of cGMP PDE especially Type 5.

20 Claims, No Drawings

FUSED PYRIDOPYRIDAZINE INHIBITORS OF CGMP PHOSPHODIESTERASE

This application claims priority from Ser. Nos. 60/125,488 filed Mar. 22, 1999 and 60/148,009 filed Aug. 10, 1999.

FIELD OF THE INVENTION

The present invention relates to fused pyridopyridazine compounds, to methods of using such compounds in the treatment of cGMP-associated conditions such as sexual dysfunction including erectile dysfunction and female sexual arousal disorder, to pharmaceutical compositions containing such compounds, and to intermediates for and methods of preparing such compounds.

BACKGROUND OF THE INVENTION

Erectile dysfunction is the inability to obtain and maintain a penile erection sufficient for sexual intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of certain medicaments including some types of antihypertensive agents, digoxin, as well as the excessive use of narcotics, alcohol, tobacco, etc. Methods for the treatment of erectile dysfunction include the use of vacuum devices and penile implants, as well as the administration of medicaments such as yohimbine, papaverine and apomorphine. Improved methods for the treatment of this disorder are sought, however, as the aforementioned methods do not provide sufficient efficacy, and/or are accompanied by drawbacks or side effects such as erosion, pain, priapism or gastrointestinal discomfort.

As penile erection is dependent upon the presence of adequate levels of cyclic guanosine 3',5'-monophosphate (cGMP), especially in corpora cavernosa tissue, administration of an inhibitor of a cGMP phosphodiesterase (cGMP PDE) particularly, a selective inhibitor of cGMP PDE Type 5 (cGMP PDE 5), provides a means for achieving and maintaining an erection, and therefore for treating erectile dysfunction. See Trigo-Rocha et al., "Nitric Oxide and cGMP: mediators of pelvic nerve-stimulated erection in dogs," *Am. J. Physiol.*, Vol. 264 (February 1993); Bowman et al., "Cyclic GMP mediates neurogenic relaxation in the bovine retractor penis muscle," *Br. J. Pharmac.*, 81, 665–674 (1984); and Rajfer et al., "Nitric Oxide as a Mediator of Relaxation of the Corpus Cavernosum in Response to Nonadrenergic, Noncholinergic Neurotransmission," *New England J. Med.*, 326, 2, 90–94 (January 1992). Sildenafil, for example, has been described as a phosphodiesterase Type V inhibitor useful for the treatment of erectile dysfunction. See *Drugs of the Future*, 22, 138–143 (1997).

Female sexual arousal is part of the female sexual response cycle, and is characterized by increased vaginal lubrication, and increased clitoral and labial engorgement and sensation. Studies suggest a potential role for nitric oxide as a mediator of clitoral cavernosal and vaginal wall smooth muscle relaxation. Recently, PDE5 has been isolated in human clitoral smooth muscle culture. Therefore, a selective inhibitor of cGMP PDE5 provides means to restore diminished physiological arousal changes and improve subjective parameters of arousal in both pre- and post-menopausal women.

The present invention provides novel compounds which are potent and selective inhibitors of cGMP PDE 5. These compounds may be employed in the treatment of sexual dysfunction including erectile dysfunction and female sexual arousal disorder. In view of their activity, these compounds can also be employed in the treatment of other disorders responding to the inhibition of cGMP PDE such as various cardiovascular disorders.

SUMMARY OF THE INVENTION

The present invention is directed to the fused pyridopyridazine compounds of the formula I and salts thereof, for use as inhibitors of cGMP PDE, especially Type 5,

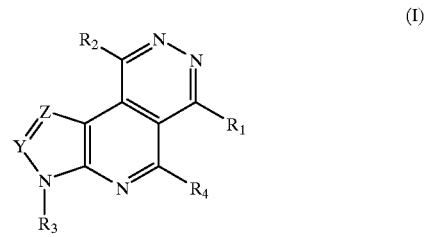

(I)

wherein:

Y is nitrogen or —C($R_5$)—;

Z is nitrogen or —C($R_6$)— provided that at least one of Y and Z is nitrogen;

$R_1$ and $R_2$ are independently selected from the group consisting of hydrogen, chloro, —$SR_7$, —$OR_7$, —$NR_8R_9$, and

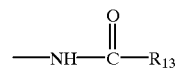

with the proviso that at least one of $R_1$ or $R_2$ is —$SR_7$, —$OR_7$, —$NR_8R_9$ or

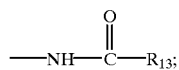

$R_3$ is hydrogen, alkyl, substituted alkyl, arylalkyl, or substituted arylalkyl;

$R_4$ is hydrogen, halogen, alkyl, substituted alkyl, —$OR_{10}$, or —$NR_{11}R_{12}$;

$R_5$ and $R_6$ are independently selected from the group onsisting of hydrogen, halogen, alkyl, and substituted alkyl;

$R_7$, $R_8$, and $R_9$ are independently selected from the group consisting of hydrogen, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl and heteroarylalkyl;

$R_8$ and $R_9$ together with the N atom to which they are attached can form a heterocyclo ring, a substituted or unsubstituted imidazole, a substituted or unsubstituted pyrazole, or a substituted or unsubstituted triazole;

$R_{10}$, $R_{11}$ and $R_{12}$ are independently selected from the group consisting of hydrogen, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl and heteroarylalkyl;

$R_{13}$ is alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl, or heteroarylalkyl.

DETAILED DESCRIPTION OF THE INVENTION

The following are definitions of the terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. The term alkyl when used at the end of a term, i.e. cycloalkylalkyl, arylalkyl, heterocycloalkyl, refers to a straight or branched chain carbon bridge of 1 to 12 carbon atoms, preferably 1 to 8 carbon atoms, and most preferably 1 to 4 carbon atoms such as —CH$_2$—, —CH$_2$—CH(CH$_3$)—, —(CH$_2$)$_4$—, etc.

The term "alkoxy" refers to an alkyl group as defined above bonded through an oxygen (—O—). The term "alkylthio" refers to an alkyl group as defined above bonded through a sulfur (—S—).

The term "cycloalkyl" refers to fully saturated and partially unsaturated hydrocarbon rings of 3 to 9, preferably 3 to 7, carbon atoms as well as such rings having a fused aryl ring such as indan.

The term "substituted cycloalkyl" refers to such rings having one, two or three substituents, preferably one, selected from the group consisting of alkyl, alkoxy, alkylthio, halo, hydroxy, cyano, amino, —NH(alkyl), —NH(cycloalkyl), —N(alkyl)$_2$,

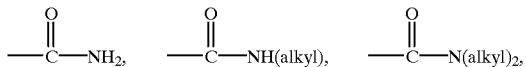

carboxy, —CO$_2$-lower alkyl, aryl, substituted aryl, arylalkyl, substituted arylalkyl, heterocyclo, heterocycloalkyl, heteroaryl, heteroarylalkyl, keto, =N—OH, =N—O-lower alkyl, and a five or six membered ketal, i.e 1,3-dioxolane or 1,3-dioxane.

The term "substituted alkyl" refers to an alkyl group as defined above having one, two or three substituents selected from the group consisting of halo, amino, cyano, —(CH$_2$)$_m$-hydroxy, alkoxy, alkylthio, —NH(alkyl), —NH(cycloalkyl), —N(alkyl)$_2$,

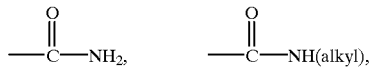

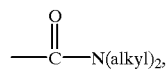

carboxy and —CO$_2$-alkyl.

The term "halo" refers to chloro, bromo, fluoro and iodo.

The term "aryl" refers to phenyl, 1-naphthyl and 2-naphthyl, with phenyl being preferred. The term "substituted aryl" refers to such rings having one, two or three substituents selected from the group consisting of alkyl, substituted alkyl, alkoxy, alkylthio, cycloalkyl, halo, hydroxy, nitro, cyano, amino, —NH(alkyl), —NH(cycloalkyl), —N(alkyl)$_2$, carboxy, —CO$_2$-alkyl,

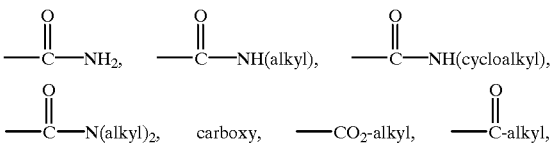

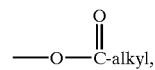

—NH—CH$_2$-carboxy, —NH—CH$_2$—CO$_2$-alkyl, phenyl, benzyl, phenylethyl, phenyloxy, phenylthio, heterocyclo, heterocycloalkyl, heteroaryl, and heteroarylalkyl, as well as pentafluorophenyl.

The term "heterocyclo" refers to substituted and unsubstituted saturated or partially saturated 3 to 7 membered monocyclic groups, 7 to 11 membered bicyclic groups and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom of any of the rings. The heterocyclo ring may contain one, two or three substituents selected from the group consisting of halo, formyl, amino, cyano, alkyl, substituted alkyl, cycloalkyl, substituted cycloalkyl, —NH(alkyl), —NH(cycloalkyl), —NH(substituted alkyl), —N(alkyl)$_2$, alkoxy, alkylthio, hydroxy, nitro, phenyl, substituted phenyl, phenyl-alkyl, substituted phenyl-alkyl, phenyloxy, phenylthio, carboxy, —CO$_2$-alkyl,

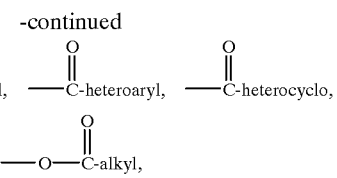

—NH—CH$_2$-carboxy, —NH—CH$_2$—CO$_2$-alkyl, heterocylco, heterocycloalkyl, heteroaryl, heteroarylalkyl, keto, =N—OH, =N—O-lower alkyl, and a five or six membered ketal, i.e 1,3-dioxolane or 1,3-dioxane.

Exemplary monocyclic groups include azetidinyl, pyrrolidinyl, oxetanyl, imidazolinyl, oxazolidinyl,

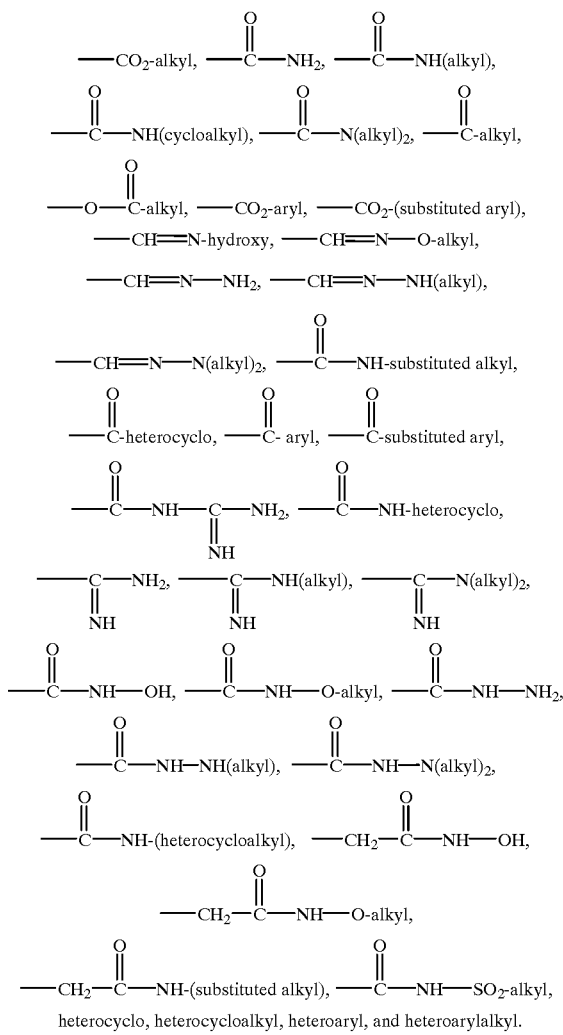

heterocyclo, heterocycloalkyl, heteroaryl, and heteroarylalkyl.

isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less. The fused rings completing the bicyclic and tricyclic groups may contain only carbon atoms and may be saturated, partially saturated or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain one, two or three substituents selected from the group consisting of halo, formyl, amino, cyano, alkyl, substituted alkyl, —NH(alkyl), —NH(cycloalkyl), —NH(substituted cycloalkyl), —NH (substituted alkyl), —NH(heterocycloalkyl), —N(alkyl)$_2$, alkoxy, alkylthio, cycloalkyl, substituted cycloalkyl, hydroxy, nitro, phenyl, phenylalkyl, substituted phenyl, substituted phenyl-alkyl, phenyloxy, phenylthio, carboxy, Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "substituted imidazole" refers to an imidazole, an aryl-fused imidazole such as benzimidazole, or a heteroaryl-fused imidazole such as a pyridoimidazole having one or two substituents selected from the group consisting of alkyl, substituted alkyl, alkoxy, alkylthio, cycloalkyl, substituted cycloalkyl, halo, formyl, hydroxy, nitro, cyano, amino, —NH(alkyl), —NH(cycloalkyl), —NH (heterocyloalkyl), —NH(substituted cycloalkyl), —NH (substituted alkyl),

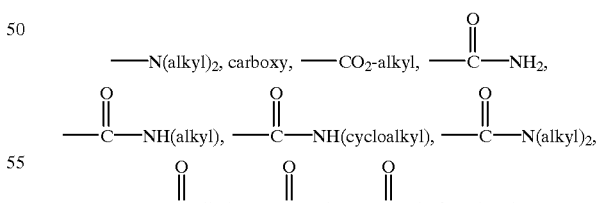

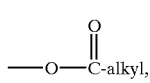

phenyl, substituted phenyl, phenylalkyl, (substituted phenyl)-alkyl, —CH=N-hydroxy, —CH=N—O-alkyl, —CH=N—NH$_2$, —CH=N—NH(alkyl),

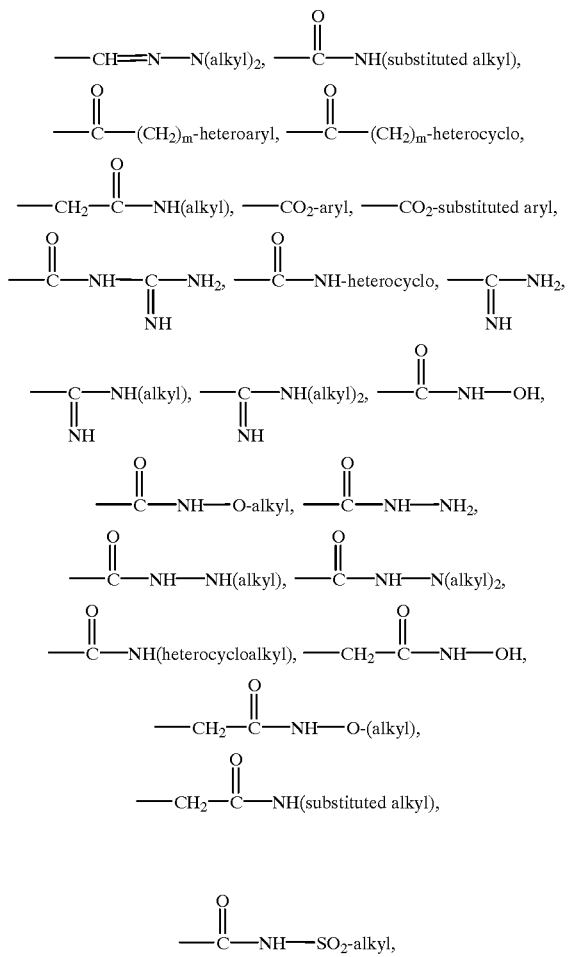

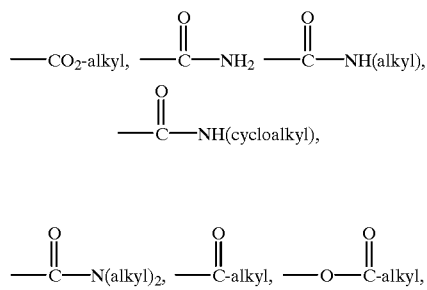

phenyloxy, phenylthio, heterocyclo, heterocycloalkyl, heteroaryl, and heteroarylalkyl.

The term "substituted pyrazole" refers to a pyrazole, an aryl-fused pyrazole such as benzopyrazole, or a heteroaryl-fused pyrazole such as a pyrazolopyridine having one or two substituents selected from the group consisting of alkyl, substituted alkyl, alkoxy, alkylthio, halo, hydroxy, nitro, cyano, amino, —NH(alkyl), —NH(cycloalkyl), —N(alkyl)$_2$, carboxy,

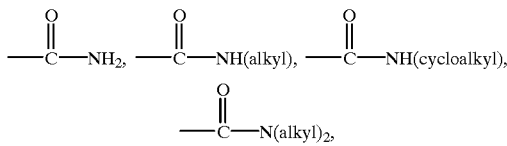

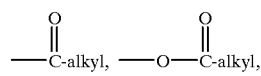

—NH—CH$_2$-carboxy, —NH—CH$_2$—CO$_2$-alkyl, phenyl, benzyl, phenylethyl, phenyloxy, phenylthio, heterocyclo, heterocycloalkyl, heteroaryl, and heteroarylalkyl.

The term "substituted triazole" refers to a triazole which can contain one substituent selected from the group consisting of alkyl, substituted alkyl, alkoxy, alkylthio, halo, hydroxy, nitro, cyano, amino, —NH(alkyl), —NH(cycloalkyl), —N(alkyl)$_2$, carboxy, —CO$_2$-alkyl, —NH—CH$_2$carboxy, —NH—CH$_2$—CO$_2$-alkyl, phenyl, benzyl, phenylethyl, phenyloxy, phenylthio, heterocyclo, heterocycloalkyl, heteroaryl, and heteroarylalkyl.

m is zero or an integer from 1 to 4.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of this invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

Compounds of the formula I, and salts thereof, may exist in their tautomeric form (for example, as an amide or imino ether). All such tautomeric forms are contemplated herein as part of the present invention.

All stereoisomers of the present compounds, such as those which may exist due to asymmetric carbons on the $R_1$ to $R_{12}$ substituents, including enantiomeric forms (which may exist even in the absence of asymmetric carbons) and diastereomeric forms, are contemplated and are within the scope of this invention. Individual stereoisomers of the compounds of this invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

METHODS OF PREPARATION

The compounds of the present invention may be prepared by methods such as those illustrated in the following Scheme I to VII. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, Y, Z, $R_1$, $R_2$, $R_3$, $R_4$, $R_5$ and $R_6$ are as described for a compound of formula I.

High Speed Analoging (HSA) may be employed in the preparation of compounds, for example, where the intermediates possess an activated aromatic position, such as the halogenated 3 or 6 position of a pyridazine. In the same manner, substitutions on the fused five membered ring, such as pyrazoles, imidazoles, and triazoles, may also be achieved through HSA.

SCHEME I

This scheme is directed to the preparation of the compounds of formula Ia [those of formula I wherein Y is nitrogen and Z is ——C($R_6$)——]. Et represents ethyl ($C_2H_5$).

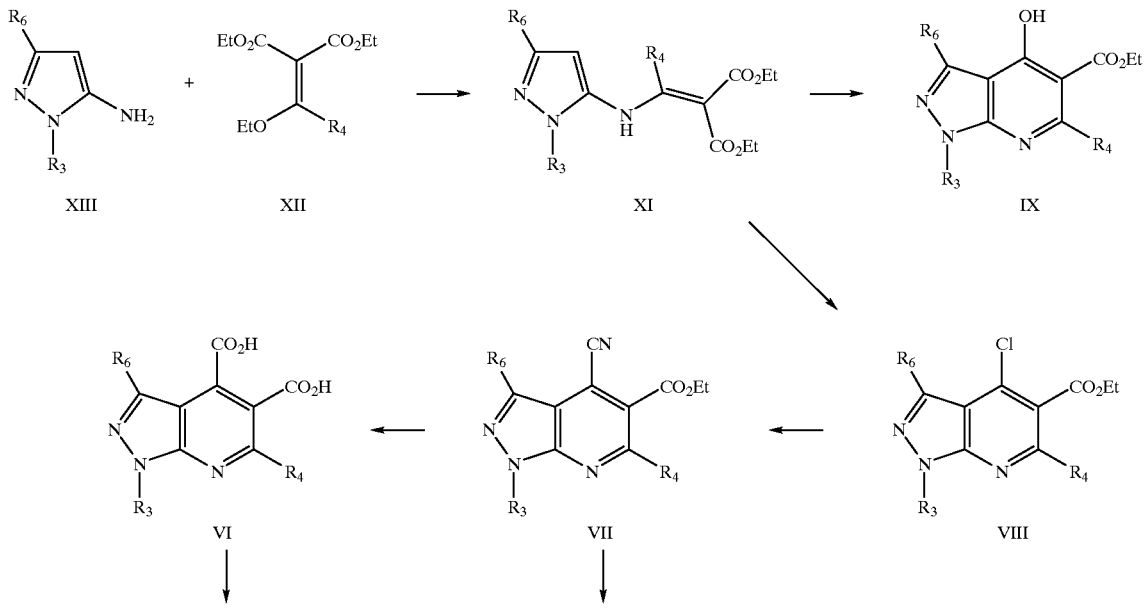

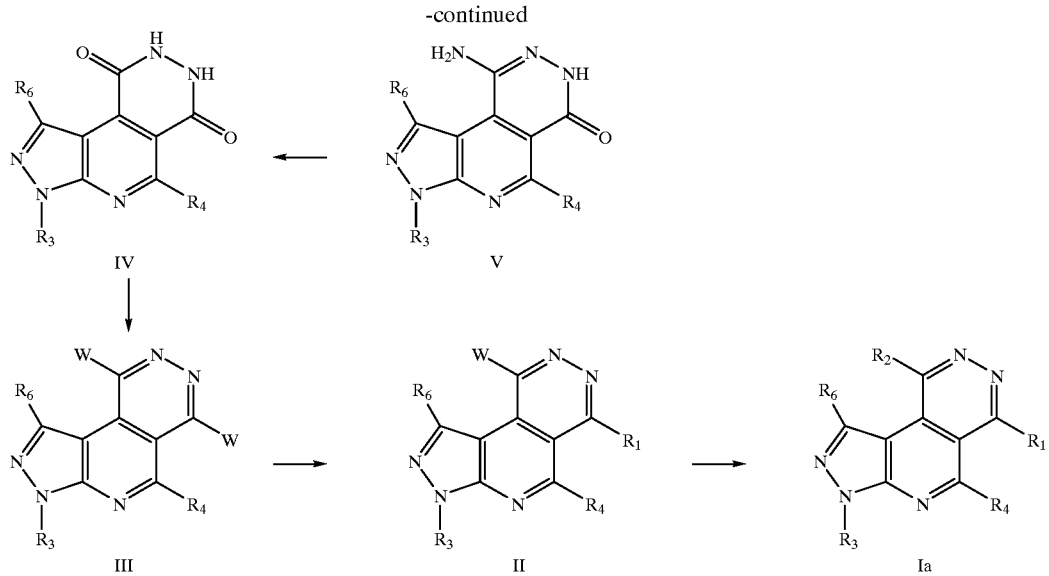

Compounds of formula Ia can be prepared by reactions of an amine, thiol or alcohol with compounds of formula II using an appropriate base in an inert solvent under elevated temperature. Exemplary bases include trialkylamines such as diisopropylethylamine and triethylamine, and 1,8-diazabicyclo[5.4.0]undec-7-ene (DBU). Exemplary inert solvents include N-methylpyrrolidinone and N,N-dimethylformamide.

Compounds of formula II can be prepared by reacting an amine, thiol or alcohol with compounds of formula III in an inert solvent and an appropriate base. This reaction can be performed at a temperature of between about 0° C. to about 110° C. Exemplary bases include trialkylamines such as diisopropylethylamine and triethylamine, DBU and carbonates such as potassium carbonate, sodium carbonate and cesium carbonate. Exemplary inert solvents include tetrahydrofuran (THF), ethanol, N-methylpyrrolidinone, and N,N-dimethylformamide.

Compounds of formula III wherein W is chloro, which is preferred, bromo, or iodo can be prepared from compounds of formula IV by reacting with an appropriate dehydrating agent typically under elevated temperature. Exemplary dehydrating agents include phosphorus oxychloride, phosphorus pentachloride, thionyl chloride, oxalyl chloride, phosphorus pentabromide, phosphorus oxybromide, phosphorus pentaiodide, phosphorus oxyiodide, etc. This reaction can be performed in the presence of a cosolvent such as benzene, toluene, xylene, etc. Optionally, a base such as pyridine or a trialkylamine may be present.

Compounds of formula IV can be prepared from compounds of formula V. Compounds of formula V can be transformed to IV by either hydrolysis or by diazatization in an acidic aqueous medium under elevated temperature. Exemplary acids include hydrogen chloride, sulfuric acid, and nitric acid. Exemplary diazatization agents include sodium nitrite and organic nitrites such as t-butyl nitrite.

Compounds of formula IV can be prepared from compounds of formula VI by reacting with hydrazine alone or in combination with a carboxylic acid activating agent in an inert solvent. Exemplary carboxylic acid activating agents include carbonyldiimidazole, dicyclohexylcarbodiimide, pentofluorophenol trifluoroacetate, and 1-(3-dimethylaminopropyl)-3-ethylcarbodiimide. Exemplary inert solvents include alcohols, tetrahydrofuran, methylene dichloride, diethyl ether, and N,N-dimethylformamide.

Compounds of formula V can be prepared by reacting compounds of formula VII with hydrazine in an inert solvent. Exemplary inert solvents include tetrahydrofuran, ethanol, and N,N-dimethylformamide.

Compounds of formula VI can be prepared by reacting compounds of formula VII with a hydroxide source. Exemplary hydroxide sources include sodium hydroxide and lithium hydroxide. Exemplary solvents include water, alcohols, and mixtures of ethers/water.

Compounds of formula VII can be prepared by reacting compounds of formula VIII with a cyanide donor in an inert solvent typically under elevated temperature. Exemplary cyanide donors include inorganic cyanides such sodium cyanide, potassium cyanide and copper (I) cyanide, and organic cyanides such as tetrabutylammonium cyanide. A combination of inorganic cyanides with a phase transferring agents such as tetrabutylammonium salts can also be utilized. Inert solvents include N,N-dimethylformamide, ethanol, and tetrahydrofuran (THF).

Compounds of formula VIII can be prepared from compounds of either formula IX or formula XI by reacting with an appropriate dehydrating agent typically under elevated temperature. Exemplary dehydrating agents include phosphorus oxychloride, phosphorus pentachloride, thionyl chloride and oxalyl chloride.

Compounds of formula IX can be prepared from compounds of formula XI via an intramolecular cyclization typically under elevated temperature in an inert solvent, for example, biphenyl ether, or in neat form.

Compounds of formula XI can be prepared by combining compounds of formula XII and XIII either neat or in an inert solvent, for example, biphenyl ether, typically under elevated temperature.

Compounds of formula XII and formula XIII are either commercially available or available via methods known to one skilled in the art. For example, compounds of formula XII may be prepared as described in French Patent 1,403,372 [Chemical Abstracts, 1965, Volume 63, 14871a].

SCHEME II

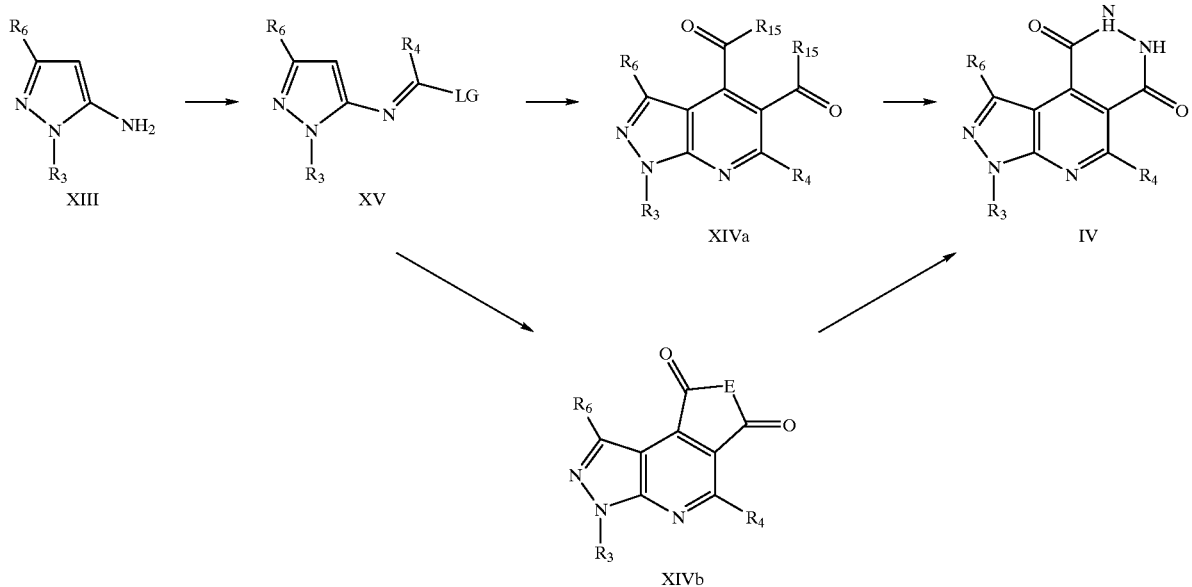

Compounds of formula IV which are useful intermediates for the synthesis of compounds of formula Ia can also be prepared by the reaction of hydrazine with compounds of formula XIVa wherein $R_{15}$ is —O-alkyl or by the reaction of hydrazine with compounds of formula XIVb wherein E is an oxygen atom, —NH— or —N(alkyl)—. These reactions are performed in an inert solvent typically under elevated temperature. Exemplary inert solvents include alcohols, ethers such as tetrahydrofuran, or N,N-dimethylformamide.

Compounds of formula XIVa and XIVb can be prepared from the Diels-Alder reaction of compounds of formula XV wherein LG is —O-alkyl or —N(alkyl)$_2$ with an appropriate electron poor dienophile in a protic solvent. Exemplary dienophiles include dimethylacetylene dicarboxylate, maleic anhydride, maleimide and N-methylmaleimide. In the case of olefin based dienophiles, a concomitant aromatization mediated by oxygen occurs. Exemplary protic solvents include water, acetic acid, and trifluoroacetic acid.

Compounds of formula XV wherein LG is —O-alkyl or —N(alkyl)$_2$ can be prepared by reacting compounds of formula XIII with either N,N-dialkylamide dialkylacetals, such as N,N-dimethylformamide dimethyl acetal, or orthoesters, such as trimethylorthoformate, in an inert solvent or in neat form under elevated temperature. Exemplary inert solvents include ethers such as tetrahydrofuran, methylene chloride, or N,N-dimethylformamide.

Scheme III
This scheme is directed to the preparation of the compounds of formula Ib
(those of formula I wherein Y and Z are both nitrogen). $R_{30}$ is alkyl.

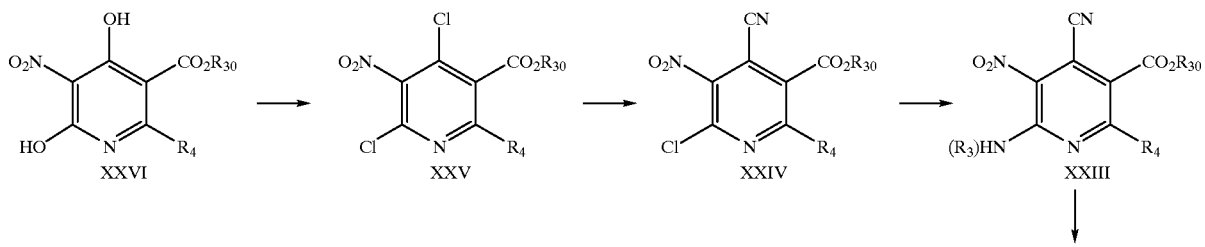

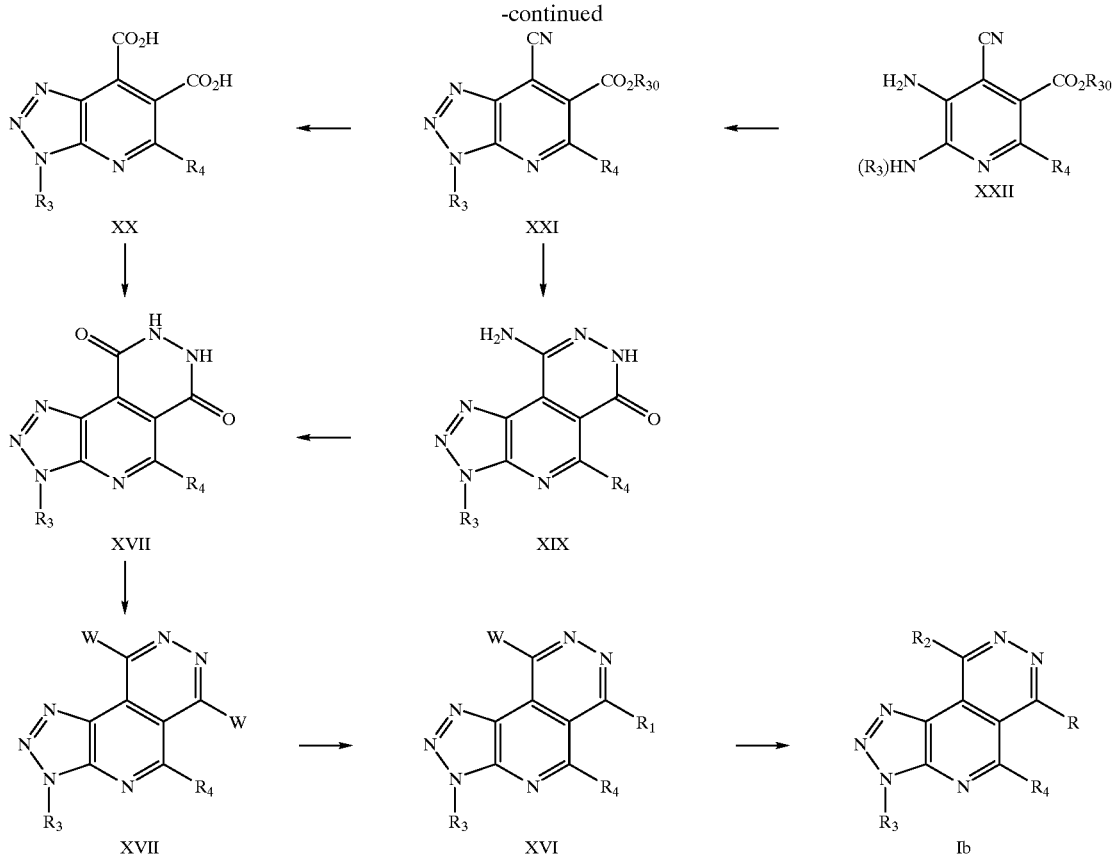

Compounds of formula Ib can be prepared by reactions of an amine, thiol or alcohol with compounds of formula XVI using an appropriate base in an inert solvent under elevated temperature. Exemplary bases include trialkylamines such as diisopropylethylamine and triethylamine, and DBU. Exemplary inert solvents include N-methylpyrrolidinone and N,N-dimethylformamide.

Compounds XVI can be prepared by reacting an amine, thiol or alcohol with compounds of formula XVII using an appropriate base in an inert solvent. This reaction can be performed at a temperature of between about 0° C. and 110° C. Exemplary bases include trialkylamines such as diisopropylethylamine and triethylamine, DBU, and carbonates such as potassium carbonate, sodium carbonate and cesium carbonate. Exemplary inert solvents include tetrahydrofuran (THF), ethanol, N-methylpyrrolidinone and N,N-dimethylformamide.

Compounds of formula XVII wherein W is chloro, which is preferred, bromo or iodo can be prepared from compounds of formula XVIII by reacting with an appropriate dehydrating agent typically under elevated temperature. Exemplary dehydrating agents include phosphorus oxychloride, phosphorus pentachloride, thionyl chloride, oxalyl chloride, phosphorus pentabromide, phosphorus oxybromide, phosphorus pentaiodide, phosphorus oxyiodide, etc. The reaction can be performed in the presence of a cosolvent such as benzene, toluene, xylene, etc. Optionally, a base such as pyridine or a trialkylamine may be present.

Compounds of formula XVIII can be prepared from compounds of formula XIX. Compounds of formula XIX can be transformed to formula XVIII by either hydrolysis or by diazatization in an acidic aqueous medium under elevated temperature. Exemplary acids include hydrogen chloride, sulfuric acid and nitric acid. Exemplary diazatization agents include sodium nitrite and organic nitrites such as t-butyl nitrite.

Compounds of formula XVIII can be prepared from compounds of formula of XX by reacting with hydrazine alone or in combination with a carboxylic acid activating agent in an inert solvent. Exemplary carboxylic acid activating agents include carbonyldiimidazole, dicyclohexylcarbodiimide, pentofluorophenol trifluoroacetate, and 1-(3-dimethylaminopropyl)-3-ethylcarbodiimide. Exemplary inert solvents include tetrahydrofuran, methylene dichloride, diethyl ether and N,N-dimethylformamide.

Compounds of formula XIX can be prepared by reacting compounds of formula XXI with hydrazine in an inert solvent. Exemplary inert solvents include tetrahydrofuran, ethanol, and N,N-dimethylformamide.

Compounds of formula XX can be prepared by reacting compounds of formula XXI with a hydroxide source. Exemplary hydroxide sources include sodium hydroxide and lithium hydroxide. Exemplary solvents include water, alcohols, and mixtures of ethers/water.

Compounds of formula XXI can be prepared by treating a compound of formula XXII with a diazatizing reagent in an acidic aqueous medium. Sodium nitrite is an exemplary diazatizing reagent and dilute (1N) HCl is an exemplary reaction solvent.

Compounds of formula XXII can be prepared via the reduction of compounds of formula XXIII in an inert solvent. This reduction may, for example, be mediated via a platinum or palladium-catalyzed hydrogenation using platinum or palladium on carbon, hydrogen and an inert solvent such as ethanol or methanol or, alternatively, by use of a stoichiometric reducing agent, such as stannous(II) chloride, in an inert solvent such as ethyl acetate.

Compounds of formula XXIII can be prepared by reacting compounds of formula XXIV with amines of the formula $R_3NH_2$. The reaction may be performed in an inert solvent as appropriate, such as ethanol, in the presence of an appropriate base, such as triethylamine, and typically under elevated temperature.

Compounds of formula XXIV can be prepared by reacting compounds of formula XXV with a cyanide donor in an inert solvent typically under elevated temperature. Exemplary cyanide donors include inorganic cyanides such as sodium cyanide, potassium cyanide and copper(I) cyanide, and organic cyanides such as tetrabutylammonium cyanide. A combination of inorganic cyanides with a phase transferring agents such as tetrabutylammonium salts can also be utilized. Inert solvents include N,N-dimethylformamide, ethanol, and THF.

Methods of synthesis of compounds of formula XXI, XXII, XXIII, XXIV, XXV and XXVI are known to one skilled in the art. For example such methodology can be found in U.S. Pat. Nos. 4,070,362, 4,003,908, and 4,048,182. Compounds of formula XXVI are either commercially available or prepared by methods known to one skilled in the art.

Compounds of formula Ic can be prepared by reactions of an amine, thiol or alcohol with compounds of formula XXVII using an appropriate base in an inert solvent under elevated temperature. Exemplary bases include trialkylamines such as diisopropylethylamine and triethylamine, and DBU. Exemplary inert solvents include N-methylpyrrolidinone and N,N-dimethylformamide.

Compounds of formula XXVII can be prepared by reacting an amine, thiol or alcohol with compounds of formula XXVIII using an appropriate base in an inert solvent. This reaction can be performed at a temperature of between about 0° C. to about 110° C. Exemplary bases include trialkylamines such as diisopropylethylamine and triethylamine, DBU and carbonates such as potassium carbonate, sodium carbonate and cesium carbonate. Exemplary inert solvents include tetrahydrofuran (THF), ethanol, N-methylpyrrolidinone and N,N-dimethylformamide.

Compounds of formula XXVIII wherein W is chloro, which is preferred, bromo or iodo can be prepared from compounds of formula XXIX by reacting with an appropriate dehydrating agent typically under elevated temperature. Exemplary dehydrating agents include phosphorus oxychloride, phosphorus pentachloride, thionyl chloride, oxalyl chloride, phosphorus bromide, phosphorus oxybromide, phosphorus pentaiodide, phosphorus oxyiodide, etc. This reaction can be performed in the presence of a cosolvent such as benzene, toluene, xylene, etc. Optionally, a base such as pyridine or a trialkylamine may be present.

Scheme IV
This scheme is directed to the preparation of the compounds of formula Ic
(those of formula I wherein Y is ——C($R_5$)— and Z is nitrogen). $R_{30}$ is alkyl.

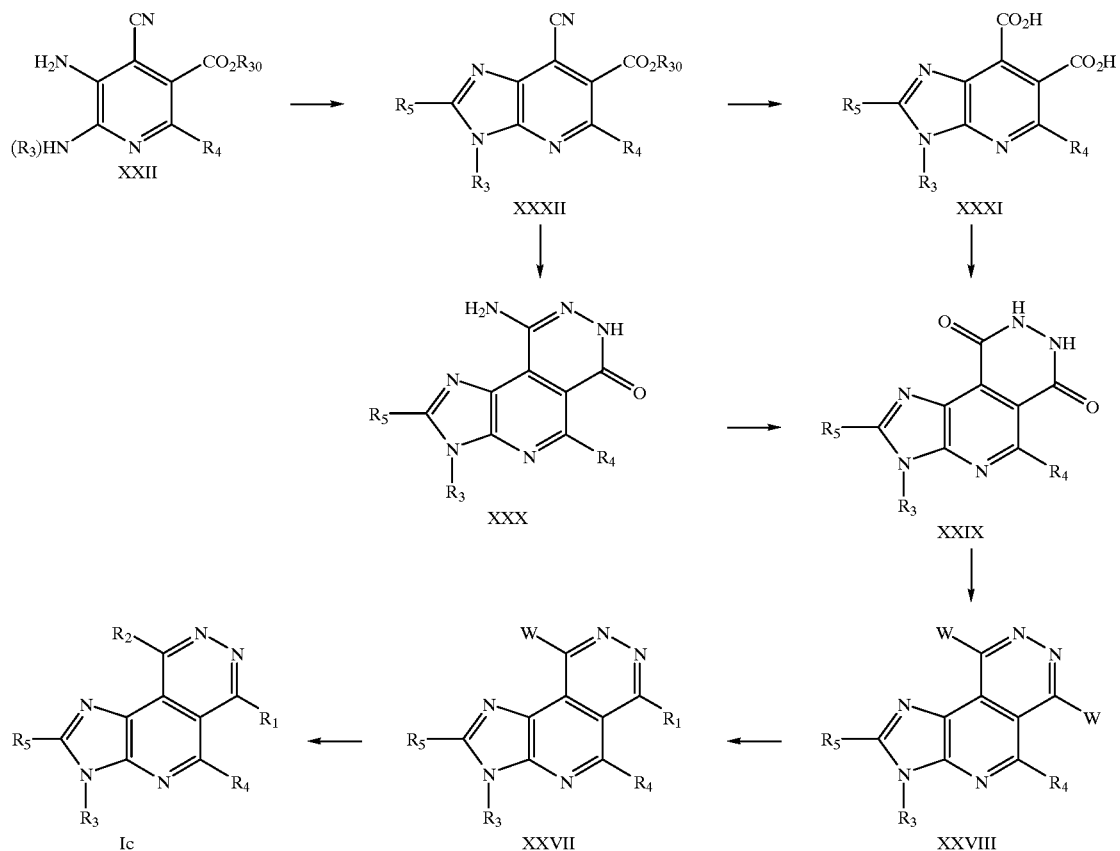

Compounds of formula XXIX can be prepared from compounds of either formula XXX or formula XXXI. Compounds of formula XXX can be transformed to XXIX by either hydrolysis or by diazatization in an acidic aqueous medium under elevated temperature. Compounds of formula XXXI can be transformed to XXIX by reacting with hydrazine alone or in combination with a carboxylic acid activating agent in an inert solvent. Exemplary acids include hydrogen chloride, sulfuric acid, and nitric acid. Exemplary diazatization agents include sodium nitrite and organic nitrites such as t-butyl nitrite. Exemplary carboxylic acid activating agents include carbonyldiimidazole, dicyclohexylcarbodiimide, pentofluorophenol trifluoroacetate, and 1-(3-dimethylaminopropyl)-3-ethylcarbodiimide. Exemplary inert solvents include tetrahydrofuran, methylene dichloride, diethyl ether, and N,N-dimethylformamide.

Compounds of formula XXX can be prepared by reacting compounds of formula XXXII with hydrazine in an inert solvent. Exemplary inert solvents include tetrahydrofuran, ethanol, and N,N-dimethylformamide.

Compounds of formula XXXI can be prepared by reacting compounds of formula XXXII with a hydroxide source. Exemplary hydroxide sources include sodium hydroxide and lithium hydroxide. Exemplary solvents include water, alcohols, and mixtures of ethers/water.

Compounds of formula XXXII can be prepared from the condensation of compounds of formula XXII with an activated ester derivative from an acid of the formula $R_7$—$CO_2H$ under basic conditions or acidic conditions in an inert solvent typically under elevated temperature. Exemplary activated esters include acid chlorides derived from $R_7$—$CO_2H$, N,N-dialkylamide dialkylacetals, such as N,N-dimethylformamide dimethyl acetal, and activated esters derived from the reaction of $R_7$—$CO_2H$ with exemplary carboxylic acid activating agents such as carbonyldiimidazole, dicyclohexylcarbodiimide, pentofluorophenol trifluoroacetate, and 1-(3-dimethylaminopropyl)-3-ethylcarbodiimide. Exemplary bases include sodium hydride, potassium hydride, cesium carbonate, potassium carbonate, potassium hexamethyldisilazide, and potassium t-butoxide. Exemplary acids or Lewis acids include hydrogen chloride and zinc chloride. Exemplary inert solvents include ethers, N,N-dimethylformamide, and acetonitrile.

Compounds of formula XXII are prepared as discussed in Scheme III.

Scheme V
This scheme is directed to the preparation of the compounds of formula Id [those of formula I wherein Y is nitrogen, Z is ——C($R_6$)——, and ——$R_1$ is chloro] and the compounds of formula Ie [those of formula I wherein Y is nitrogen, Z is ——C($R_6$)——, and ——$R_1$ is hydrogen].

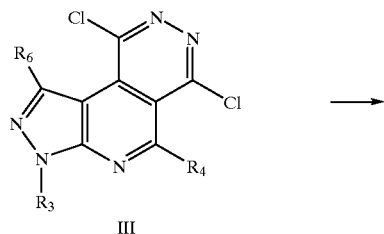

III

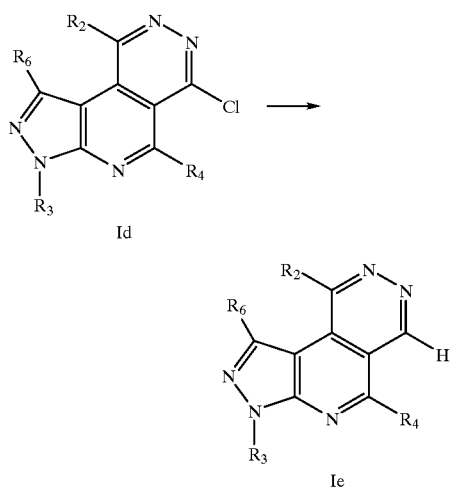

Id

Ie

Compounds of formula Id can be prepared by reactions of an amine, thiol or alcohol with compounds of formula III using an appropriate base in an inert solvent under elevated temperature. Exemplary bases include trialkylamines such as diisopropylethylamine and triethylamine, and DBU. Exemplary inert solvents include N-methylpyrrolidinone and N,N-dimethylformamide.

Compounds of formula Ie can be prepared by the reduction of compounds of formula Id using a hydrogen source and a transition metal catalyst. Exemplary hydrogen sources include hydrogen and ammonium formate. Exemplary transition metal catalysts include palladium on carbon and palladium hydroxide on carbon.

Scheme VI
This scheme is directed to the preparation of the compounds of formula If [those of formula I wherein Y is nitrogen, Z is nitrogen, and ——$R_1$ is chloro] and the compounds of formula Ig [those of formula I wherein Y is nitrogen, Z is nitrogen and ——$R_1$ is hydrogen].

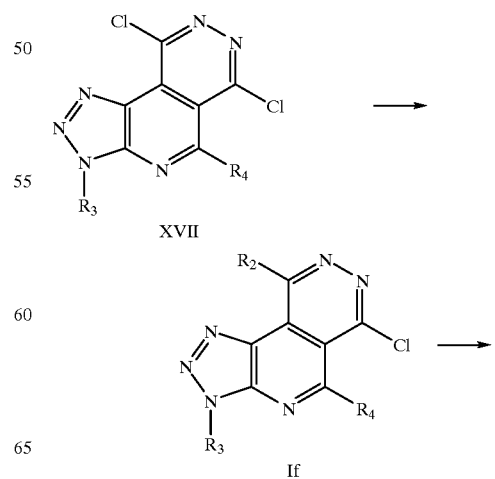

XVII

If

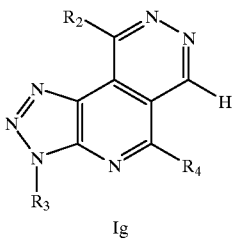

Compounds of formula If can be prepared by reactions of an amine, thiol or alcohol with compounds of formula XVII using an appropriate base in an inert solvent under elevated temperature. Exemplary bases include trialkylamines such as diisopropylethylamine and triethylamine, and DBU. Exemplary inert soylents include N-methylpyrrolidinone and N,N-dimethylformamdide.

Compounds of formula Ig can be prepared by the reduction of compounds of formula If using a hydrogen source and a transition metal catalyst. Exemplary hydrogen sources include hydrogen and ammonium formate. Exemplary transition metal catalysts includes palladium on carbon and palladium hydroxide on carbon.

Scheme VII
This scheme is directed to the preparation of the compounds of formula Ih [those of formula I wherein Y is ——C(R$_5$)——, and Z is nitrogen, and ——R$_1$ is chloro] and the compounds of formula Ij [those of formula I wherein Y is ——C(R$_5$)——, Z is nitrogen, and ——R$_1$ is hydrogen].

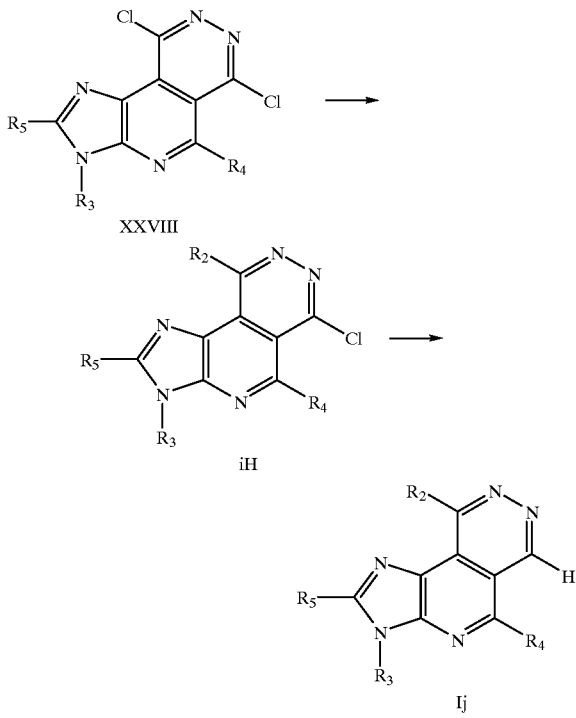

Compounds of formula Ih can be prepared by reactions of an amine, thiol or alcohol with compounds of formula XXVIII using an appropriate base in an inert solvent under elevated temperature. Exemplary bases include trialkylamines such as diisopropylethylamine and triethylamine, and DBU. Exemplary inert solvents include N-methylpyrrolidinone and N,N-dimethylformamide.

Compounds of formula Ij can be prepared by the reduction of compounds of formula Ih using a hydrogen source and a transition metal catalyst. Exemplary hydrogen sources include hydrogen and ammonium formate. Exemplary transition metal catalysts include palladium on carbon and palladium hydroxide on carbon.

Preferred Compounds

Preferred compounds of this invention are those of formula I including pharmaceutically acceptable salts thereof having the following definitions:

Y is nitrogen or —C(R$_5$)—;

Z is nitrogen or —C(R$_6$)— provided that at least one of Y and Z is nitrogen;

R$_1$ and R$_2$ are independently selected from the group consisting of —NR$_8$R$_9$, hydrogen and chloro with the proviso that at least one of R$_1$ or R$_2$ is —NR$_8$R$_9$;

R$_3$ is hydrogen, alkyl, substituted alkyl, —(CH$_2$)$_n$-phenyl, or —(CH$_2$)$_n$-substituted phenyl;

R$_4$ is hydrogen, halogen, substituted alkyl, —OR$_{10}$ or —NR$_{11}$R$_{12}$;

R$_5$ and R$_6$ are independently selected from the group consisting of hydrogen, halogen, alkyl, and substituted alkyl;

R$_8$ and R$_9$ are independently selected from the group consisting of hydrogen, alkyl, substituted alkyl, —(CH$_2$)$_m$-cycloalkyl, —(CH$_2$)$_m$-substituted cycloalkyl, —(CH$_2$)$_m$-phenyl, —(CH$_2$)$_m$-substituted phenyl, —(CH$_2$)$_m$-heterocyclo, and —(CH$_2$)$_m$-heteroaryl or R$_8$ and R$_9$ taken together with the N atom to which they are attached can form a heterocyclo ring, a substituted or unsubstituted imidazole, a substituted or unsubstituted pyrazole, or a substituted or unsubstituted triazole;

R$_{10}$, R$_{11}$ and R$_{12}$ are independently selected from the group consisting of hydrogen, alkyl, —(CH$_2$)$_m$-phenyl, —(CH$_2$)$_m$-substituted phenyl, and —(CH$_2$)$_m$-heteroaryl;

m is zero or an integer from 1 to 4;

n is an integer from 1 to 4.

In the above preferred groups the following definitions apply:

The term "alkyl" refers to straight and branched chain groups of 1 to 8 carbons.

The term "substituted alkyl" and "substituted lower alkyl" refers to such alkyl and lower alkyl groups having one, two or three substituents selected from the group consisting of halo, —(CH$_2$)$_m$-hydroxy, cyano, lower alkoxy, lower alkylthio, amino, —NH(lower alkyl), —N(lower alkyl)$_2$;

$$\overset{O}{\underset{\|}{-C}}-NH_2, \quad \overset{O}{\underset{\|}{-C}}-NH(\text{lower alkyl}) \quad \overset{O}{\underset{\|}{-C}}-N(\text{lower alkyl})_2,$$

carboxy, and —CO$_2$-lower alkyl.

The term "cyloalkyl" refers to unsubstituted fully saturated rings of 3 to 7 carbon atoms.

The term "substituted cycloalkyl" refers to such cycloalkyl rings having one, or three substituents preferably one substituent, selected from the group consisting of lower alkyl, lower alkoxy, lower alkylthio, halo, —(CH$_2$)$_m$-hydroxy, cyano, amino, —NH(lower alkyl), —NH(cycloalkyl), —N(lower alkyl)$_2$,

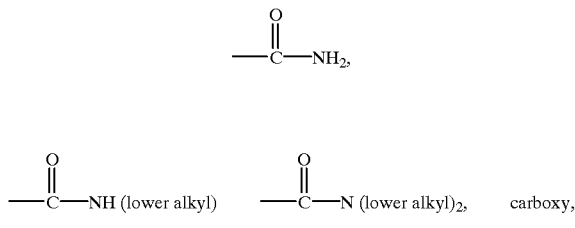

—CO$_2$-lower alkyl, —(CH$_2$)$_m$-phenyl, —(CH$_2$)$_m$-substituted phenyl, —(CH$_2$)$_m$-heterocyclo, —(CH$_2$)$_m$-heteroaryl, keto, =N—OH, =N—O-lower alkyl, and a five or six membered ketal, i.e 1,3-dioxolane or 1,3-dioxane.

The term "substituted phenyl" refers to a phenyl ring having one, two or three substituents selected from the group consisting of lower alkyl, lower alkoxy, lower alkylthio, halo, cyano, hydroxy, substituted lower alkyl, nitro, amino, —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, —CO$_2$-lower alkyl,

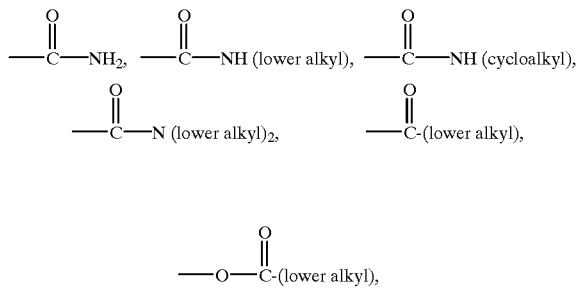

—NH—CH$_2$-carboxy, —NH—CH$_2$—CO$_2$-lower alkyl, and —(CH$_2$)$_m$-heteroaryl, as well as pentafluorophenyl.

The term "heterocyclo" refers to substituted and unsubstituted saturated or partially saturated 3 to 7 membered monocyclic rings having one or two O or S atoms and/or one to four N atoms provided that the total number of heteroatoms is four or less and that the heterocyclo ring contains at least one carbon atom, the nitrogen and sulfur atoms may optionally be oxidized, and the nitrogen atoms may optionally be quaternized. The heterocyclo substituent is one, two or three substituents attached to an available carbon or nitrogen atom and selected from the group consisting of halo, hydroxy, cyano, lower alkyl, cycloalkyl, substituted lower alkyl, lower alkoxy, lower alkylthio, keto, formyl, nitro, amino —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, substituted phenyl, substituted phenyl-CH$_2$—, substituted phenyl-CH$_2$—CH$_2$—, —CO$_2$-lower alkyl,

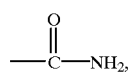

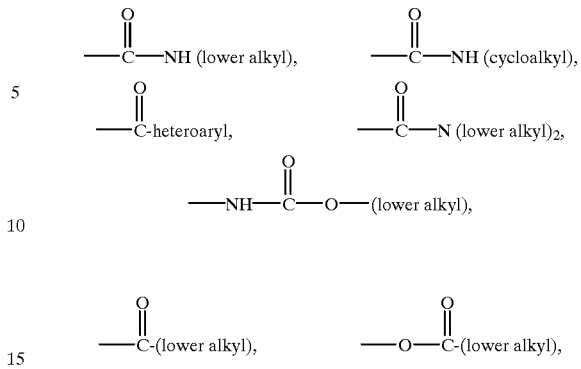

—NH—CH$_2$-carboxy, —NH—CH$_2$—CO$_2$-lower alkyl, —(CH$_2$)$_m$-heterocyclo, —(CH$_2$)$_m$-heteroaryl, =N—OH, =N—O-lower alkyl, and a five or six membered ketal, i.e 1,3-dioxolane or 1,3-dioxane as well as such heterocyclo rings fused to a phenyl ring.

The term "heteroaryl" refers to 5 or 6 membered substituted or unsubstituted monocylic aromatic rings having one or two O or S atoms and/or one to four N atoms provided that the total number of heteroatoms in the ring is four or less, and 9 or 10 membered substituted or unsubstituted bicyclic rings wherein at least one of the rings is aromatic and wherein at least one of the rings contains one or two O or S atoms and/or one to four N atoms provided that the total number of heteroatoms in either ring is four or less. The nitrogen and sulfur atoms may may optionally be oxidized, and the nitrogen atoms may optionally be quaternized. The heteroaryl substituent is attached to an available carbon atom and is one, two or three substituents selected from halo, cyano, lower alkyl, cycloalkyl, substituted lower alkyl, lower alkoxy, lower alkylthio, hydroxy, nitro, formyl, amino, —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, substituted phenyl, substituted phenyl-CH$_2$—, substituted phenyl-CH$_2$—CH$_2$—,

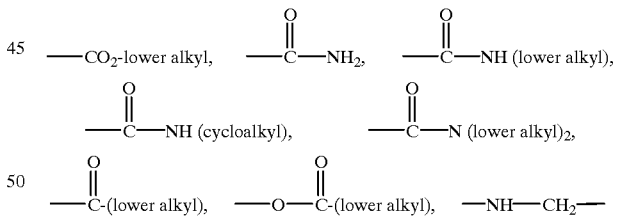

carboxy, —NH—CH$_2$—CO$_2$-lower alkyl, —(CH$_2$)$_m$-heterocyclo, and —(CH$_2$)$_m$-heteroaryl.

The term "substituted imidazole" refers to an imidazole, an aryl-fused imidazole such as benzimidazole, or a heteroaryl-fused imidazole such as a pyridoimidazole having one or two substituents selected from the group consisting of lower alkyl, cycloalkyl, substituted lower alkyl, lower alkoxy, lower alkylthio, nitro, halo, cyano, formyl, amino, —NH(lower alkyl), —NH(cycloalkyl), —NH(substituted lower alkyl), and —N(lower alkyl)$_2$, and/or one substituent selected from the group consisting of phenyl, benzyl, phenylethyl, substituted phenyl, substituted phenyl-CH$_2$—, substituted phenyl-CH$_2$—CH$_2$—, phenyloxy, phenylthio, carboxy, —CO$_2$-lower alkyl,

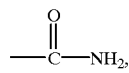

—CH=N-hydroxy, —CH=N—O-lower alkyl,

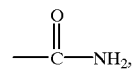

—NH—CH$_2$-carboxy, —NH—CH$_2$—CO$_2$-lower alkyl, —(CH$_2$)$_m$-heterocyclo, and —(CH$_2$)$_m$-heteroaryl.

The term "substituted pyrazole" refers to an pyrazole, a aryl-fused pyrazole such as benzopyrazole, or a heteroaryl-fused pyrazole such as a pyrazolopyridine having one or two substituents selected from the group consisting of lower alkyl, substituted lower alkyl, lower alkoxy, lower alkylthio, hydroxy, nitro, halo, cyano, amino, —NH(lower alkyl), —NH(cycloalkyl), and —N(lower alkyl)$_2$, and/or one substituent selected from the group consisting of phenyl, benzyl, substituted phenyl, substituted phenyl-CH$_2$—, substituted phenyl-CH$_2$—CH$_2$—, phenylethyl, phenyloxy, phenylthio, carboxy, —CO$_2$-lower alkyl,

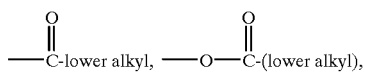

—NH—CH$_2$-carboxy, —NH—CH$_2$—CO$_2$-lower alkyl, —(CH$_2$)$_m$-heterocyclo, and —(CH$_2$)$_m$-heteroaryl.

The term "substituted triazole" refers to a triazole having one substituent selected from the group consisting of lower alkyl, substituted lower alkyl, lower alkoxy, lower alkylthio, hydroxy, halo, cyano, amino, —NH(lower alkyl), —NH(cycloalkyl), —N(lower alkyl)$_2$, phenyl, benzyl phenylethyl, substituted phenyl, substituted phenyl-CH$_2$—, substituted phenyl-CH$_2$—CH$_2$—, phenyloxy, phenylthio, carboxy, —CO$_2$-lower

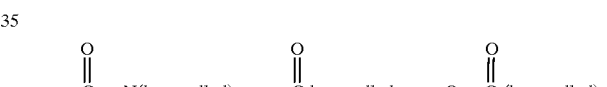

—NH—CH$_2$-carboxy, —NH—CH$_2$—CO$_2$-lower alkyl, —(CH$_2$)$_m$-heterocyclo, and —(CH$_2$)$_m$-heteroaryl.

More preferred are the compounds of formula I and pharmaceutically acceptable salts thereof having the following definitions:

Y is nitrogen.

Z is —C(R$_6$)—.

R$_1$ and R$_2$ are independently selected from the group consisting of —NR$_8$R$_9$, hydrogen and chloro with the proviso that at least one of R$_1$ or R$_2$ is —NR$_8$R$_9$.

R$_3$ is hydrogen, lower alkyl, —(CH$_2$)$_n$-phenyl, or —(CH$_2$)$_n$-substituted phenyl.

R$_4$ is hydrogen.

R$_6$ is hydrogen.

R$_8$ and R$_9$ are independently selected from the group consisting of hydrogen, lower alkyl, substituted lower alkyl, —(CH$_2$)$_m$-cyclohexyl, —(CH$_2$)$_m$-substituted cyclohexyl, —(CH$_2$)$_m$-phenyl, —(CH$_2$)$_m$-substituted phenyl, —(CH$_2$)$_m$-heterocyclo, —(CH$_2$)$_m$-heteroaryl or R$_8$ and R$_9$ taken together with the N atom to which they are attached can form a heterocyclo ring or a substituted or unsubstituted imidazole.

m is zero or an integer from 1 to 4.

n is an integer from 1 to 4.

In the above more preferred groups the following definitions apply:

The term "lower alkyl" refers to straight and branched chain groups of 1 to 4 carbons.

The term "substituted lower alkyl" refers to such lower alkyl groups having a single substituent selected from the group consisting of halo, —$(CH_2)_m$-hydroxy, lower alkoxy, amino, —NH(lower alkyl), —NH(cycloalkyl of 3 to 6 carbons), —N(lower alkyl)$_2$, carboxy, —$CO_2$ lower alkyl,

and

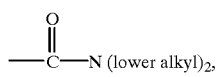

The term "substituted phenyl" refers to a phenyl ring having one, two or three substituents selected from the group consisting of halo, cyano, lower alkyl, lower alkoxy, —$(CH_2)_m$-hydroxy, trifluoromethyl, amino, —NH(lower alkyl), —NH(cycloalkyl of 3 to 6 carbons), and —N(lower alkyl)$_2$, and/or one substituted selected from the group consisting of carboxy, —$CO_2$-lower alkyl,

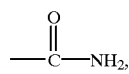

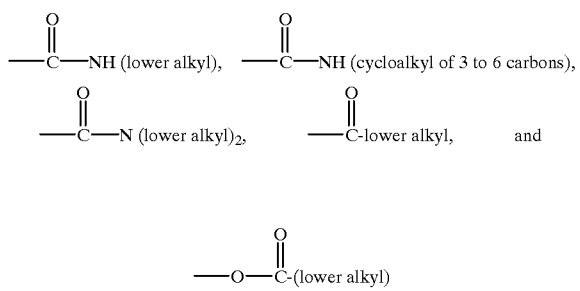

as well as pentafluorophenyl.

The term "heterocyclo" refers to 3 to 7 membered substituted or unsubstituted monocyclic saturated or partially saturated rings having one or two O or S atoms and or one to four N atoms provided that the total number of heteroatoms in the ring is four or less, and the ring contains at least one carbon atom. The nitrogen and sulfur atoms may optionally be oxidized, and the nitrogen may optionally be quaternized. The heterocyclo substituent or substituents are attached to an available carbon or nitrogen atom and are one or two members selected from the carbon or nitrogen atom and are one or two members selected from the group consisting of halo, keto, hydroxy, cyano, lower alkyl, substituted lower alkyl, cycloalkyl of 3 to 6 carbons, lower alkoxy, trifluoromethyl, amino, —NH(lower alkyl), —NH (cycloalkyl of 3 to 6 carbons), and —N(lower alkyl)$_2$, or one substituent selected from the group consisting of carboxy, —$CO_2$-lower alkyl,

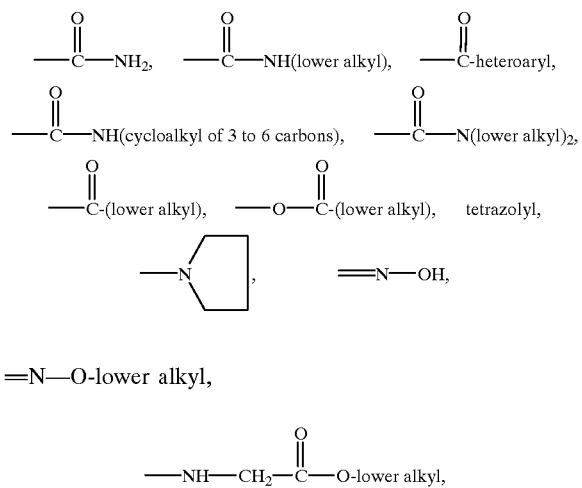

=N—O-lower alkyl,

—NH—$CH_2$—$\overset{O}{\underset{\|}{C}}$—O-lower alkyl, 1,3-dioxolane, and 1,3-dioxane as well as such rings fused to a phenyl ring.

The term "heteroaryl" refers to 5 or 6 membered substituted or unsubstituted monocyclic aromatic rings having one or two O or S atoms and/or one to four N atoms provided that the total number of heteroatoms in the ring is four or less, the nitrogen and sulfur atoms may optionally be oxidized, and the nitrogen atoms may optionally be quaternized. The heteroaryl substituent or substituents are attached to an available carbon atom and are one or two members selected from the group consisting of halo, hydroxy, cyano, lower alkyl, substituted lower alkyl, cycloalkyl of 3 to 6 carbons, lower alkoxy, trifluoromethyl, amino, —NH(lower alkyl), —N(lower alkyl)$_2$, and —NH(cycloalkyl of 3 to 6 carbons), or one substituent selected form the group consisting of carboxy, —$CO_2$-lower alkyl,

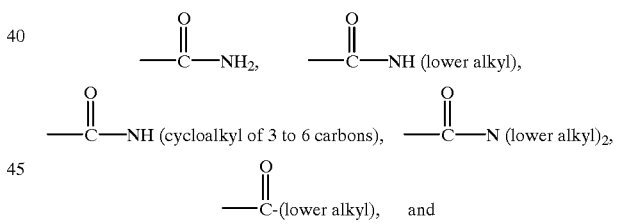

The term "heteroaryl" also refers to substituted or unsubstituted 9 or 10 membered bicyclic rings wherein at least one of the rings is aromatic and wherein at least one of the rings contains one or two O or S atoms and/or one to four N atoms provided that the total number of heteroatoms in either ring is four or less.

The term "substituted cyclohexyl" refers to one or two substituents selected from the group consisting of lower alkyl, lower alkoxy, lower alkylthio, halo, keto, —$(CH_2)_m$-hydroxy, cyano, amino, —NH(lower alkyl), and —N(lower alkyl)$_2$, and/or one substituent selected from the group consisting of carboxy, —$CO_2$-lower alkyl, =N—OH, =N—O-lower alkyl, 1,3-dioxolane, 1,3-dioxane,

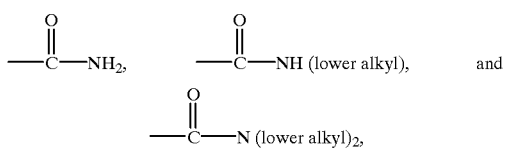 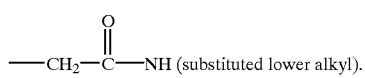

The term "substituted imidazole" refers to an imidazole having one or two substituents selected from the group consisting of lower alkyl, substituted lower alkyl, lower alkoxy, halo, —(CH$_2$)$_m$-hydroxy, cyano, formyl, trifluoromethyl, amino, —NH(lower alkyl), —N(lower alkyl)$_2$, and —NH(cycloalkyl of 3 to 6 carbons), or one substituent selected from the group consisting of carboxy, —CO$_2$-lower alkyl,

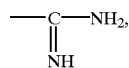

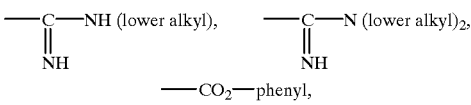

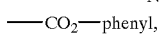

—CO$_2$-(substituted phenyl),

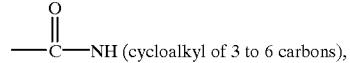

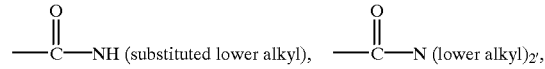

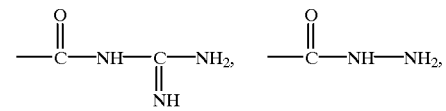

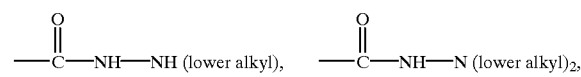

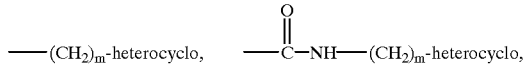

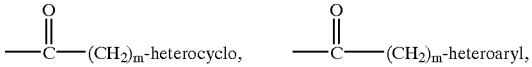

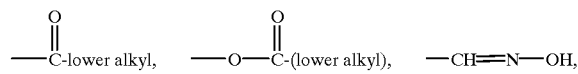

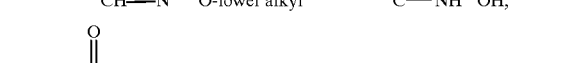

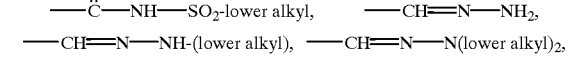

Most preferred are the compounds of formula I and pharmaceutically acceptable salts thereof having the following definitions:

Y is nitrogen.

Z is —C(R$_6$)—.

R$_1$ is —NH(lower alkyl), —N(lower alkyl)$_2$, —NH—(CH$_2$),—OH, —NH—(CH$_2$)$_n$-N(lower alkyl)$_2$, —NH—(CH$_2$)$_n$-substituted phenyl,

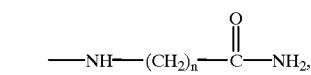

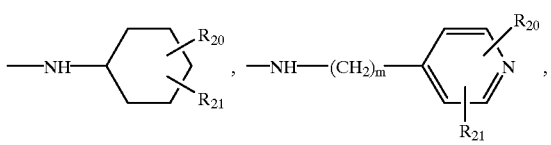

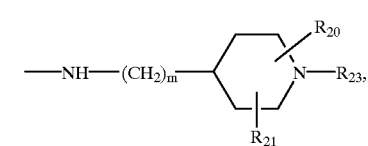

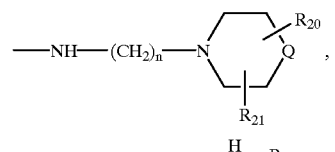

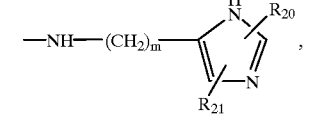

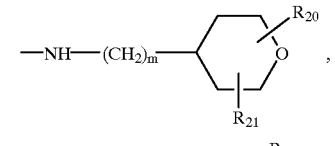

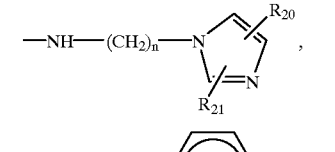

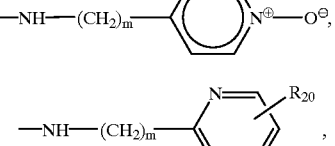

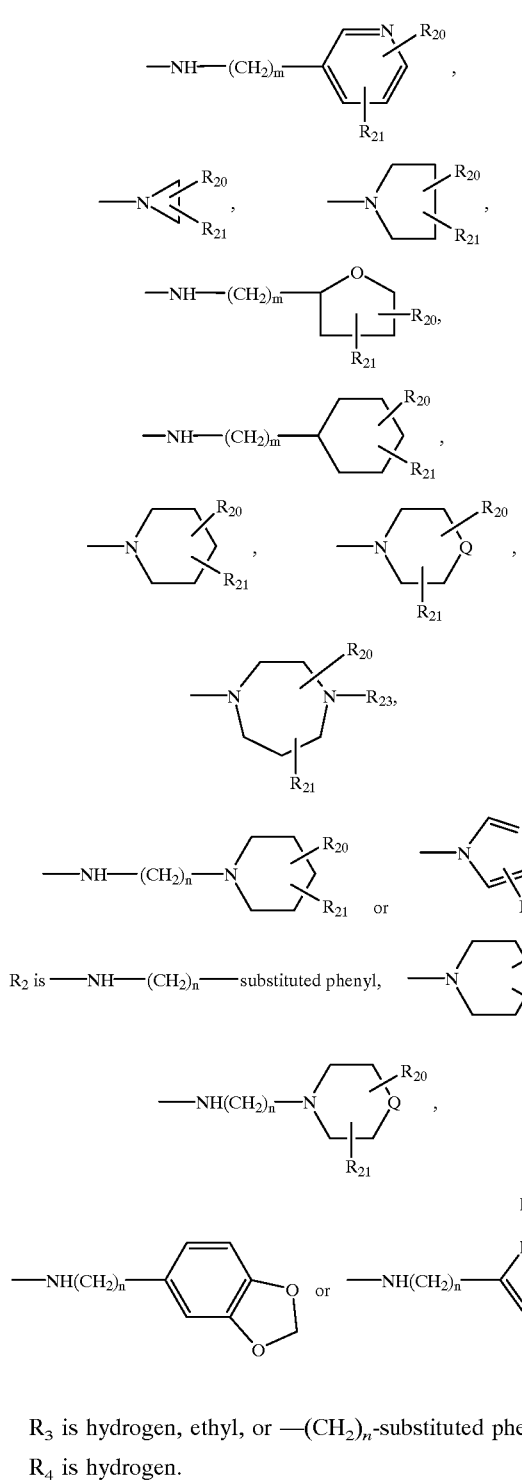
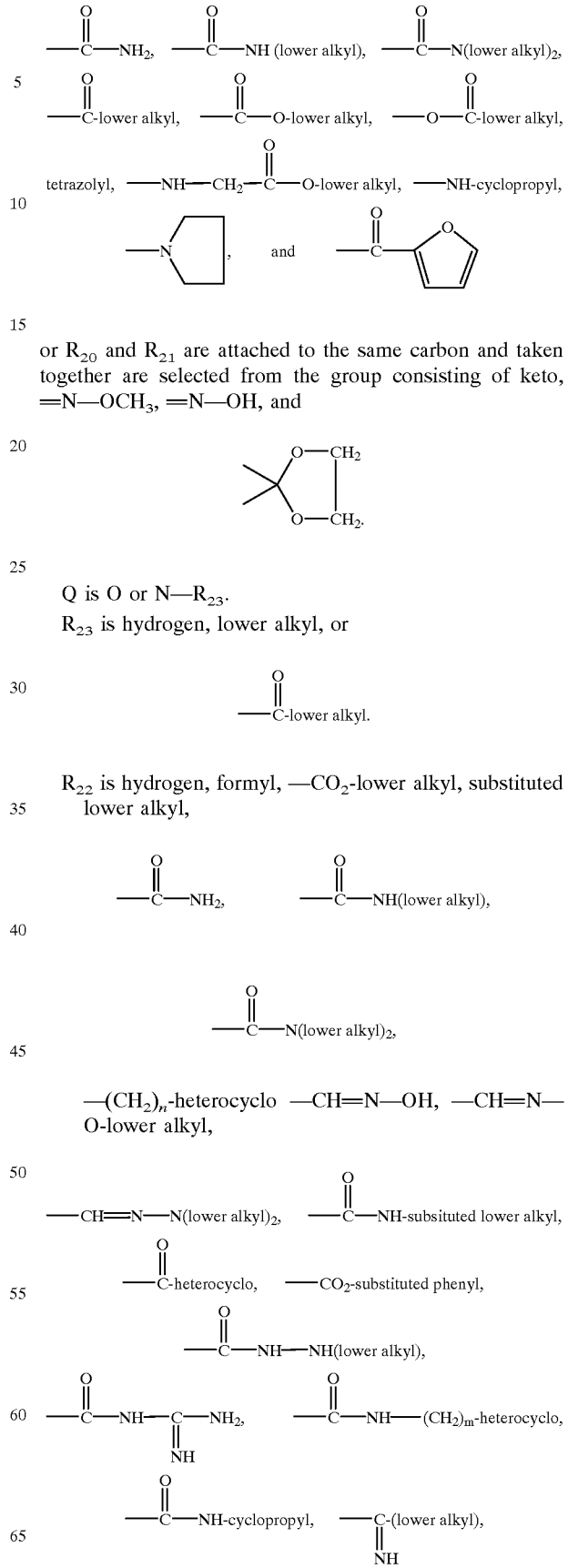

$R_3$ is hydrogen, ethyl, or —$(CH_2)_n$-substituted phenyl.

$R_4$ is hydrogen.

$R_6$ is hydrogen.

m is zero or an integer from 1 to 4.

n is an integer from 1 to 4.

$R_{20}$ and $R_{21}$ are independently selected from hydrogen, lower alkyl, methoxy, chloro, —$(CH_2)_m$-hydroxy, cyano, formyl, cyclopentyl, cyclohexyl, amino, —NH(lower alkyl), and —N(lower alkyl)$_2$, or $R_{21}$ is hydrogen and $R_{20}$ is selected from the group consisting of carboxy, or $R_{20}$ and $R_{21}$ are attached to the same carbon and taken together are selected from the group consisting of keto, =N—OCH$_3$, =N—OH, and Q is O or N—$R_{23}$.

$R_{23}$ is hydrogen, lower alkyl, or $R_{22}$ is hydrogen, formyl, —CO$_2$-lower alkyl, substituted lower alkyl, —$(CH_2)_n$-heterocyclo —CH=N—OH, —CH=N—O-lower alkyl, -continued

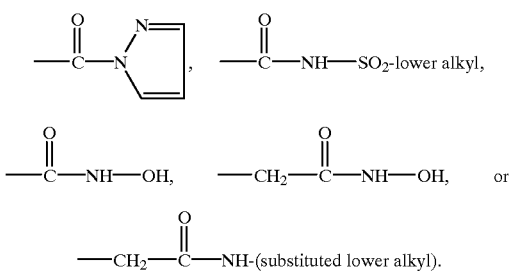

In the most preferred groups the following definitions apply:

The term "substituted phenyl" refers to one or two substituents selected from the group consisting of methoxy, chloro and fluoro as well as pentaflurophenyl.

The term "lower alkyl" refers to straight or branched chain groups of 1 to 4 carbons.

The term "substituted lower alkyl" refers to such lower alkyl groups as defined above having a substituent selected from hydroxy, carboxy, amino, —NH(lower alkyl), —N(lower alkyl)$_2$, —CO$_2$-lower alkyl,

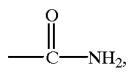

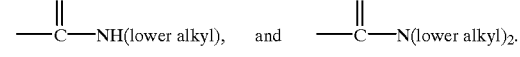

The term heterocyclo refers to the following

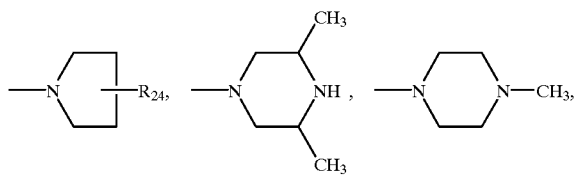

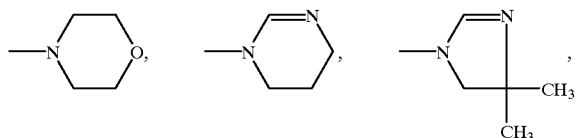

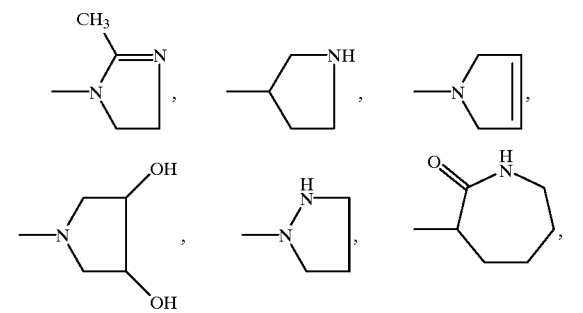

and

-continued

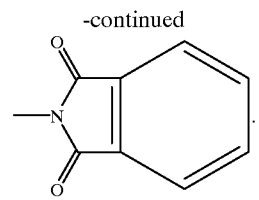

$R_{24}$ is hydrogen, amino, —NH—CO$_2$-lower alkyl, —N(lower alkyl)$_2$, —NH(lower alkyl), methoxymethyl, hydroxy, hydroxymethyl, or

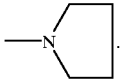

Among the most preferred compounds of this invention the following are of particular interest:

1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide;

1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide, methanesulfonate (1:1);

$N^9$-[(3-chloro-4-methoxyphenyl)methyl]-3-ethyl—$N^6$-(4-pyridinylmethyl)-3H-pyrazolo[4',3':5,6]pyrido[3,4-d]pyridazine-6,9-diamine;

1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-methanol;

1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-(N,N-dimethylethylene) carboxamide;

1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-(N-methylpiperidinyl) carboxamide;

1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-pyrrolidinyl carboxamide;

1-[9-[[(3-chloro-4-methoxyphenyl)methyl]amino]-3-ethyl-3H-pyrazolo[4',3':5,6]pyrido[3,4-d]pyridazin-6-yl]-1H-imidazole-4-[R-1-amino-2-(methoxymethyl)-pyrrolidinyl]hydrazide; and 1-[9-[[(3-chloro-4-methoxyphenyl)methyl]amino]-3-ethyl-3H-pyrazolo[4',3':5,6]pyrido[3,4-d]pyridazin-6-yl]-1H-imidazole-4-acetic acid; especially the first two compounds listed above.

Utility

The compounds of this invention inhibit cGMP PDE, and in particular are potent and selective inhibitors of cGMP PDE V. Thus, these compounds are useful in the treatment of cGMP-associated conditions. A "cGMP-associated condition", as used herein, denotes a disorder which can be treated by inhibiting cGMP PDE or elevating the level of cGMP in a subject, wherein treatment comprises prevention, partial alleviation or cure of the disorder. Inhibition of cGMP PDE or elevation of the cGMP level may occur locally, for example, within certain tissues of the subject, or more extensively throughout the subject being treated for such a disorder. Treatment may be facilitated wherein elevation of the cGMP level potentiates additional beneficial therapeutic effects, such as where elevation of the cGMP level potentiates the effects of endothelium-derived relaxing factor.

The compounds of this invention are useful for the treatment of a variety of cardiovascular diseases including, but not limited to, hypertension, angina (stable, unstable, and variant), (congestive) heart failure, restenosis, atherosclerosis, and dyslipidemia, as well as reduced blood vessel patency, thrombus, both venous and arterial, myocardial infarction, peripheral vascular disease, stroke, bronchitis, chronic asthma, allergic asthma, allergic rhinitis, glaucoma, diseases characterized by disorders of gut motility, diabetes mellitus, benign prostate hyperplasia (BPH), and forms of cancer responsive to the inhibition of cGMP PDE. In addition, these compounds are useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum.

The present invention thus provides methods for the treatment of cGMP-associated conditions, comprising the step of administering to a subject in need thereof at least one compound of the formula I or a salt thereof in an amount effective therefor. Other therapeutic agents such as those described below may be employed in combination with the compounds of formula I in the present methods. In the methods of the present invention, such other therapeutic agent(s) may be administered prior to, simultaneously with or following the administration of the compoundis) of the present invention.

The present invention also provides pharmaceutical compositions comprising at least one of the compounds of the formula I or a salt thereof capable of treating a cGMP-associated condition in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

of formula I may be administered by any suitable means, for example, orally, such as in the form of tablets, capsules, granules or powders; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. These compounds may, for example, be administered in a form suitable for immediate release or extended release. Immediate release or extended release may be achieved by the use of suitable pharmaceutical compositions or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the compound(s) of this invention with fast dissolving diluents such as mannitol, lactose, sucrose and/or cyclodextrins. Also included in such formulations may be high molecular weight excipients such as celluloses (Avicel®) or polyethylene glycols (PEG). Such formulations may also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez®), and agents to control release such as polyacrylic copolymer (e.g., Carbopol 934®). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipients, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase® (mineral oil gelled with polyethylene).

The effective amount of a compound of the present invention may be determined by one of ordinary skill in the art, and includes exemplary dosage amounts for an adult human of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses and the like, subject to cGMP-associated conditions.

The compounds of the present invention may be employed alone or in combination with each other and/or other suitable therapeutic agents useful in the treatment of cGMP-associated conditions such as other cGMP PDE inhibitors, particularly other cGMP PDE V inhibitors, modulators of the large-conductance calcium-activated potassium (BK) channels, prostanoids, α-adrenergic agonists, endothelin antagonists, angiotensin II (especially, subtype $AT_1$) antagonists, angiotensin converting enzyme (ACE) inhibitors, renin inhibitors, and serotonin (5-$HT_{2c}$) agonists.

Exemplary of such other therapeutic agents are the following: phentolamine, yohimbine, papaverine, apomorphine, sildenafil, pyrazolopyrimidinones as described in U.S. Pat. Nos. 5,272,147; 5,250,534; 5,426,107; and 5,346,901, quinazolinones as described in U.S. Pat. No. 5,482,941; $AT_1$ antagonists such as from losartan, irbesartan, valsartan, and candesartan; $ET_A$ antagonists such as bosentan, ABT-627, and those described in U.S. Pat. No. 5,612,359 and U.S. patent application Ser. No. 60/035,832, filed Jan. 30, 1997; PDE V inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), quinazolinones as described in U.S. patent application Ser. No. 60/088,538 filed Jun. 8, 1998, pyridines as described in U.S. patent application Ser. No. 60/100,655 filed Sep. 16, 1998, anthranilic acid derivatives (see WO 95/18097), fused heterocycles (see WO 98/07430) and thienopyrimidines (see DE 19632423); and 5-$HT_{2c}$ agonists selected from indoles (see *J. Med. Chem.*, 40, 2762–2769 (1997), EP 655440 and EP 657426), and modulators of the large-conductance calcium-activated potassium (BK) channels as described in U.S. Pat. Nos. 5,565,483 and 5,602,169, and in WO 98/04135 and WO98/23273.

The above other therapeutic agents, when employed in combination with the compounds of the present invention, may be used, for example, in those amounts indicated in the Physicians' Desk Reference (PDR) or as otherwise determined by one of ordinary skill in the art.

The following assay can be employed in ascertaining the degree of activity of a compound as a cGMP PDE inhibitor. Compounds described in the following Examples have been tested in this assay, and have shown activity.

PDE Scintillation Proximity Assay Protocol

Sonicated human platelet homogenates are prepared by the method of Seiler, et al. (Seiler, S., Gillespie, E., Arnold, A. J., Brassard, C. L., Meanwell, N. A. and Fleming, J. S., "Imidazoquinoline derivatives: potent inhibitors of platelet cAMP phosphodiesterase which elevate cAMP levels and activate protein kinase in platelets," *Thrombosis Research*, 62: 31–42 (1991)). PDE V is abundant in human platelets, and accounts for approximately 90% of the cGMP hydrolytic activity in the homogenates. When necessary, PDE V can be resolved from other PDE activities in the homogenates by anion exchange chromatography on a fast protein liquid chromatography system (FPLC) using a Mono-Q anion exchange column (Pharmacia) eluted with a linear gradient of 10 mM–450 mM NaCl.

The phosphodiesterase activity is assayed using a commercially available phosphodiesterase [³H]cGMP scintillation proximity (SPA) assay kit (Amersham). The manufacturer's protocol is followed explicitly except that the reactions are carried out at room temperature and 3 mM nonradioactive cGMP is included in the suspension of SPA beads to prevent the synthesis of any additional radioactive products.

All documents cited in the present specification are incorporated herein by reference in their entirety.

The following Examples illustrate embodiments of the present invention, and are not intended to limit the scope of the claims.

ABBREVIATIONS

DMF=dimethylformamide
DMSO=dimethylsulfoxide
Et=ethyl
HPLC=high pressure liquid chromatography
LRMS=low resolution mass spectrometry
Me=methyl
MeOH=methanol
mp=melting point
THF=tetrahydrofuran
tlc=thin layer chromatography
rt=room temperature
h=hour(s)
$H_2O$=water
EtOH=ethanol
$H_3PO_4$=phosphoric acid
NaOH=sodium hydroxide
EtOAc=ethyl acetate
<=less than
>=greater than
EDAC.HCl=ethyl-3-(dimethylamino)propyl carbodiimide, hydrochloride salt
HOBT=hydroxybenztriazole
$K_2CO_3$=potassium carbonate

PREPARATION OF STARTING MATERIALS

PREPARATION 1

(1-Ethylpyrazol-5-ylamino)methylenemalonate diethyl ester

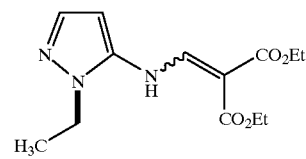

A neat solution of 5-amino-1-ethylpyrazole (20.0 g, 180 mmol) and diethyl ethoxymethylenemalonate (42.8 g, 198 mmol) was heated at 120° C. for 5 h. This material was used directly without further purification. If needed, the product can be distilled at 154–160° C. (0.1 mm Hg) to afford the title compound as a liquid which solidified to afford the title compound as a pale colored solid: mp 50–53° C.

PREPARATION 2

1-Ethyl-4-hydroxy-1H-pyrazolo[3,4-b]pyridine-5-carboxylic acid, ethyl ester

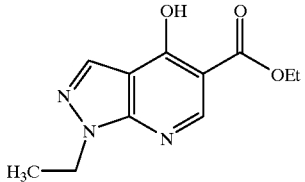

(1-Ethylpyrazol-5-ylamino)methylenemalonate diethyl ester (180 mmol from previous reaction) was dissolved in diphenyl ether (200 mL), and the resulting solution was placed in a preheated oil bath at 255° C. The reaction solution was heated for 5 h, and then the diphenyl ether was removed via distillation. The resulting brown reaction mixture was cooled to room temperature and poured into hexane (1 L). This solution was cooled to −78° C., and the resulting precipitate was filtered to afforded the title compound as a beige colored needle shaped solid that was >90% pure by HPLC and was used directly (25 g, 60% for 2 steps). A portion was recrystallized using ethanol-H$_2$O to afford a white solid: mp 85–86° C.; LRMS (m/z) 236 (MH$^+$).

PREPARATION 3

4-Chloro-1-ethyl-1H-pyrazolo[3,4-b]pyridine-5-carboxylic acid, ethyl ester

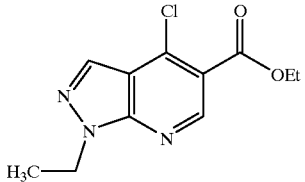

1-Ethyl-4-hydroxy-1H-pyrazolo[3,4-b]pyridine-5-carboxylic acid, ethyl ester (15 g, 63.8 mmol) was dissolved in phosphorus oxychloride (100 mL), and the resulting solution was heated at reflux for 4 h. The remaining phosphorus oxychloride was removed via evaporation under reduced pressure. The residual light brown solid was recrystallized from EtOH-hexane to afford the title compound as a white solid (14 g, 55.3 mmol, 87%): HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.84 minutes showed a purity of 96%; LRMS (m/z) 254 (MH$^+$).

PREPARATION 4

4-Chloro-1-ethyl-1H-pyrazolo[3,4-b]pyridine-5-carboxylic acid, ethyl ester

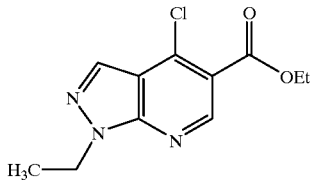

(1-Ethylpyrazol-5-ylamino)methylenemalonate diethyl ester (10.0 g, 42.6 mmol) was dissolved in phosphorus oxychloride (50 mL). This solution was heated at reflux for 10 h before the phosphorus oxychloride was removed via evaporation under reduced pressure. The resulting brown residue was diluted with EtOH (5 mL) and extracted with hot hexane (200 mL×3). The combined organic layers were evaporated under reduced pressure to afford the title compound as an oil which formed light green needle shaped crystals upon standing at room temperature (5.4 g, 21.3 mmol, 50% yield). This material is identical to the one obtained in Preparation 3 ($^1$H NMR, $^{13}$C, MS, and HPLC).

PREPARATION 5

(3-Chloro-4-methoxyphenyl)methylamine, hydrogen chloride

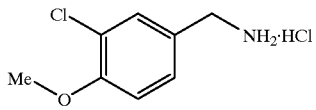

Method A. (4-Methoxyphenyl)methylamine (75.0 g, 0.55 mol) was dissolved in diethyl ether (400 mL). Hydrogen chloride (4.0 M in dioxane, 1.1 mol) was added dropwise with vigorous stirring. After the addition was completed, the resulting hydrochloride salt was filtered and washed thoroughly with diethyl ether. The salt was air dried over night (95.0 g, 100%).

Chlorine gas was bubbled into glacial acetic acid (400 mL) with stirring until the chlorine content in the acetic acid represented 7% of the original weight of the acetic acid. In a 2 L round bottom flask, 4-methoxybenzylamine hydrogen chloride (32.0 g, 0.18 mol) was suspended in glacial acetic acid (400 mL) with vigorous stirring. The chlorine solution (1.5 eq Cl$_2$) was added dropwise rapidly over 30 min at room temperature. The resulting suspension was stirred for another 20 min before nitrogen was bubbled through the reaction solution to remove chlorine and HCl (using a 6 N NaOH trap). The acetic acid was evaporated under reduced pressure to a 100 mL volume. To this white slurry, diethyl ether (300 mL) was added, and the resulting solid was filtered. This solid was resuspended with 50 mL acetic acid followed by the addition of 50 mL diethyl ether and then filtered again. This process was repeated twice. The white solid was then transferred to a 1 L Erhlenmeyer flask and suspended in THF (400 mL). This suspension was heated at reflux for 10 min before filtration. The undissolved solid was then filtered, and twice resuspended in boiling THF (100 mL) with filtration to afford the title compound (27.0 g, 71%) as a white solid. This material contained <2% starting material and <2% dichlorinated material.

Method B. In a 5 L three-necked round-bottomed flask equipped with a mechanical stirrer, thermometer, dropping funnel and argon inlet was placed 4-methoxybenzylamine (105.5 g, 0.770 mol), and then acetic acid (1000 mL) was added under argon atmosphere with ice cooling to keep the temperature at around 20° C. Sulfuryl chloride (92.7 mL, 1.16 mol) was then added over 20 min with vigorous stirring while the temperature was maintained below 25° C. The cooling bath was then removed and the resulting mixture (slurry) was stirred at room temperature for 5 h. The reaction mixture was diluted with diethyl ether (1500 mL) and stirred at room temperature for 1 h. The resulting white crystalline solid was collected by filtration, washed with ether (1000 mL), dried in vacuum oven (40° C.) for 18 h to afford the title compound (93.2 g, 70% yield) as a white solid. HPLC showed 97.9 area % of desired product, 1.8% of starting material and 0.3% of bischlorinated benzylamine.

PREPARATION 6

4-Cyano-1-ethyl-1H-pyrazolo[3,4-b]pyridine-5-carboxylic acid, ethyl ester

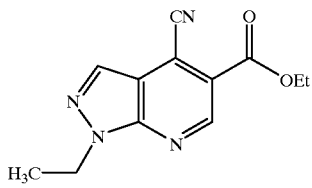

To a solution of 4-chloro-1-ethyl-1H-pyrazolo[3,4-b]pyridine-5-carboxylic acid, ethyl ester (10.0 g, 39.5 mmol) in DMF (50 mL) and ethanol (10 mL) was added either sodium cyanide (3.9 g, 80.0 mmol) or tetrabutylarimonium cyanide (11.8 g, 1.1 eq) or tetrabutylammonium chloride (14.7 g, 1.0 eq) and sodium cyanide (2.4 g, 1.2 eq) together. This solution or suspension was warmed up to 60° C. until reaction was completed as judged by TLC. The reaction mixture was then diluted with water (200 mL) and stirred gently at rt for 10 min. A large amount of precipitate formed. The solid was filtered and rinsed thoroughly with water to afford the title compound as an off-white solid after drying: 40–80% yield. This material was >95% pure as judged by HPLC and was used directly without further purification.

PREPARATION 7

1-Ethyl-1H-pyrazolo[3,4-b]pyridine-4,5-dicarboxylic acid

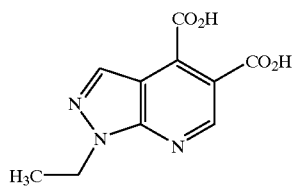

4-Cyano-1-ethyl-1H-pyrazolo[3,4-b]pyridine-5-carboxylic acid, ethyl ester (2.0 g, 8.2 mmol) was suspended in ethanol (20 mL), and an aqueous solution of NaOH (6 N, 3 eq) was added. The reaction mixture was heated at reflux for 2 h and then diluted with water (100 mL). This aqueous solution was extracted with diethyl ether (50 mL×2) and the organic extracts were discarded. The aqueous layer was then acidified with phosphoric acid and extracted with EtOAc (50 mL×3). The extracts were concentrated via evaporation under reduced pressure to afford the title compound (>90% purity, 50–90% yield). This material was used directly without further purification.

PREPARATION 8

9-Amino-3-ethyl-3H-pyrazolo[4',3':5,6]pyrido[3,4-d]pyridazin-6(7H)-one

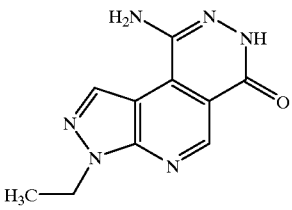

To a suspension of 4-cyano-1-ethyl-1H-pyrazolo[3,4-b]pyridine-5-carboxylic acid, ethyl ester (10.0 g, 40.1 mmol) in ethanol (100 mL) was added anhydrous hydrazine (5 eq). This suspension was then heated at 80° C. until starting material was consumed. The reaction was allowed to cool to rt and diluted with water (200 mL). The resulting solid was filtered and washed thoroughly with water until the filtrate was colorless. The solid was dried under vacuum to afford the title compound as a yellow solid (5.5 g, 60%). This material was >90% pure as judged by HPLC and was used directly.

PREPARATION 9

3-Ethyl-7,8-dihydro-3H-pyrazolo[4',3':5,6]pyrido[3,4-d]pyridazine-6,9-dione

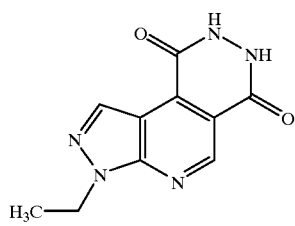

To a suspension of 9-amino-3-ethyl-3H-pyrazolo[4',3':5,6]pyrido[3,4-d]pyridazin-6(7H)-one (5.0 g, 21.7 mmol) and sodium nitrite (15.0 g, 10 eq) in water (200 mL) was added concentrated sulfuric acid until the pH was <2. The suspension was stirred vigorously and some nitric oxide—nitrogen dioxide was evolved. This suspension was then placed on a hot plate and heated to boiling. The pH of the reaction was maintained at pH>2 with the addition of sulfuric acid as necessary. When the reaction was judged complete by HPLC, the resulting reaction mixture was cooled to rt. The precipitated white solid was collected by filtration, washed with water thoroughly and dried under vacuum to afford the title compound as an off white solid (4.6 g, 92%, purity >95% as judged by HPLC).

An alternative method could be used by starting with 1-ethyl-1H-pyrazolo[3,4-b]pyridine-4,5-dicarboxylic acid. The diacid was dissolved in anhydrous THF with EDAC.HCl (1.2 eq), HOBT (1.2 eq), and triethylamine (5.0 eq). To this solution was added anhydrous hydrazine (2.0 eq). The resulting solution was stirred at rt for 5 h and then diluted with water. The precipitated solid was collected by filtration to afford the title compound as a white solid.

PREPARATION 10

6,9-Dichloro-3-ethyl-3H-pyrazolo[4',3':5,6]pyrido[3,4-d]pyridazine

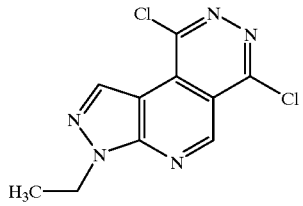

3-Ethyl-7,8-dihydro-3H-pyrazolo[4',3':5,6]pyrido-[3,4-d]pyridazine-6,9-dione (5.0 g, 21.6 mmol) was suspended in phosphorus oxychloride (30 mL), and the resulting mixture was heated at reflux for 3 h. The excess phosphorus oxychloride was removed via evaporation under reduced pressure. The brown residue was dissolved in EtOAc (100 mL), and the resulting mixture was poured onto ice (100 g) with stirring. The organic layer was separated and washed thoroughly with water (100 mL×3). The organic layer was then dried over sodium sulfate, and the solvent was removed via evaporation under reduced pressure to afford the title compound as a pale white solid (5.5 g, 95% yield with a purity >90% as judged by HPLC).

The above compound was also prepared by the following procedure.

To a slurry of 3-Ethyl-7,8-dihydro-3H-pyrazolo[4', 3':5,6]pyrido[3,4-d]pyridazine-6,9-dione (20 g, 0.087 mol) in toluene was added pyridine (14 ml, 0.17 mol) and phosphorus oxychloride (17.7 ml, 0.19 mol) at room temperature. The slurry was stirred at room temperature for 20 minutes and at 80–85° C. for 10 hours. After cooling the reaction mixture the solids were filtered and washed with toluene. Water was added to the filtrate and the pH was adjusted from 1–2 to pH 10–11. The organic layer was separated and dried over magnesium sulfate. After removal of the solvent under reduced pressure the product was obtained as a light yellow solid. Yield 18.8 g (81%), HPLC AP>99%.

EXAMPLE 1

1-(9-Chloro-3-ethyl-3H-pyrazolo[4',3':5,6]pyrido[3,4-d]pyridazin-6-yl)-4-piperidinol

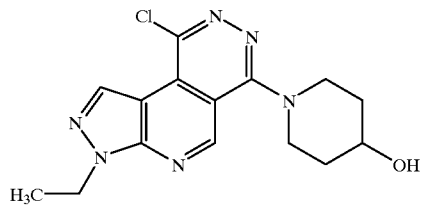

To a suspension of 6,9-dichloro-3-ethyl-3H-pyrazolo[4',3':5,6]pyrido[3,4-d]pyridazine (3.2 g, 12.0 mmol) in THF/ethanol (40 mL, 1:1) in a 100 mL pressure tube was added triethylamine (5 eq) and 4-hydroxy-piperidine (1.1 eq) sequentially. The reaction mixture was heated in an oil bath at 60° C. for 2 h. The progress of the reaction was monitored by HPLC. The reaction mixture was transferred to a 200 mL round-bottomed flask, and the solvent was removed via evaporation under reduced pressure. The light brown residue was resuspended in saturated sodium bicarbonate (100 mL), and the precipitated solid was collected by filtration. This orange solid was washed thoroughly with water and dried in a vacuum oven at 40° C. over night to afford the title compound (3.2 g, 80% yield). This material was >93% pure and was used directly without further purification.

EXAMPLE 2

1-[9-[[(3-Chloro-4-methoxyphenyl)methyl]amino]-3-ethyl-3H-pyrazolo[4',3':5,6]pyrido[3,4-d]pyridazin-6-yl]-4-piperidinol

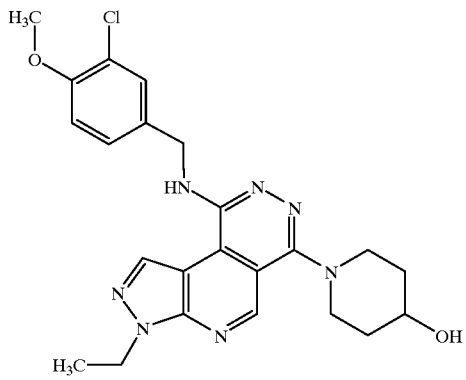

1-(9-Chloro-3-ethyl-3H-pyrazolo-[4',3':5,6]pyrido-[3,4-d]pyridazin-6-yl)-4-piperidinol (2.4 g, 7.2 mmol) and (3-chloro-4-methoxyphenyl)methylamine hydrogen chloride (7.5 g, 5 eq) were suspended in N-methylpyrrolidinone (20 mL) and diisopropylethylamine (5 eq) in a 100 mL pressure tube. The reaction tube was submerged in a preheated oil bath at 170° C. for 2 h. HPLC analysis showed complete consumption of starting material. The reaction was cooled to rt and diluted with EtOAc (250 mL). This solution was washed consecutively with water (200 mL×3) and brine (200 mL×2) and dried over sodium sulfate. The solvent was removed via evaporation under reduced pressure to afford a brown foam. Column chromatography of this foam using silica gel and dichloromethane-methanol (30:1) afforded the title compound as an orange solid (2.0 g, 60%): mp 109–110.5° C. The material was analyzed by HPLC and showed 95% purity: HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.22 minutes; LRMS (m/z) 468 ($MH^+$).

EXAMPLE 3

General Procedure for the Preparation of 9-Chloro-6-substituted Pyrazolopyridopyridazines

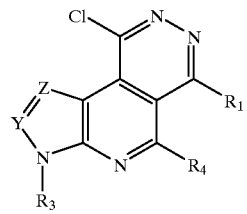

To a suspension of the appropriate 6,9-dichloropyrazolopyridopyridazine in THF-ethanol (1:1) (final concentration: ~200 mM) in a 100 mL pressure tube was added triethylamine (5 eq) followed by the appropriate amine, alcohol or thiol ($R_1XH$). The reaction mixture was heated in an oil bath at 60° C.–100° C. until the reaction was complete as judged by TLC or HPLC. The reaction mixture was then transferred to a 200 mL round-bottomed flask and the solvent was removed via evaporation under reduced pressure. The residue was resuspended in saturated $NaHCO_3$ (100 mL), and the precipitated solid was collected by filtration. The collected solid was washed thoroughly with water and dried in a vacuum oven at 40° C. over night. If the material was >85% purity, it was used directly without purification, otherwise purification using silica gel chromatography was performed.

EXAMPLE 4

General Procedure for the Preparation of 6,9-Disubstituted Pyrazolopyridopyridazine

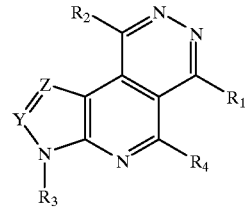

The appropriate 9-chloro-6-substituted pyrazolopyridopyridazine and the appropriate amine, alcohol or thiol ($R_2AH$, 5 eq) were suspended in N-methylpyrrolidinone (to make a final concentration ~200 mM) along with diisopropylethylamine (5 eq) in a 100 mL pressure tube. The reaction tube was submerged in a preheated oil bath at 170° C. until reaction was completed as judged by HPLC. The reaction was cooled to rt and diluted with EtOAc. This solution was washed consecutively with water and brine and dried over $Na_2SO_4$. The solvent was removed under via evaporation reduced pressure to afford a brown foam. Column chromatography using silica gel and $CH_2Cl_2$—$CH_3OH$ (30:1) afforded the title compound.

The compounds listed below in Table 1 were prepared using the general procedures contained in Example 3 and Example 4 described above.

TABLE 1

| NUMBER | NAME | STRUCTURE | PURITY (%) | HLPC (retention time, minutes) | OTHER DATA |
|---|---|---|---|---|---|
| 1 | $N^9$-[(3-Chloro-4-methoxyphenyl)-methyl]-3-ethyl-$N^6$(4-pyridinyl-methyl)-3H-pyrazolo[4',3':5,6]-pyrido[3,4-d]pyridazine-6,9-diamine | 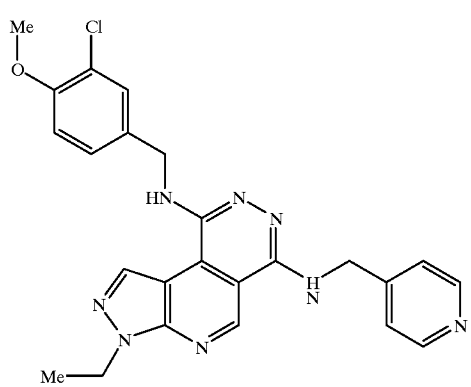 | 97 | 2.66 | m/z (M + H) 475 mp: 150–152° C. |

TABLE 1-continued

| NUMBER | NAME | STRUCTURE | PURITY (%) | HLPC (retention time, minutes) | OTHER DATA |
|---|---|---|---|---|---|
| 2 | 1-[9-[[(3-Chloro-4-methoxyphenyl)-methyl]amino]-3-ethyl-3H-pyrazolo[4',3':5,6]pyrido[3,4-d]pyridazin-6-yl]-4-piperidine-carboxylic acid | 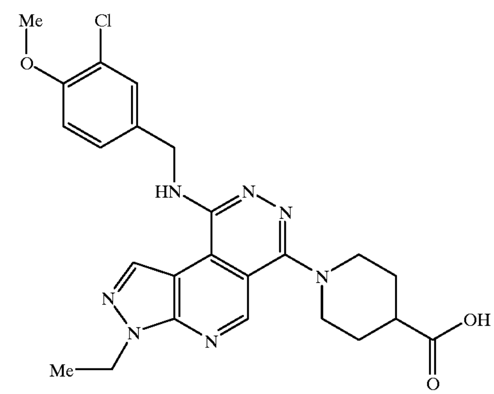 | 95 | 3.49 | m/z (M + H) 496 |
| 3 | 1-[9-[[(3-Chloro-4-methoxyphenyl)-methyl]amino]-3-ethyl-3H-pyrazolo[4',3':5,6]pyrido[3,4-d]pyridazin-6-yl]-4-piperidine-carboxamide | 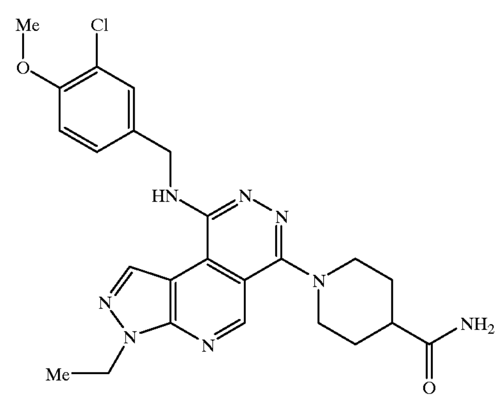 | 97 | 3.12 | m/z (M + H) 495 |
| 4 | 1-[9-[[(3-Chloro-4-methoxyphenyl)-methyl]amino]-3-ethyl-3H-pyrazolo[4',3':5,6]pyrido[3,4-d]pyridazin-6-yl]-N-methyl-4-piperidinecarbox-amide | 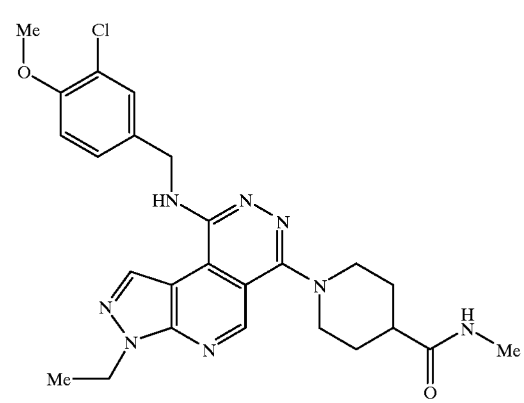 | 90 | 3.65 | m/z (M + H) 441 |

TABLE 1-continued

| NUMBER | NAME | STRUCTURE | PURITY (%) | HLPC (retention time, minutes) | OTHER DATA |
|---|---|---|---|---|---|
| 5 | 1-[9-[[(3-Chloro 4-methoxyphenyl) methyl]amino]-3-ethyl-3H-pyrazolo[4',3':5,6]pyrido[3,4-d]pyridazin-6-yl]-N,N-dimethyl-4-piperidinecarbox-amide | 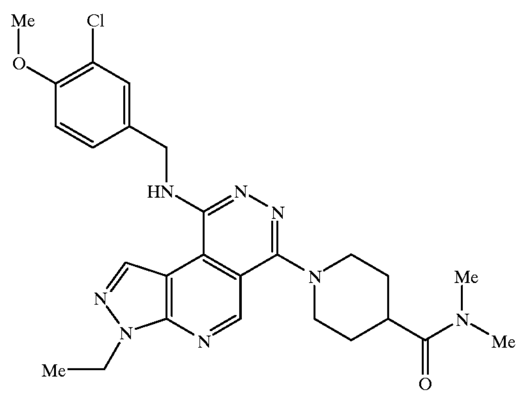 | 97 | 3.81 | m/z (M + H) 452 |
| 6 | 1-[9-[[(3-Chloro-4-methoxyphenyl)-methyl]amino]-3-ethyl-3H-pyrazolo[4',3':5,6]pyrido[3,4-d]pyridazin-6-yl]-4-piperidine-methanol | 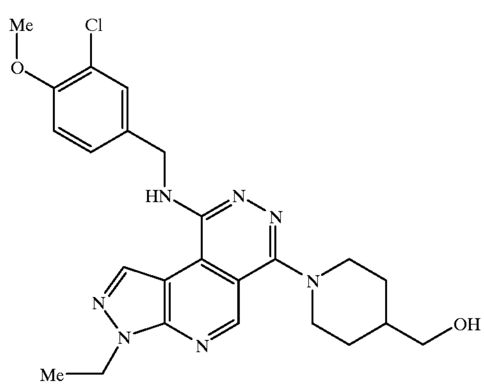 | 98 | 3.44 | m/z (M + H) 482 |
| 7 | 1-[9-[[(3-Chloro-4-methoxyphenyl) methyl]amino]-3-ethyl-3H-pyrazolo[4',3':5,6]pyrido[3,4-d]pyridazin-6-yl]-4-piperidine-carboxylic acid, ethyl ester | 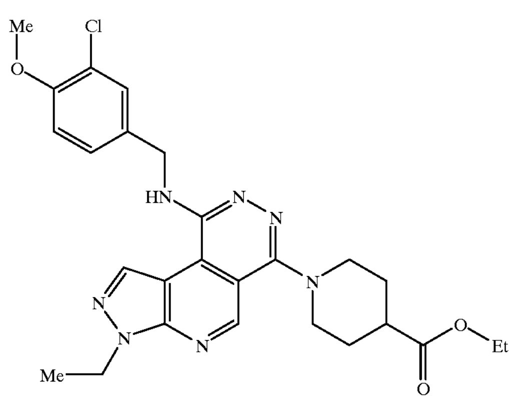 | 93 | 3.76 | m/z (M + H) 524 |

TABLE 1-continued

| NUMBER | NAME | STRUCTURE | PURITY (%) | HLPC (retention time, minutes) | OTHER DATA |
|---|---|---|---|---|---|
| 8 | N-[(3-Chloro-4-methoxyphenyl)methyl]-3-ethyl-6-(4-methyl-1-piperazinyl)-3H-pyrazolo[4',3':5,6]pyrido[3,4-d]pyridazin-9-amine | 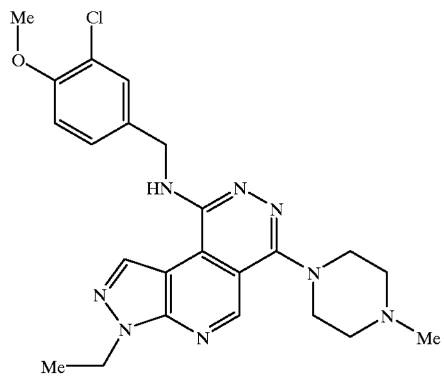 | 83 | 2.72 | m/z (M + H) 467 |
| 9 | 3-[[9-[[(3-Chloro-4-methoxyphenyl)-methyl]amino]-3-ethyl-3H-pyrazolo[4',3':5,6]pyrido[3,4-d]pyridazin-6-yl]amino]-1-propanol | 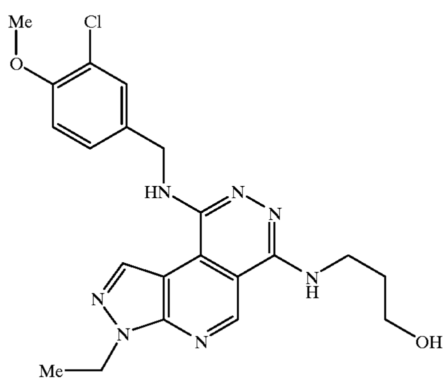 | 93 | 3.34 | m/z (M + H) 442 |
| 10 | N-[(3-Chloro-4-methoxyphenyl)-methyl]-3-ethyl-6-(4-morpholinyl)-3H-pyrazolo-[4',3':5,6]pyrido-[3,4-d]pyridazin-9-amine | 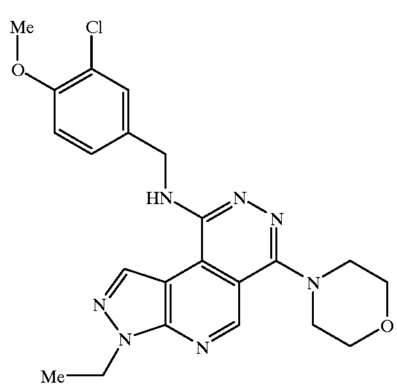 | 93 | 3.44 | m/z (M + H) 475 |

TABLE 1-continued

| NUMBER | NAME | STRUCTURE | PURITY (%) | HLPC (retention time, minutes) | OTHER DATA |
|---|---|---|---|---|---|
| 11 | 1-[9-[[(3-Chloro-4-methoxy-phenyl)methyl]-amino]-3-ethyl-3H-pyrazolo[4',3':5,6]pyrido[3,4-d]pyridazin-6-yl]-4-piperidine-carbonitrile | 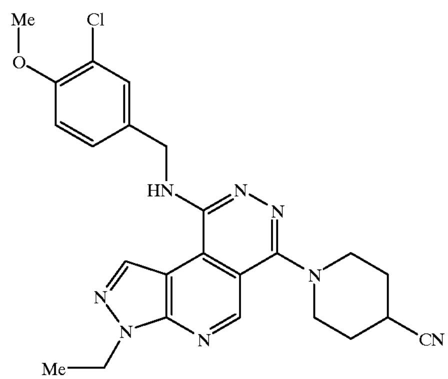 | 90 | 3.45 | m/z (M + H) 477 |
| 12 | N-[(3-Chloro-4-methoxyphenyl)-methyl]-3-ethyl-6-[4-(1H-tetrazol-5-yl)-1-piperidinyl]-3H-pyrazolo[4',3':5,6]-pyrido[3,4-d]pyridazin-9-amine | 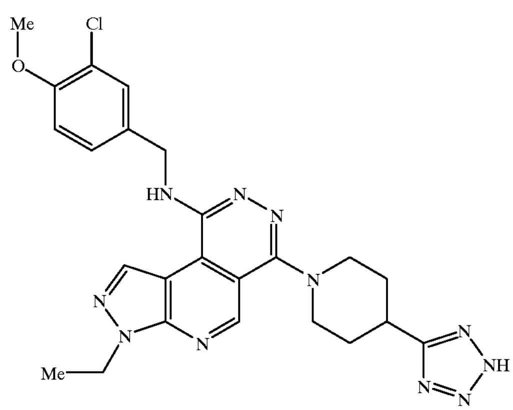 | 92 | 3.36 | m/z (M + H) 520 |
| 13 | 1-[9-[[(3-Chloro-4-methoxyphenyl)-methyl]amino]-3-ethyl-3H-pyrazolo[4',3':5,6]pyrido[3,4-d]pyridazin-6-yl]-4-piperidinone | 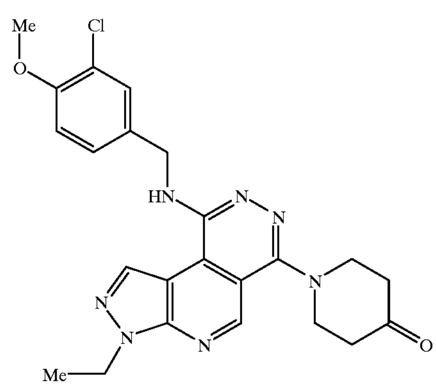 | 92 | 3.32 | m/z (M + H) 466 |

TABLE 1-continued

| NUMBER | NAME | STRUCTURE | PURITY (%) | HLPC (retention time, minutes) | OTHER DATA |
|---|---|---|---|---|---|
| 14 | N$^6$,N$^9$-Bis[(3-chloro-4-methoxyphenyl)-methyl]-3-ethyl-3H-pyrazolo-[4',3':5,6]pyrido-[3,4-d]pyridazine-6,9-diamine | 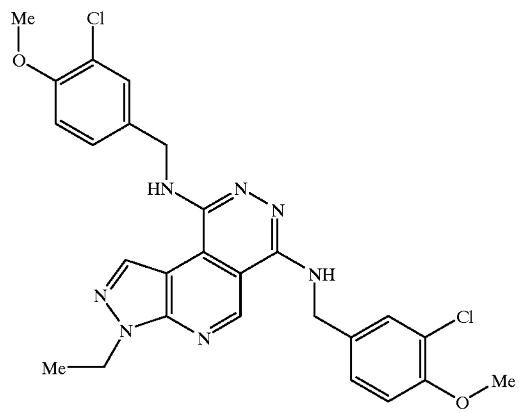 | 87 | 3.85 | m/z (M + H) 539 |
| 15 | 1-[3-Ethyl-9-[[(4-methoxyphenyl)-methyl]amino]-3H-pyrazolo[4',3':5,6]pyrido [3,4-d]pyridazin-6-yl]-4-piperidinol | 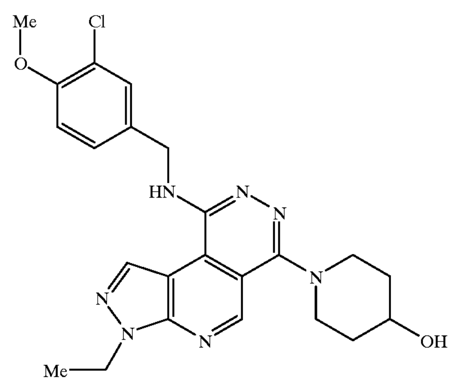 | 99 | 3.2 | m/z (M + H) 434 |
| 16 | 1-[3-Ethyl-9-[[(4-fluorophenyl)-methyl]amino]-3H-pyrazolo[4',3':5,6]pyrido[3,4-d]pyridazin-6-yl]-4-piperidinol | 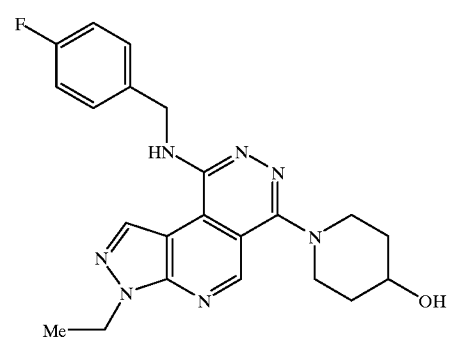 | 96 | 3.20 | m/z (M + H) 422 |
| 17 | 1-[3-Ethyl-9-[(1,3-benzodioxol-5-ylmethyl)amino]-3H-pyrazolo-[4',3':5,6]pyrido-[3,4-d]pyridazin-6-yl]-4-piperidinol (BMS-302946) | 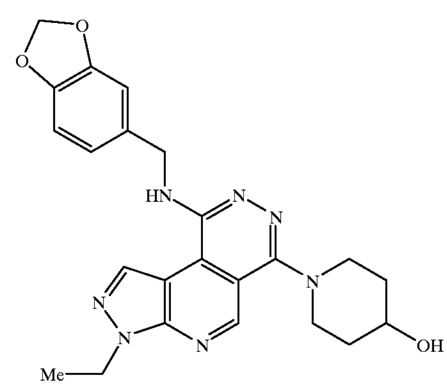 | 96 | 3.10 | m/z (M + H) 448 |

TABLE 1-continued

| NUMBER | NAME | STRUCTURE | PURITY (%) | HLPC (retention time, minutes) | OTHER DATA |
|---|---|---|---|---|---|
| 18 | 1-[3-Ethyl-9-[[2-(4-morpholinyl)ethyl]amino]-3H-pyrazolo[4',3':5,6]pyrido[3,4-d]pyridazin-6-yl]-4-piperidinol | 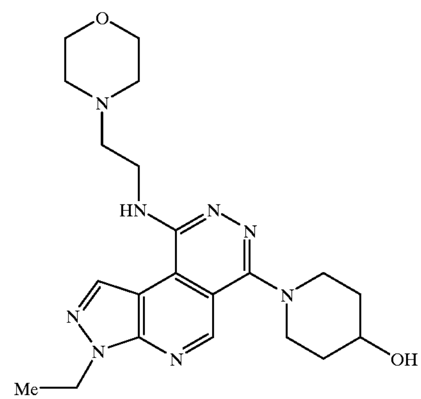 | 97 | 1.60 | m/z (M + H) 427 |
| 19 | 1-[3-Ethyl-9-[[2-(1H-imidazol-4-yl)ethyl]amino]-3H-pyrazolo-[4',3':5,6]pyrido-[3,4-d]pyridazin-6-yl]-4-piperidinol | 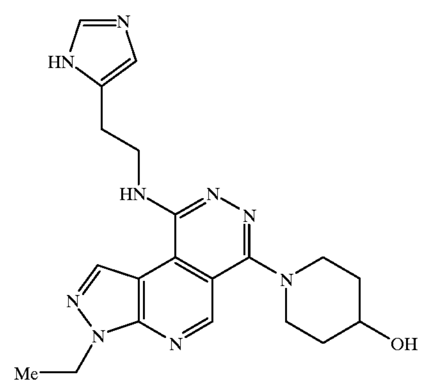 | 95 | 1.85 | m/z (M + H) 408 |
| 20 | (R)-1-[9-[((3-Chloro-4-methoxyphenyl)-methyl]amino]-3-ethyl-3H-pyrazolo-[4',3':5,6]pyrido-[3,4-d]pyridazin-6-yl]-2-pyrrolidinecarboxylic acid, t-butyl ester | 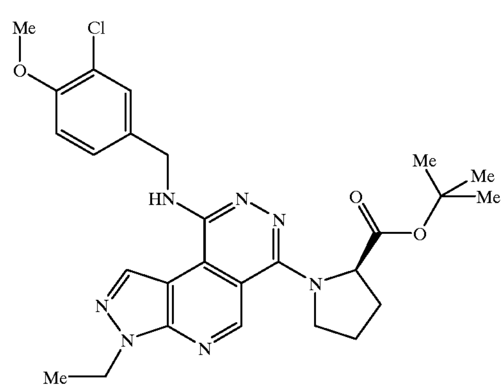 | 95 | 3.82 | m/z (M + H) 539 |

TABLE 1-continued

| NUMBER | NAME | STRUCTURE | PURITY (%) | HLPC (retention time, minutes) | OTHER DATA |
|---|---|---|---|---|---|
| 21 | (S)-1-[[9-[[(3-Chloro-4-methoxyphenyl)-methyl]amino)-3-ethyl-3H-pyrazolo-[4',3':5,6]pyrido-[3,4-d]pyridazin-6-yl]-2-pyrrolidinecar-boxylic acid, t-butyl ester | 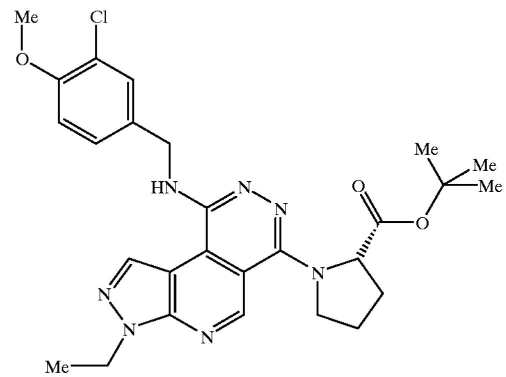 | 95 | 3.76 | m/z (M + H) 539 |
| 22 | (+)-1-[[9-[[(3-Chloro-4-methoxyphenyl)-methyl]amino]-3-ethyl-3H-pyrazolo-[4',3':5,6]pyrido-[3,4-d]pyridazin-6-yl]-3-piperidine-carboxylic acid, ethyl ester | 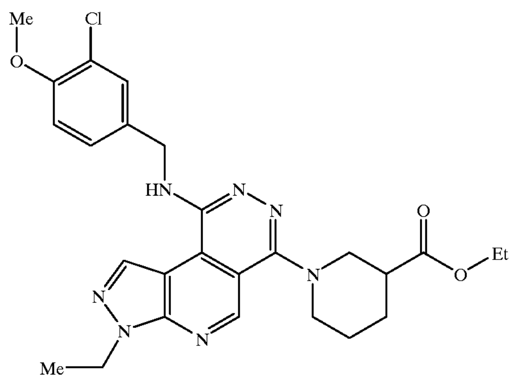 | 95 | 3.86 | m/z (M + H) 525 |
| 23 | (−)-1-[[9-[[(3-Chloro-4-methoxyphenyl)-methyl]amino]-3-ethyl-3H-pyrazolo-[4',3':5,6]pyrido-[3,4-d]pyridazin-6-yl]-3-piperidine-carboxylic acid, ethyl ester | 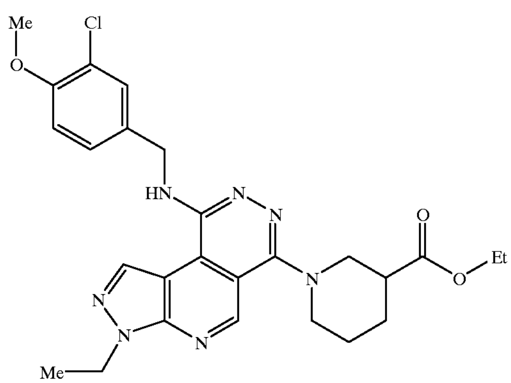 | 95 | 4.24 | m/z (M + H) 525 |
| 24 | 1,1'-(3-Ethyl-3H-pyrazolo[4',3':5,6]pyrido[3,4-d]pyridazin-6,9-diyl)bis[4-piperidinol] | 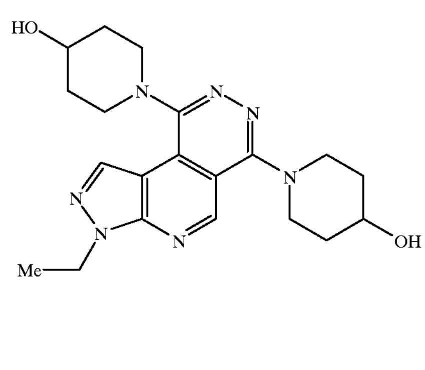 | 94 | 2.53 | m/z (M + H) 398 |

TABLE 1-continued

| NUMBER | NAME | STRUCTURE | PURITY (%) | HLPC (retention time, minutes) | OTHER DATA |
|---|---|---|---|---|---|
| 25 | (R)-1-[9-[[(3-Chloro-4-methoxyphenyl)-methyl]amino]-3-ethyl-3H-pyrazolo-[4',3':5,6]pyrido-[3,4-d]pyridazin-6-yl]-3-(dimethylamino)-pyrrolidine | 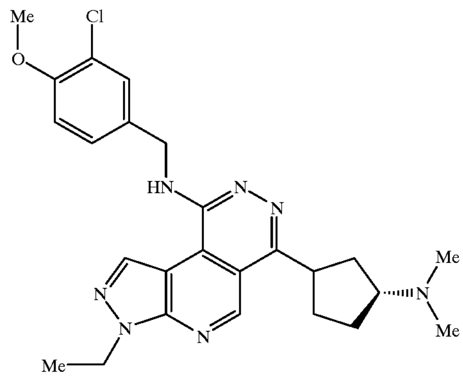 | 91 | 2.54 | m/z (M + H) 481 |
| 26 | 1-[9-[[(3-Chloro-4-methoxyphenyl)-methyl]amino]-3-ethyl-3H-pyrazolo-[4',3':5,6]pyrido-[3,4-d]pyridazin-6-yl]-3-hydroxypyrrolidine | 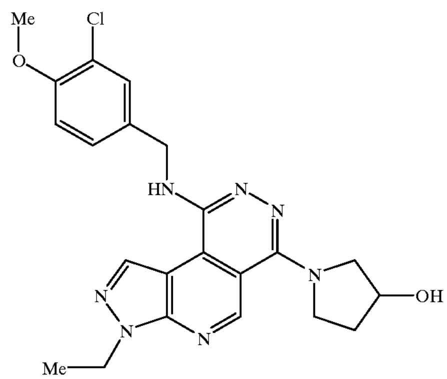 | 89 | 3.11 | m/z (M + H) 454 |
| 27 | N$^9$-[(3-Chloro-4-methoxyphenyl)-methyl]-3-ethyl-N$^6$-[(4-pyridinyl-1-oxide)methyl]-3H-pyrazolo-[4',3':5,6]pyrido-[3,4-d]pyridazine-6,9-diamine | 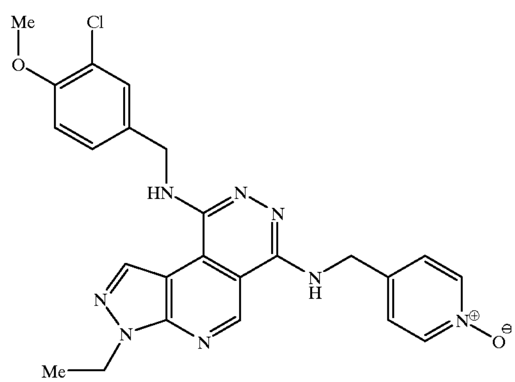 | 88 | 3.03 | m/z (M + H) 491 |
| 28 | 1-[6-[[(3-Chloro-4-methoxyphenyl)-methyl]amino]-3-ethyl-3H-pyrazolo-[4',3':5,6]pyrido-[3,4-d]pyridazin-9-yl]-4-piperidinol | 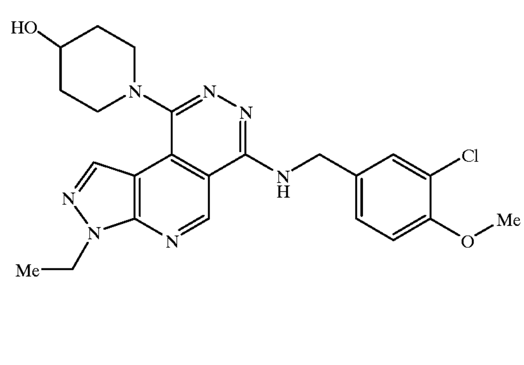 | 93 | 3.44 | m/z (M + H) 454 |

TABLE 1-continued

| NUMBER | NAME | STRUCTURE | PURITY (%) | HLPC (retention time, minutes) | OTHER DATA |
|---|---|---|---|---|---|
| 29 | N⁹-[(3-Chloro-4-methoxyphenyl)-methyl]-3-ethyl-N-(2-pyridinyl-methyl)-3H-pyrazolo[4',3':5,6]pyrido[3,4-d]pyridazine-6,9 diamine | 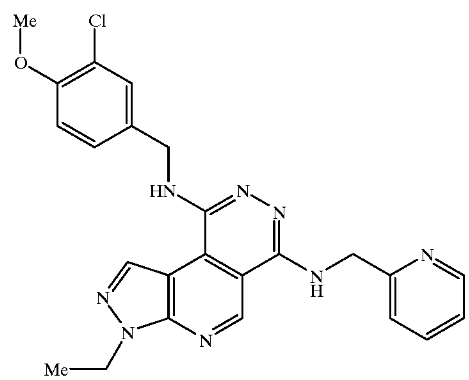 | 91 | 3.22 | m/z (M + H) 475 |
| 30 | N⁹-[(3-Chloro-4-methoxyphenyl)-methyl]-3-ethyl-N⁶-(3-pyridinyl-methyl)-3H-pyrazolo[4',3':5,6]pyrido[3,4-d]pyridazine-6,9-diamine | 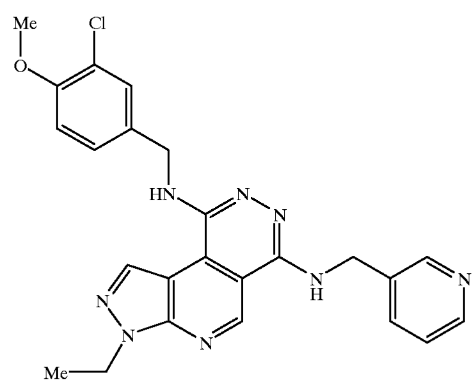 | 91 | 2.74 | m/z (M + H) 475 |
| 31 | (S)-1-[9-[[(3-Chloro-4-methoxyphenyl)-methyl]amino]-3-ethyl-3H-pyrazolo-[4',3':5,6]pyrido-[3,4-d]pyridazin-6-yl]-]-3-(dimethylamino)-pyrrolidine | 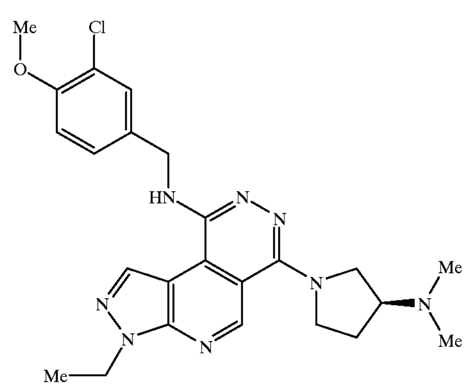 | 92 | 2.84 | m/z (M + H) 481 |

TABLE 1-continued

| NUMBER | NAME | STRUCTURE | PURITY (%) | HLPC (retention time, minutes) | OTHER DATA |
|---|---|---|---|---|---|
| 32 | 1-[9-[[(3-Chloro-4-methoxyphenyl)methyl]amino]-3-[4-methoxyphenyl]methyl-3H-pyrazolo[4',3':5,6]pyrido-[3,4-d]pyridazin-6-yl]-4-piperidinol | 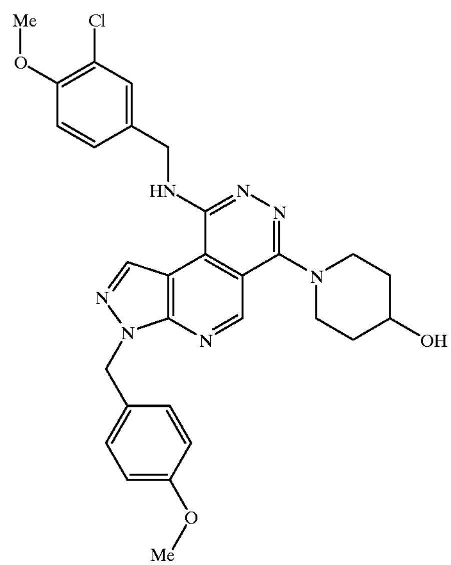 | 93 | 3.70 | m/z (M + H) 561 |
| 33 | 1-[9-[[(3-Chloro-4-methoxyphenyl)methyl]-amino]-3H-pyrazolo[4',3':5,6]pyrido-[3,4-d]pyridazin-6-yl]-4-piperidinol acetate | 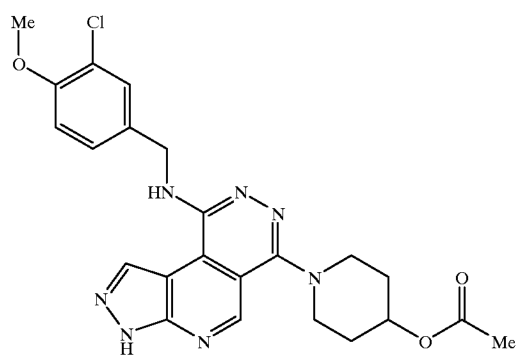 | 89 | 3.20 | m/z (M + H) 482 |
| 34 | 1-[9-[[(3-Chloro-4-methoxyphenyl)methyl]-amino]-3H-pyrazolo[4',3':5,6]pyrido-[3,4-d]pyridazin-6-yl]-4-piperidinol | 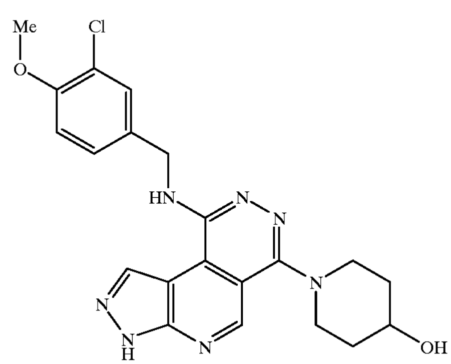 | 86 | 2.96 | m/z (M + H) 440 |

TABLE 1-continued
| NUMBER | NAME | STRUCTURE | PURITY (%) | HLPC (retention time, minutes) | OTHER DATA |
|---|---|---|---|---|---|
| 35 | 1-[9-[[(3-Chloro-phenyl)methyl]amino]-3-ethyl-3H-pyrazolo[4',3':5,6]pyrido-[3,4-d]pyridazin-6-yl]-4-piperidinol | 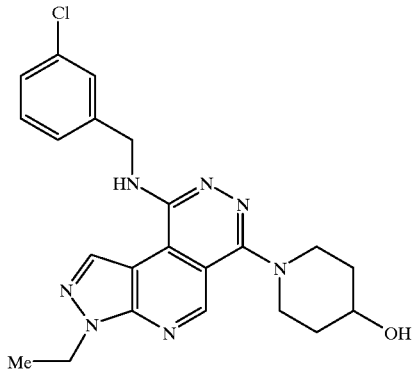 | 95 | 3.50 | m/z (M + H) 438 |
| 36 | 1-[9-[[(3,4-Dichloro-phenyl)methyl]amino]-3-ethyl-3H-pyrazolo[4',3':5,6]pyrido-[3,4-d]pyridazin-6-yl]-4-piperidinol | 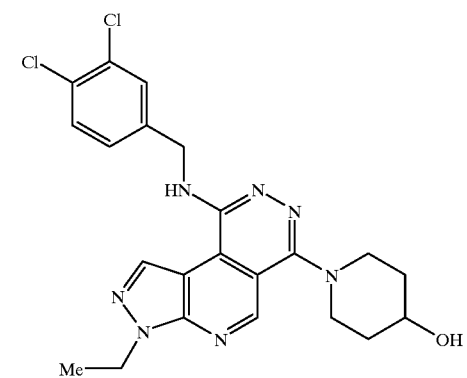 | 95 | 3.70 | m/z (M + H) 473 |
| 37 | 1-[9-[[(3-Methoxy-phenyl)methyl]amino]-3-ethyl-3H-pyrazolo[4',3':5,6]pyrido-[3,4-d]pyridazin-6-yl]-4-piperidinol | 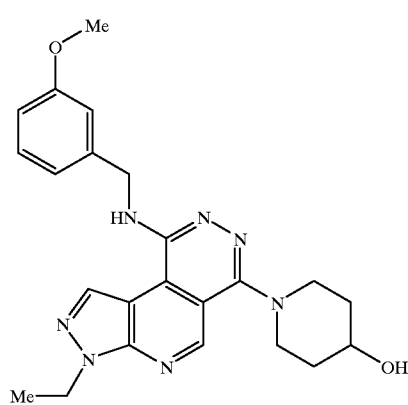 | 97 | 3.22 | m/z (M + H) 434 |

TABLE 1-continued

| NUMBER | NAME | STRUCTURE | PURITY (%) | HLPC (retention time, minutes) | OTHER DATA |
|---|---|---|---|---|---|
| 38 | N-[(3-Chloro-4-methoxyphenyl)methyl]-3-ethyl-6-[(2,6-dimethylmorpholinyl)]-3H-pyrazolo[4',3':5,6]pyrido-[3,4-d]pyridazin-9-amine | 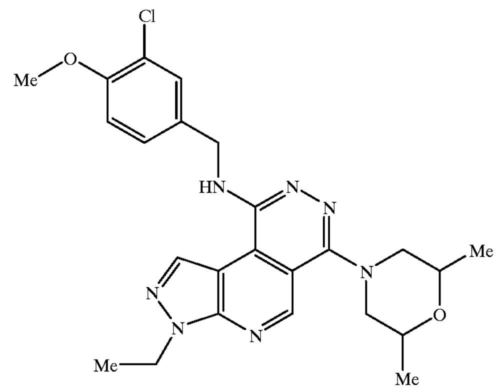 | 90 | 3.83 | m/z (M + H) 482 |
| 39 | 1-[9-[[(3-Chloro-4-methoxyphenyl)methyl]-amino]-3-ethyl-3H-pyrazolo[4',3':5,6]pyrido-[3,4-d]pyridazin-6-yl]-4-[1-acetyl]piperidine | 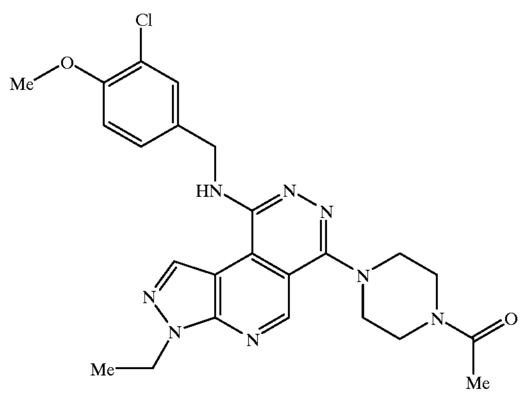 | 90 | 3.40 | m/z (M + H) 495 |
| 40 | 1-[9-[[(3-Chloro-4-methoxyphenyl)methyl]-amino]-3-ethyl-3H-pyrazolo[4',3':5,6]pyrido-[3,4-d]pyridazin-6-yl]-8-[[1,4-dioxa-8-azaspiro[4,5]]decane | 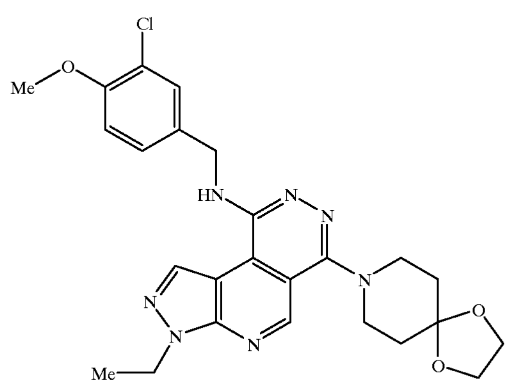 | 90 | 3.66 | m/z (M + H) 511 |

TABLE 1-continued

| NUMBER | NAME | STRUCTURE | PURITY (%) | HLPC (retention time, minutes) | OTHER DATA |
|---|---|---|---|---|---|
| 41 | (±)-1-[9-[[(3-Chloro-4-methoxyphenyl)methyl]-amino]-3-ethyl-3H-pyrazolo[4',3':5,6]pyrido-[3,4-d]pyridazin-6-yl]-]-3-piperidine-carboxamide diethyl amine | 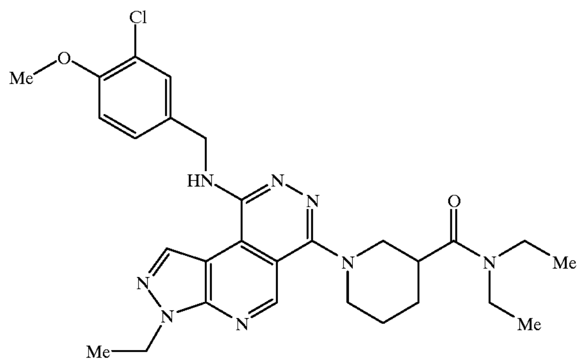 | 90 | 3.78 | m/z (M + H) 552 |
| 42 | $N^9$-[(3-Chloro-4-methoxyphenyl)methyl]-3-ethyl-6-chloro-3H-pyrazolo-[4',3':5,6]pyrido-[3,4-d]pyridazine | 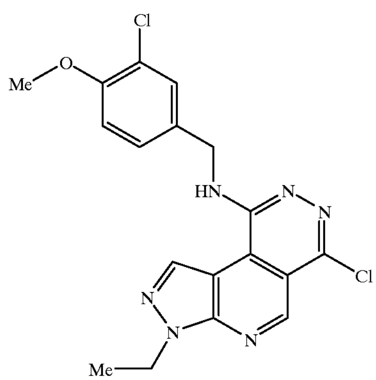 | 93 | 4.35 | m/z (M + H) 404 |
| 43 | 1-[9-[[(3-Chloro-4-methoxy-phenyl)methyl]amino]-3-ethyl-3H-pyrazolo[4',3':5,6]pyrido-[3,4-d]pyridazin-6-yl]-4-piperidinyl methyl ether | 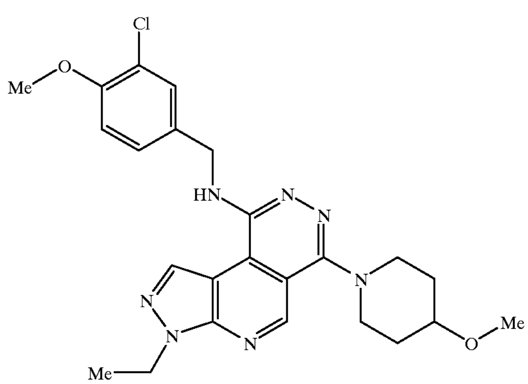 | 90 | 3.60 | m/z (M + H) 482 |
| 44 | 1-[9-[[(3-Chloro-4-methoxyphenyl)methyl]-amino]-3-ethyl-3H-pyrazolo[4',3':5,6]pyrido-[3,4-d]pyridazin-6-yl]-N-methylamine | 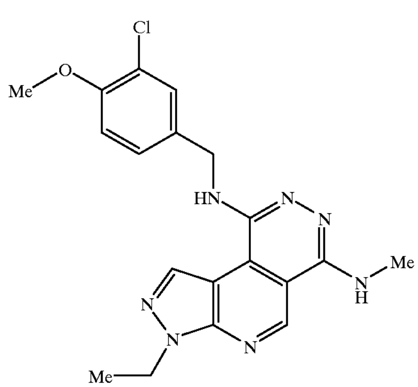 | 89 | 3.33 | m/z (M + H) 398 |

TABLE 1-continued

| NUMBER | NAME | STRUCTURE | PURITY (%) | HLPC (retention time, minutes) | OTHER DATA |
|---|---|---|---|---|---|
| 45 | 1-[9-[[(3-Chloro-4-methoxyphenyl)methyl]-amino]-3-ethyl-3H-pyrazolo[4',3':5,6]pyrido-[3,4-d]pyridazin-6-yl]-4-trans-amino-cyclohexyl-1-ol | 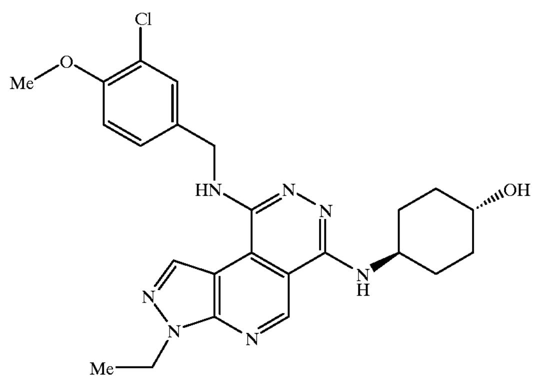 | 97 | 3.45 | m/z (M + H) 482 |
| 46 | 1-[9-[[(3-Chloro-4-methoxyphenyl)methyl]-amino]-3-ethyl-3H-pyrazolo[4',3':5,6]pyrido-[3,4-d]pyridazin-6-yl]-N,N-dimethylamine | 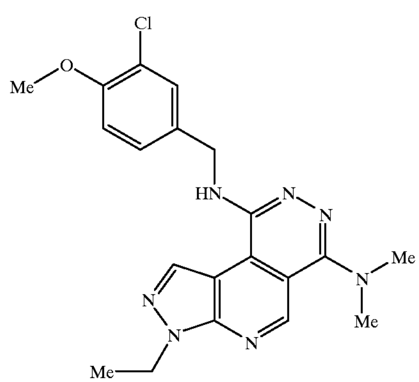 | 95 | 3.30 | m/z (M + H) 412 |
| 47 | 1-[9-[[(3-Chloro-4-methoxyphenyl)-methyl]-amino]-3-ethyl-3H-pyra-zolo[4',3':5,6-]pyrido-[3,4-d]pyri-dazin-6-yl]-N-cyclopropylamine | 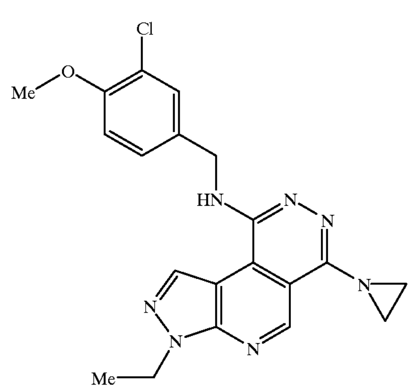 | 98 | 3.70 | m/z (M + H) 424 |

TABLE 1-continued

| NUMBER | NAME | STRUCTURE | PURITY (%) | HLPC (retention time, minutes) | OTHER DATA |
|---|---|---|---|---|---|
| 48 | 1-[9-[[(3-Chloro-4-methoxyphenyl)-methyl]-amino]-3-ethyl-3H-pyrazolo[4',3':5,6]-pyrido-[3,4-d]pyridazin-6-yl]-N-1H-imidazole | 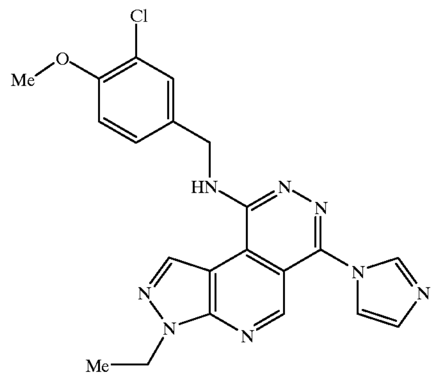 | 95 | 3.00 | m/z (M + H) 435 |
| 49 | 1-[9-[[(3-Chloro-4-methoxyphenyl)-methyl]-amino]-3-ethyl-3H-pyrazolo-[4',3':5,6]pyri-do-[3,4-d]pyridazin-6-yl]-3-(4-methylpiperizinyl)-propyldiamine | 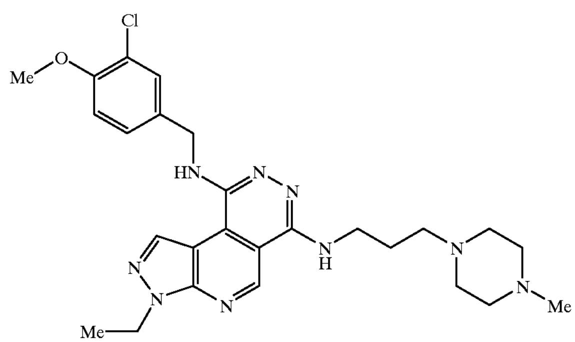 | 94 | 2.60 | m/z (M + H) 525 |
| 50 | 1-[9-[[(3-Chloro-4-methoxy-phenyl)methyl]amino]-3-ethyl-3H-pyrazolo[4',3':5,6]pyrido-[3,4-d]pyridazin-6-yl]-4-piperidinyl-O-methyloxime | 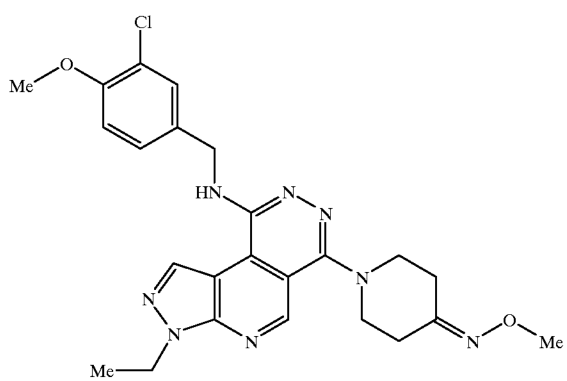 | 90 | 3.74 | m/z (M + H) 495 |
| 51 | 1-[9-[[(3-Chloro-4-methoxy-phenyl)-methyl]amino]-3-ethyl-3H-pyrazolo-[4',3':5,6]pyrido-[3,4-d]pyridazin-6-yl]-4-piperidinyl oxime | 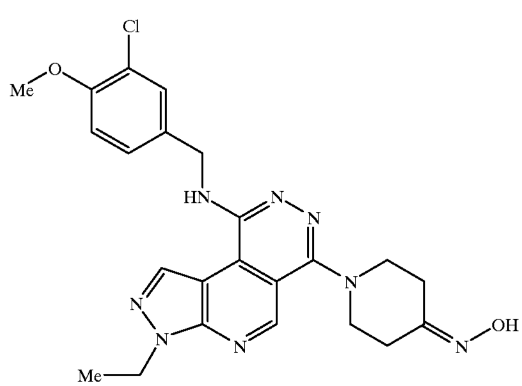 | 90 | 3.44 | m/z (M + H) 481 |

TABLE 1-continued

| NUMBER | NAME | STRUCTURE | PURITY (%) | HLPC (retention time, minutes) | OTHER DATA |
|---|---|---|---|---|---|
| 52 | 1-[9-[[(3-Chloro-4-methoxyphenyl)-methyl]-amino]-3-ethyl-3H-pyrazolo-[4',3':5,6]-pyrido-[3,4-d]pyri-dazin-6-yl]-3-(morpholinyl)-ethyldiamine | 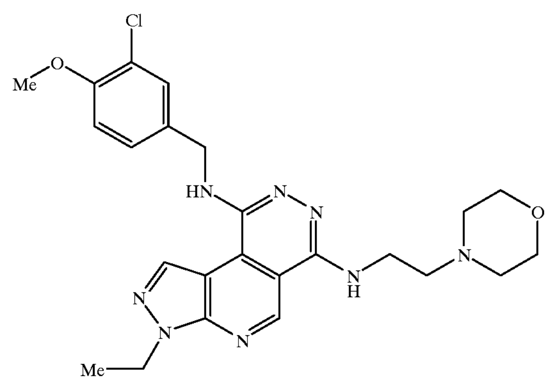 | 92 | 2.65 | m/z (M + H) 498 |
| 53 | 1-[9-[[(3-Chloro-4-methoxyphenyl)-methyl]-amino]-3-ethyl-3H-pyrazolo-[4',3':5,6]pyrido-[3,4-d]pyridazin-6-yl]-1-amino-4-butanol | 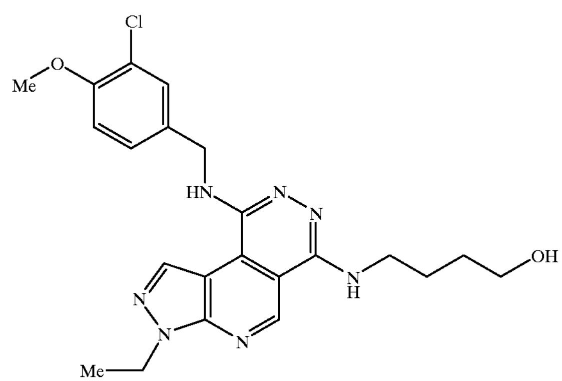 | 95 | 3.34 | m/z (M + H) 456 |
| 54 | 1-[9-[[(3-Chloro-4-methoxyphenyl)methyl]-amino]-3-ethyl-3H-pyrazolo[4',3':5,6]pyrido-[3,4-d]pyridazin-6-yl]-N,N-dimethylethyl diamine | 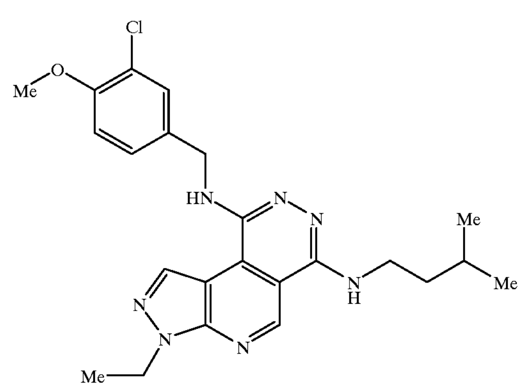 | 98 | 2.60 | m/z (M + H) 455 |

TABLE 1-continued

| NUMBER | NAME | STRUCTURE | PURITY (%) | HLPC (retention time, minutes) | OTHER DATA |
|---|---|---|---|---|---|
| 55 | 1-[9-[[(3-Chloro-4-methoxy-phenyl)methyl]amino]-3-ethyl-3H-pyrazolo[4',3':5,6]pyrido-[3,4-d]pyridazin-6-yl]-N,N-dimethyl-4-piperidine | 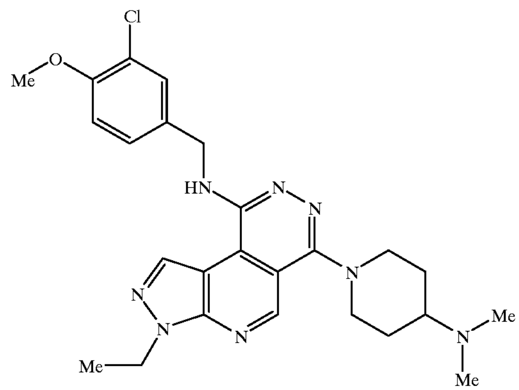 | 90 | 2.72 | m/z (M + H) 496 |
| 56 | 1-[9-[[(3-Chloro-4-methoxy-phenyl)-methyl]amino]-3-ethyl-3H-pyrazolo-[4',3':5,6]pyrido-[3,4-d]pyridazin-6-yl]-N-cyclopropyl-4-piperidine | 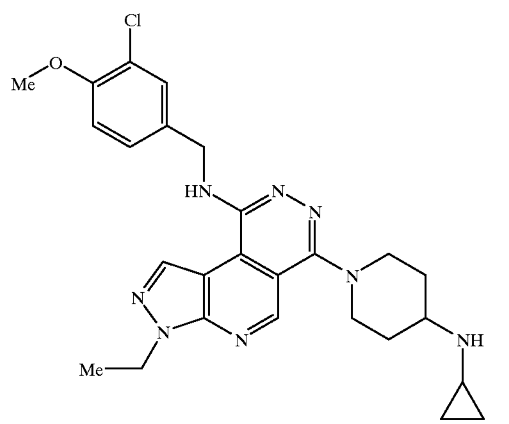 | 90 | 2.95 | m/z (M + H) 508 |
| 57 | 1-[9-[[(3-Chloro-4-methoxy-phenyl)-methyl]amino]-3-ethyl-3H-pyrazolo-4',3':5,6]pyrido-[3,4-d]pyridazin-6-yl]-N-ethyl-4-piperidine | 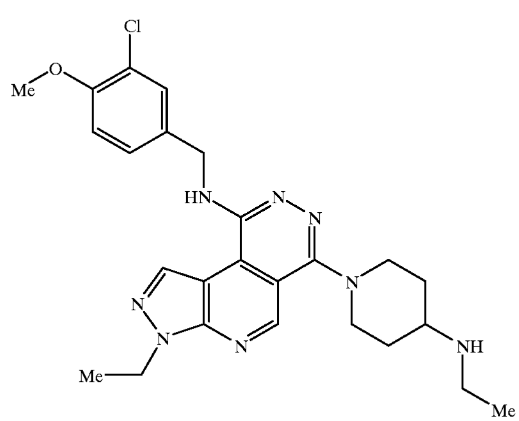 | 90 | 2.74 | m/z (M + H) 496 |

TABLE 1-continued

| NUMBER | NAME | STRUCTURE | PURITY (%) | HLPC (retention time, minutes) | OTHER DATA |
|---|---|---|---|---|---|
| 58 | 1-[9-[[(3-Chloro-4-methoxy-phenyl)methyl]amino]-3-ethyl-3H-pyrazolo-[4',3':5,6]pyri-do-[3,4-d]pyridazin-6-yl]-N-aminomorphline | 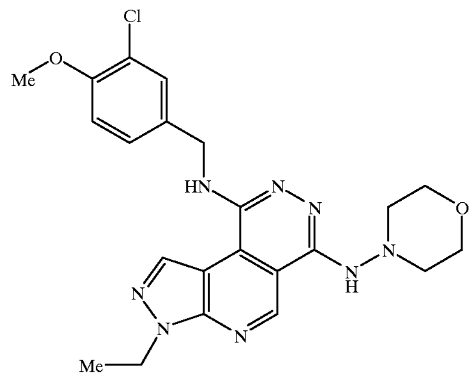 | 94 | 3.28 | m/z (M + H) 469 |
| 59 | 1-[9-[[(3-Chloro-4-methoxy-phenyl)-methyl]amino]-3-ethyl-3H-pyrazolo-d]pyridazin-6-yl]-4-[4',3':5,6]pyrido-[3,4-methoxy-carbonyl-methylamino piperidine | 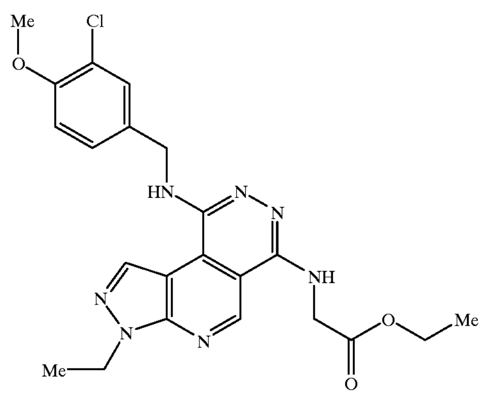 | | | m/x (M + H) 554 |
| 60 | 1-[9-[[(3-Chloro-4-methoxy-phenyl)-methyl]amino]-3-ethyl-3H-pyrazolo-[4',3':5,6]pyrido-[3,4-d]pyridazin-6-yl]pyrrolidine | 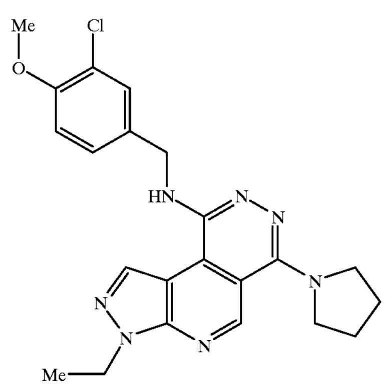 | | | m/z (M + H) 438 |

TABLE 1-continued

| NUMBER | NAME | STRUCTURE | PURITY (%) | HLPC (retention time, minutes) | OTHER DATA |
|---|---|---|---|---|---|
| 61 | 1-[9-[[(3-Chloro-4-methoxy-phenyl)methyl]amino]-3-ethyl-3H-pyrazolo[4',3':5,6]pyrido-[3,4-d]pyridazin-6-yl]piperidine | 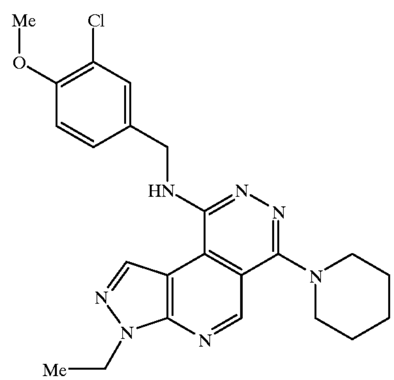 | | | m/z (M + H) 452 |
| 62 | 4-[9-[[(3-Chloro-4-methoxy-phenyl)methyl]amino]-3-ethyl-3H-pyrazolo[4',3':5,6]pyrido-[3,4-d]pyridazin-6-yl]aminomethyl-2,6-dichloropyridine | 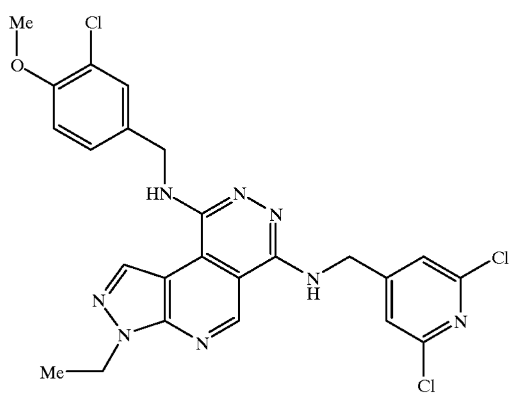 | | | m/z (M + H) 544 |
| 63 | 1-Acetyl-4-[9-[[(3-chloro-4-methoxy-phenyl)methyl]amino]-3-ethyl-3H-pyrazolo[4',3':5,6]pyrido-[3,4-d]pyridazin-6-yl]aminomethyl-piperidine | 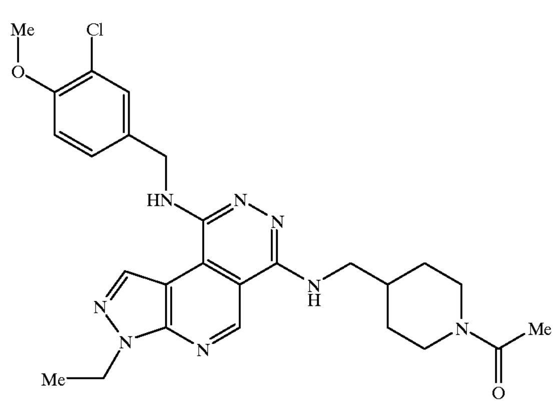 | | | m/z (M + H) 524 |

TABLE 1-continued

| NUMBER | NAME | STRUCTURE | PURITY (%) | HLPC (retention time, minutes) | OTHER DATA |
|---|---|---|---|---|---|
| 64 | 1-[9-[[(3-Chloro-4-methoxy-phenyl)methyl]amino]-3-ethyl-3H-pyrazolo[4',3':5,6]pyrido-[3,4-d]pyridazin-6-yl]-4-amino-cyclohexanoneoxime | 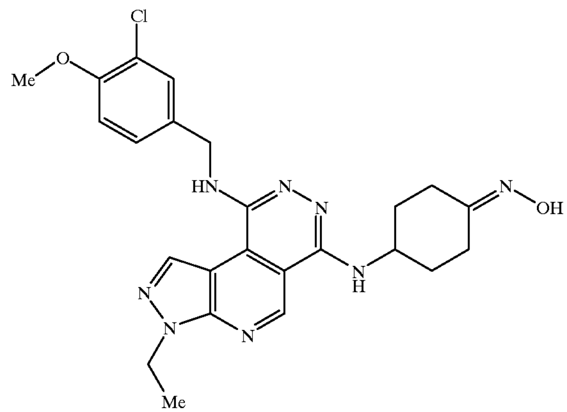 | 91 | 3.3 | m/z (M + H) 495 |
| 65 | 1-[9-[[(3-Chloro-4-methoxy-phenyl)methyl]amino]-3-ethyl-3H-pyrazolo[4',3':5,6]pyrido-[3,4-d]pyridazin-6-yl]-4-amino-cyclohexanone-O-methyloxime | 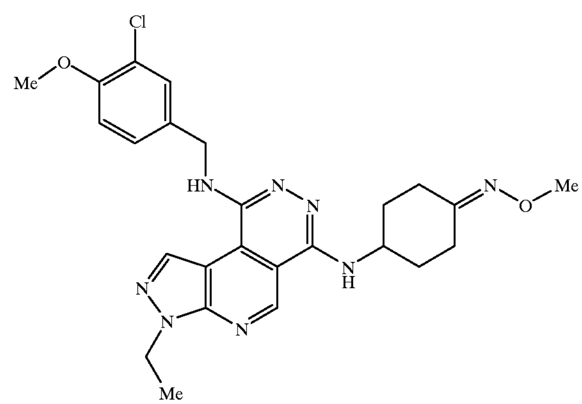 | 94 | 3.6 | m/z (M + H) 509 |
| 66 | 1-[9-[[(3-Chloro-4-methoxyphenyl)methyl]-amino]-3-propyl-3H-pyrazolo[4',3':5,6]pyrido-[3,4-d]pyridazin-6-yl]-4-trans-aminocyclohexyl-1-ol | 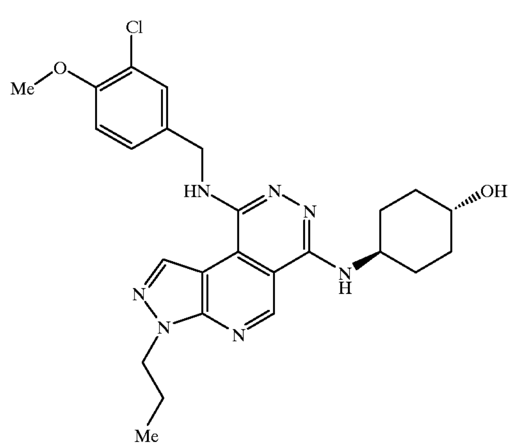 | 95 | 3.5 | m/z (M + H) 496 |

TABLE 1-continued

| NUMBER | NAME | STRUCTURE | PURITY (%) | HLPC (retention time, minutes) | OTHER DATA |
|---|---|---|---|---|---|
| 67 | 1-[9-[[(3-Chloro-4-methoxyphenyl)methyl]-amino]-3-ethyl-3H-pyrazolo[4',3':5,6]pyrido-[3,4-d]pyridazin-6-yl]-3-amino-(1-imidazole)-propyldiamine | 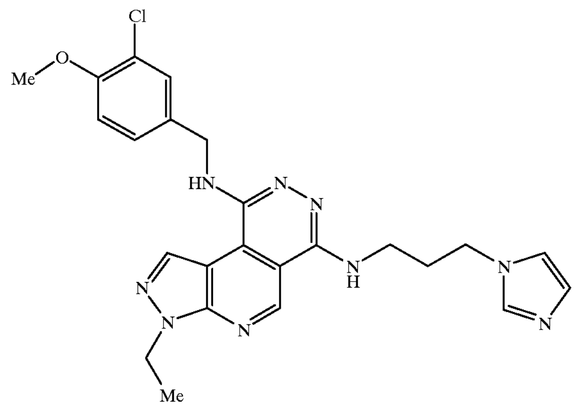 | 87 | 2.7 | m/z (M + H) 492 |
| 68 | 1-[9-[[(3-Chloro-4-methoxyphenyl)methyl]-amino]-3-ethyl-3H-pyrazolo[4',3':5,6]pyrido-[3,4-d]pyridazin-6-yl]-N-1H-3-methyl-imidazole Iodide | 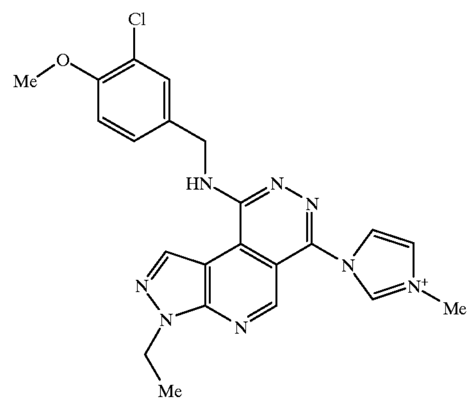 | 95 | 2.8 | m/z (M + H) 449 |
| 69 | 1-[9-[[(3-Chloro-4-methoxyphenyl)methyl]-amino]-3-ethyl-3H-pyrazolo[4',3':5,6]pyrido-[3,4-d]pyridazin-6-yl]-N-1H-imidazole-4-methylcarboxylate | 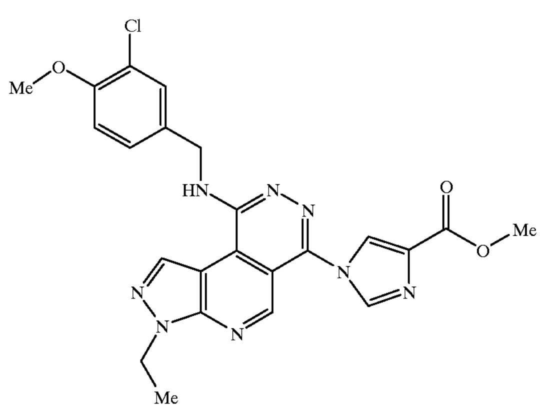 | 89 | 3.8 | m/z (M + H) 493 |

TABLE 1-continued

| NUMBER | NAME | STRUCTURE | PURITY (%) | HLPC (retention time, minutes) | OTHER DATA |
|---|---|---|---|---|---|
| 70 | 1-[9-[[(3-Chloro-4-methoxyphenyl)methyl]-amino]-3-ethyl-3H-pyrazolo[4',3':5,6]pyrido-[3,4-d]pyridazin-6-yl]-amine | 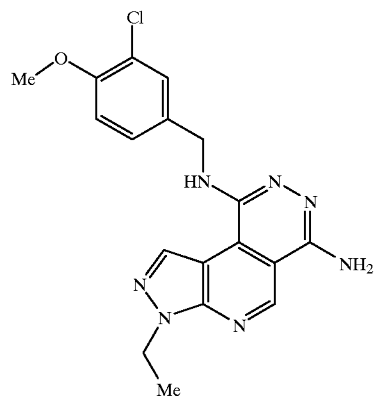 | 87 | 3.2 | m/z (M + H) 384 |
| 71 | 1-[6-[[(3-Chloro-4-methoxyphenyl)methyl]-amino]-3-ethyl-3H-pyrazolo[4',3':5,6]pyrido-[3,4-d]pyridazin-9-yl]-amine | 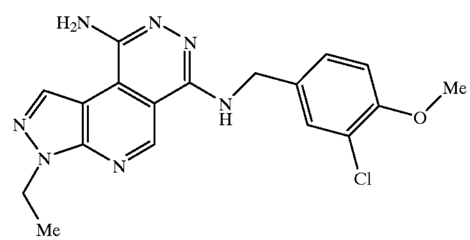 | 90 | 3.2 | m/z (M + H) 384 |
| 72 | 1-[9-[[(3-Chloro-4-methoxy-phenyl)methyl]amino]-3-ethyl-3H-pyrazolo[4',3':5,6]pyrido-[3,4-d]pyridazin-6-yl]hexamethylene-imine | 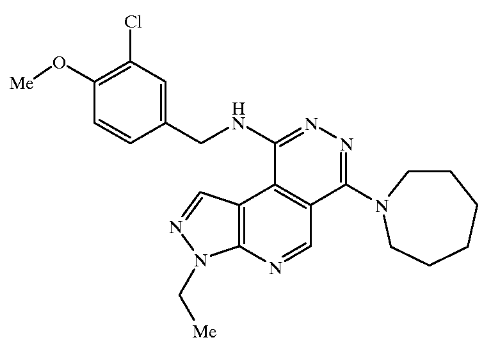 | 88 | 3.6 | m/z (M + H) 466 |
| 73 | 1-[9-[[(3-Chloro-4-methoxyphenyl)methyl]-amino]-3-ethyl-3H-pyrazolo[4',3':5,6]pyrido-[3,4-d]pyridazin-6-yl]-N-1H-imidazole-4-methanol (BMS-339446) | 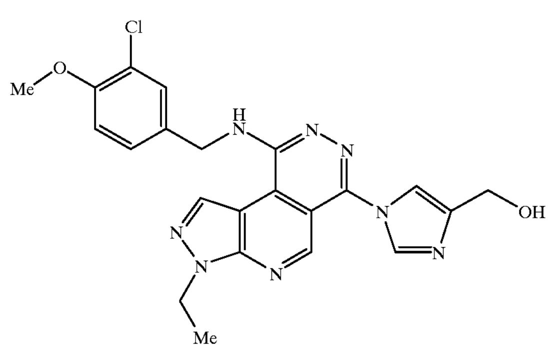 | 98 | 3.1 | m/z (M + H) 465 |

TABLE 1-continued

| NUMBER | NAME | STRUCTURE | PURITY (%) | HLPC (retention time, minutes) | OTHER DATA |
|---|---|---|---|---|---|
| 74 | 1-[9-[[(3-Chloro-4-methoxyphenyl)methyl]-amino]-3-ethyl-3H-pyrazolo[4',3':5,6]pyrido-[3,4-d]pyridazin-6-yl]-ethylsuccinate carboxamide | 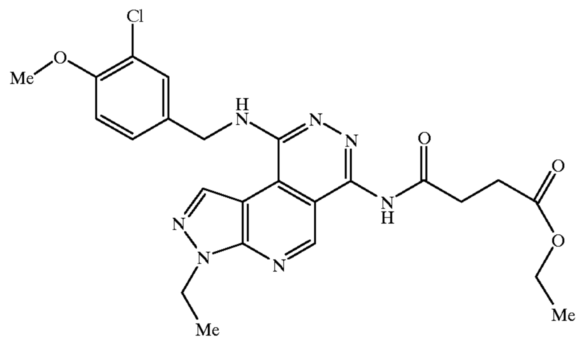 | 92 | 3.7 | m/z (M + H) 512 |
| 75 | 1-[9-[[(3-Chloro-4-methoxyphenyl)methyl]-amino]-3-ethyl-3H-pyrazolo[4',3':5,6]pyrido-[3,4-d]pyridazin-6-yl]-carboxamide succinic acid | 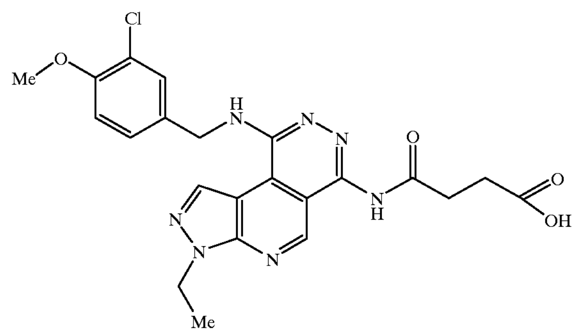 | 94 | 3.1 | m/z (M + H) 484 |
| 76 | 1-[9-[[(3-Chloro-4-methoxyphenyl)methyl]-amino]-3-ethyl-3H-pyrazolo[4',3':5,6]pyrido-[3,4-d]pyridazin-6-yl]-N-1H-imidazole-4-carboxylic acid | 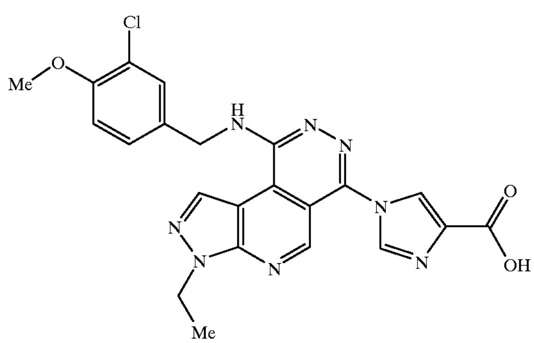 | 89 | 3.5 | m/z (M + H) 479 |
| 77 | 1-[9-[[(3-Chloro-4-methoxyphenyl)methyl]-amino]-3-ethyl-3H-pyrazolo[4',3':5,6]pyrido-[3,4-d]pyridazin-6-yl]-(2R)-aminomethyl-tetrahydrofuran | 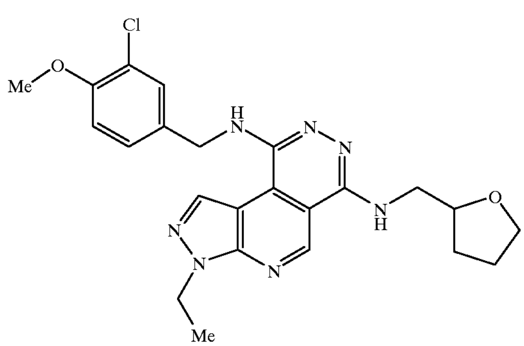 | 94 | 3.4 | m/z (M + H) 468 |

TABLE 1-continued

| NUMBER | NAME | STRUCTURE | PURITY (%) | HLPC (retention time, minutes) | OTHER DATA |
|---|---|---|---|---|---|
| 78 | 1-[9-[[(3-Chloro-4-methoxyphenyl)methyl]-amino]-3-propyl-3H-pyrazolo[4',3':5,6]pyrido-[3,4-d]pyridazin-6-yl]-4-trans-amino-cyclohexyl-1-one | 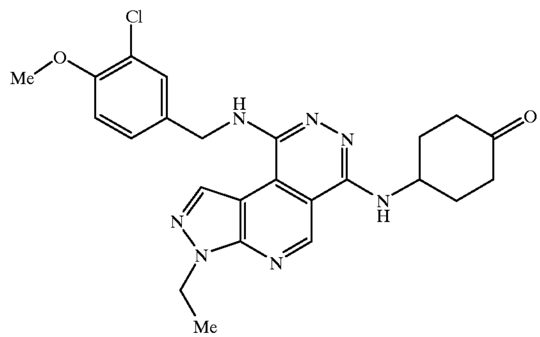 | 91 | 3.34 | m/z (M + H) 480 |
| 79 | 1-[9-[[(3-Chloro-4-methoxyphenyl)methyl]-amino]-3-propyl-3H-pyrazolo[4',3':5,6]pyrido-[3,4-d]pyridazin-6-yl]-2-trans-aminocyclohexyl-1-ol | 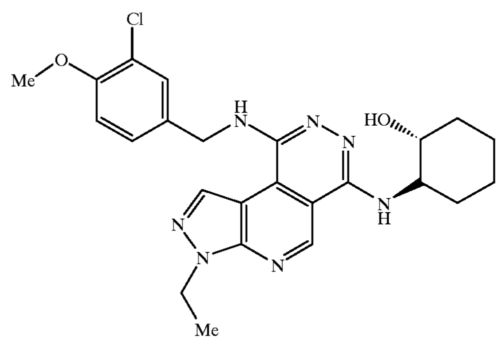 | 83 | 3.61 | m/z (M + H) 482 |
| 80 | 1-[9-[[(3-Chloro-4-methoxyphenyl)methyl]-amino]-3-propyl-3H-pyrazolo[4',3':5,6]pyrido-[3,4-d]pyridazin-6-yl]-4-aminomethyl-piperidine | 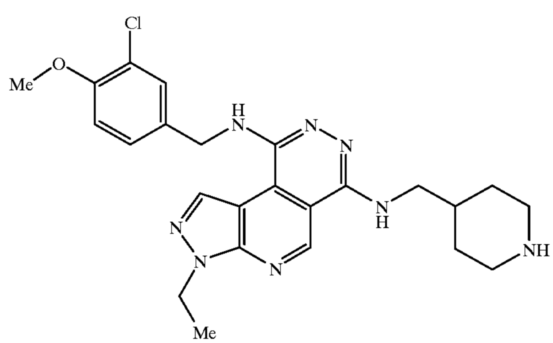 | 90 | 3.01 | m/z (M + H) 481 |
| 81 | 1-[9-[[(3-Chloro-4-methoxyphenyl)-methyl]amino]-3-ethyl-3H-pyrazolo[4',3':5,6]pyrido[3,4-d]pyridazin-6-yl]-3-piperidinol | 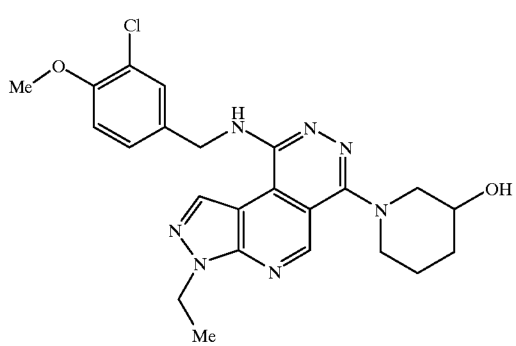 | 88 | 3.34 | m/z (M + H) 468 |

TABLE 1-continued

| NUMBER | NAME | STRUCTURE | PURITY (%) | HLPC (retention time, minutes) | OTHER DATA |
|---|---|---|---|---|---|
| 82 | 1-[9-[[(3-Chloro-4-methoxyphenyl)methyl]-amino]-3-ethyl-3H-pyrazolo[4',3':5,6]pyrido-[3,4-d]pyridazin-6-yl]-ethylpropionate amine | 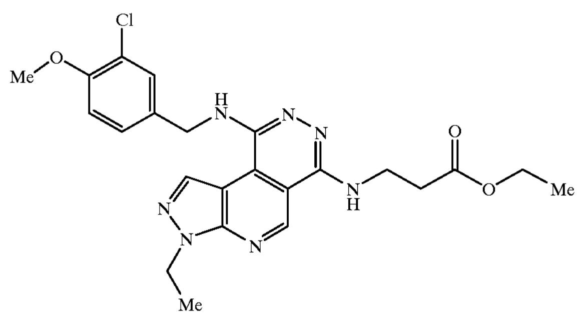 | 83 | 3.51 | m/z (M + H) 484 |
| 83 | 1-[9-[[(3-Chloro-4-methoxyphenyl)methyl]-amino]-3-ethyl-3H-pyrazolo[4',3':5,6]pyrido-[3,4-d]pyridazin-6-yl]-aminopropionic acid | 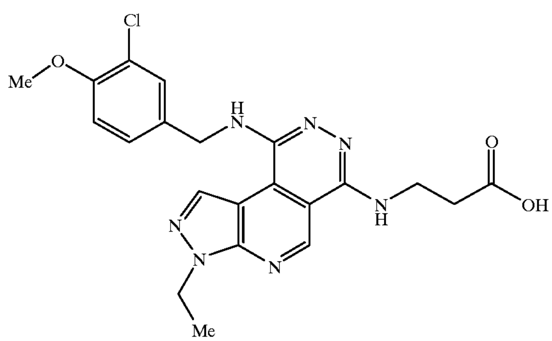 | 87 | 3.3 | m/z (M + H) 456 |
| 84 | 1-[9-[[(3-Chloro-4-methoxyphenyl)-methyl]-amino]-3-propyl-3H-pyrazolo[4',3':5,6]-pyrido-[3,4-d]pyridazin-6-yl]-4-cis-aminocyclohexyl-1-carboxylic acid | 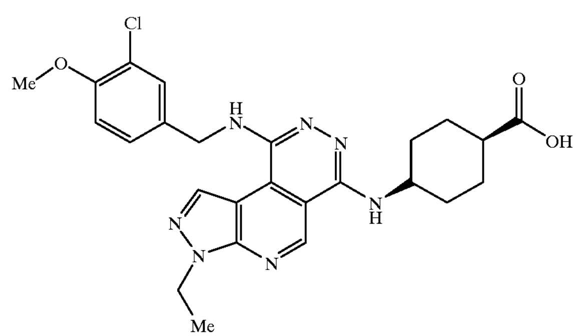 | 78 | 3.62 | m/z (M + H) 510 |
| 85 | 1-[9-[[(3-Chloro-4-methoxyphenyl)-methyl]-amino]-3-propyl-3H-pyrazolo[4',3':5,6]-pyrido-[3,4-d]pyridazin-6-yl]-4-cis-aminocyclohexyl-1-ethylcarboxylate | 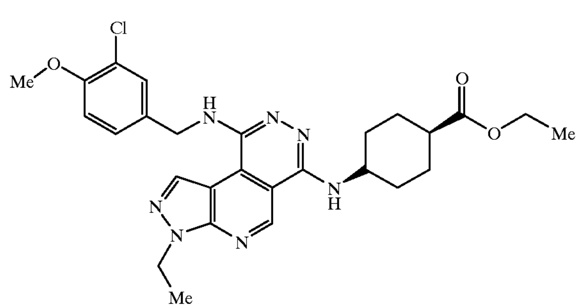 | 91 | 3.79 | m/z (M + H) 538 |

TABLE 1-continued

| NUMBER | NAME | STRUCTURE | PURITY (%) | HLPC (retention time, minutes) | OTHER DATA |
|---|---|---|---|---|---|
| 86 | 1-[9-[[(3-Chloro-4-methoxyphenyl)-methyl]-amino]-3-ethyl-3H-pyrazolo[4',3':5,6]-pyrido-[3,4-d]pyridazin-6-yl]-3-(4-methylpiperizinyl)-ethyldiamine | 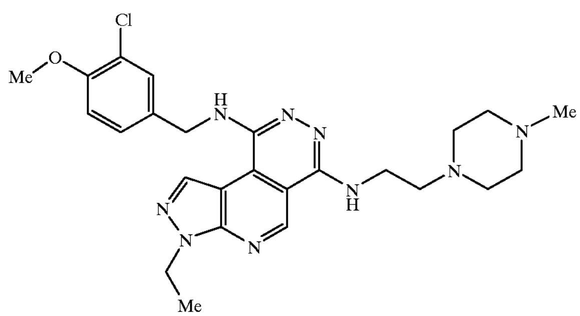 | 86 | 2.52 | m/z (M + H) 510 |
| 87 | N⁶-[(3-Chloro-4-methoxyphenyl)-methyl]-3-ethyl-9-chloro-3H-pyrazolo[4',3':5,6]-pyrido-[3,4-d]pyridazine | 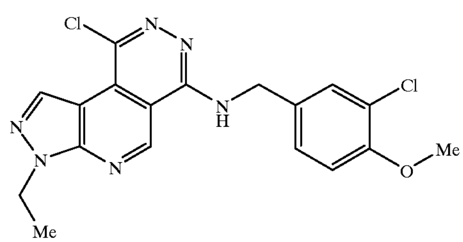 | 89 | 4.20 | m/z (M + H) 403 |
| 88 | 1-[9-[[(3-Chloro-4-methoxyphenyl)-methyl]amino]-3-ethyl-3H-pyrazolo[4',3':5,6]pyrido[3,4-d]pyridazin-6-yl]-4-piperidinyl-1-ol | 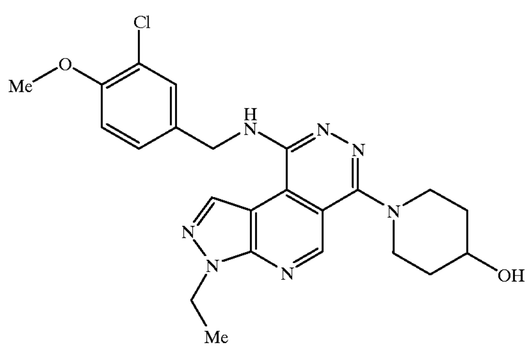 | 95 | 3.20 | m/z (M + H) 468 |
| 89 | 3-Ethyl-3H-pyrazolo[4',3':5,6]pyrido[3,4-d]pyridazin-6,9-yl]-thiophenol | 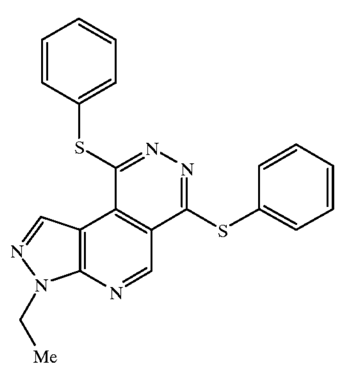 | 89 | 9.30 | m/z (M + H) 416 |

TABLE 1-continued

| NUMBER | NAME | STRUCTURE | PURITY (%) | HLPC (retention time, minutes) | OTHER DATA |
|---|---|---|---|---|---|
| 90 | 1-[9-[[(3-chloro-2-methoxypyrido)methyl]amino]-3-ethyl-3H-pyrazolo[4',3':5,6]pyrido[3,4-d]pyridazin-6-yl]-1H-imidazole-4-methyl carboxamide | 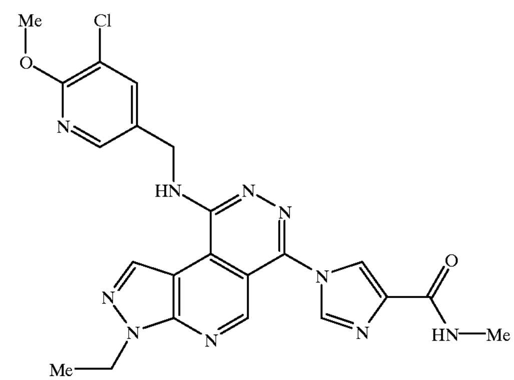 | 93 | 3.1 | m/z (M + H) 493 |
| 91 | 1-[9-[[(3-Chloro-4-methoxyphenyl)methyl]-amino]-3-ethyl-3H-pyrazolo[4',3':5,6]pyri-do-[3,4-d]pyridazin-6-yl]-N-1H-imidazole-4-formaldoxime | 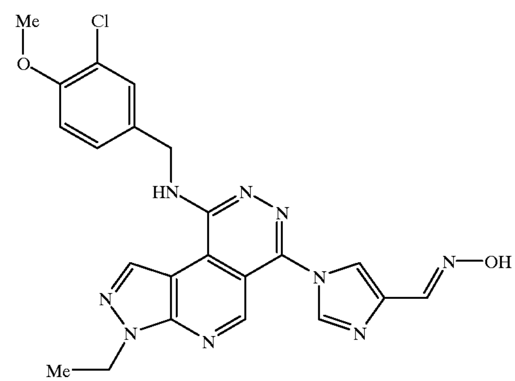 | 88 | 2.7; 2.9 | m/z (M + H) 477 |
| 92 | 1-[9-[[(3-Chloro-4-methoxyphenyl)methyl]-amino]-3-ethyl-3H-pyrazolo[4',3':5,6]pyri-do-[3,4-d]pyridazin-6-yl)-N-1H-imidazole-4-(O-methyl)formaldoxime | 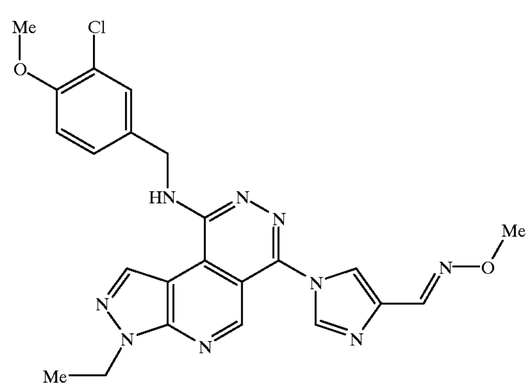 | 95 | 3.2, 3.4 | m/z (M + H) 492 |

TABLE 1-continued

| NUMBER | NAME | STRUCTURE | PURITY (%) | HLPC (retention time, minutes) | OTHER DATA |
|---|---|---|---|---|---|
| 93 | 1-[9-[[(3-Chloro-4-methoxyphenyl)methyl]-amino]-3-ethyl-3H-pyrazolo[4',3':5,6]pyri-do-[3,4-d]pyridazin-6-yl]-N-1H-imidazole-4-(N,N-dimethyl)formaldohydrozone | 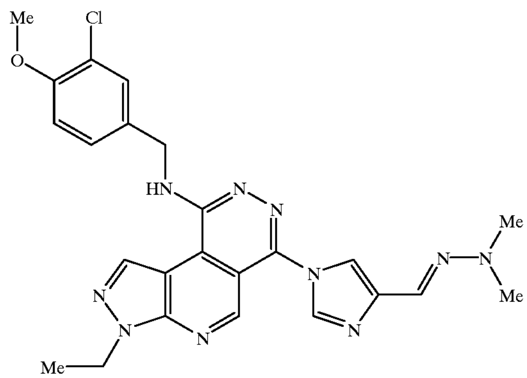 | 90 | 2.7 | m/z (M + H) 505 |
| 94 | 1-[9-[[(3-Chloro-4-methoxyphenyl)methyl]-amino]-3-ethyl-3H-pyrazolo[4',3':5,6]pyri-do-[3,4-d]pyridazin-6-yl]-N-1H-imidazole-4-(N,N-dimethylethylene)carboxamide | 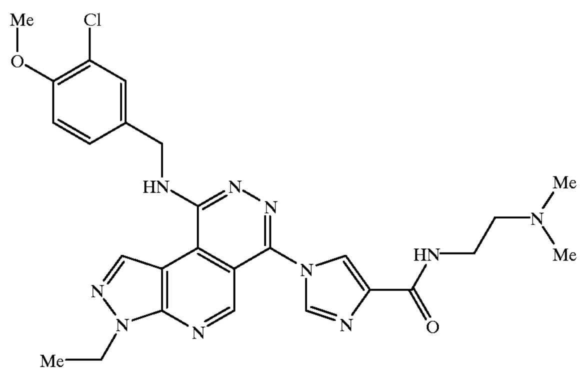 | 90 | 2.5 | m/z (M + H) 549 |
| 95 | 1-[9-[[(3-Chloro-4-methoxyphenyl)methyl]-yl)-amino]-3-ethyl-3H-pyrazolo[4',3':5,6]pyri-do-[3,4-d]pyridazin-6-yl]-N-1H-imidazole-4-(N-methylpiperidinyl)carboxamide | 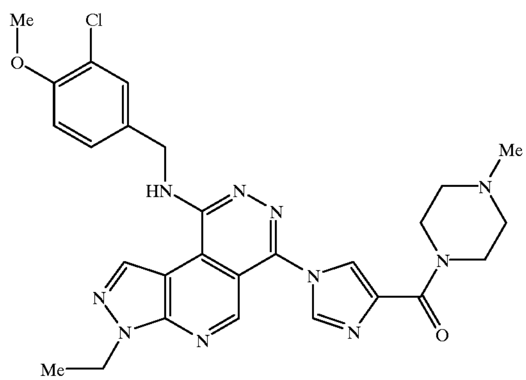 | 90 | 2.4 | m/z (M + H) 561 |
| 96 | 1-[9-[[(3-Chloro-4-methoxyphenyl)methyl]-amino]-3-ethyl-3H-pyrazolo[4',3':5,6]pyri-do-[3,4-d]pyridazin-6-yl]-N-1H-imidazole-4-(2-amino-2-methylpropyl)carboxamide | 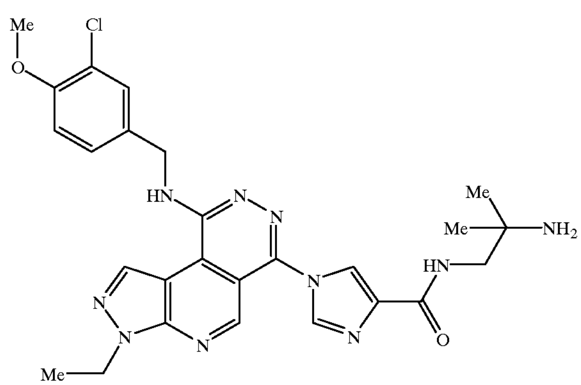 | 90 | 3.2 | m/z (M + H) 549 |

TABLE 1-continued

| NUMBER | NAME | STRUCTURE | PURITY (%) | HLPC (retention time, minutes) | OTHER DATA |
|---|---|---|---|---|---|
| 97 | 1-[9-[[(3-Chloro-4-methoxyphenyl)-methyl]-amino]-3-ethyl-3H-pyrazolo[4',3':5,6]-pyrido-[3,4-d]pyridazin-6-yl]-2R-tetrahydrofurylmethyl-amine | 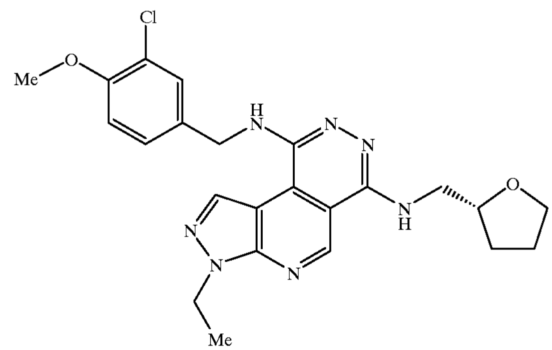 | 94 | 3.40 | m/z (M + H) 468 |
| 98 | 1-[9-[[(3-Chloro-4-methoxyphenyl)-methyl]-amino)-3-ethyl-3H-pyrazolo[4',3':5,6]-pyrido-[3,4-d]pyridazin-6-yl]-2S-tetrahydrofurylmethyl-amine | 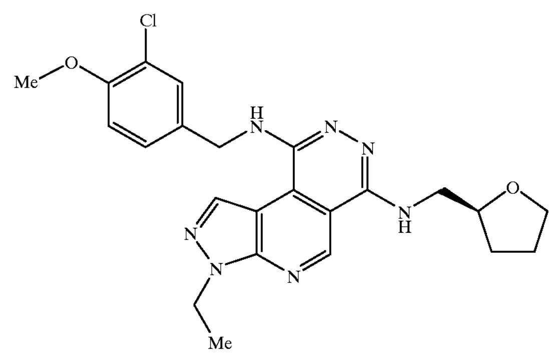 | 86 | 3.46 | m/z (M + H) 468 |
| 99 | 1-[9-[[(3-Chloro-4-methoxyphenyl)methyl]-yl]-amino]-3-ethyl-3H-pyrazolo[4',3':5,6]-pyri-do-[3,4-d]pyridazin-6-yl]-N-1H-imidazole-4-dimethylamino carboxamide | 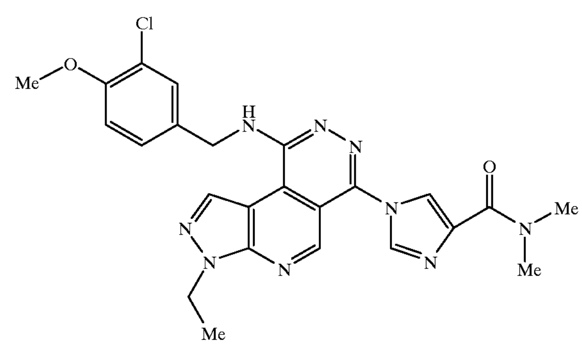 | 95 | 3.60 | m/z (M + H) 506 |
| 100 | 1-[9-[[(3-Chloro-4-methoxyphenyl)-methyl]-amino]-3-ethyl-3H-pyrazolo[4',3':5,6]-pyrido-[3,4-d]pyridazin-6-yl]-3-aminopropyl carboxamide | 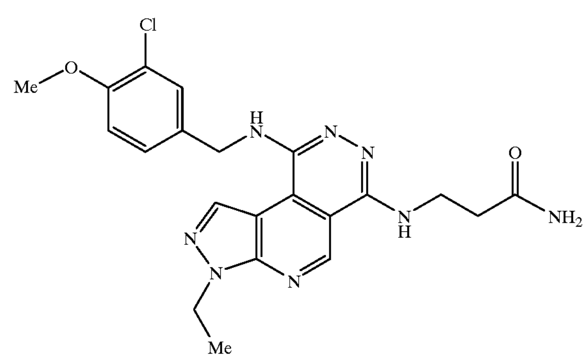 | 93 | 3.08 | m/z (M + H) 455 |

TABLE 1-continued

| NUMBER | NAME | STRUCTURE | PURITY (%) | HLPC (retention time, minutes) | OTHER DATA |
|---|---|---|---|---|---|
| 101 | 1-[9-[[(3-Chloro-4-methoxyphenyl)-methyl]-amino]-3-ethyl-3H-pyrazolo[4',3':5,6]-pyrido-[3,4-d]pyridazin-6-yl]-4-cis-aminocyclohexyl-1-carboxamide | 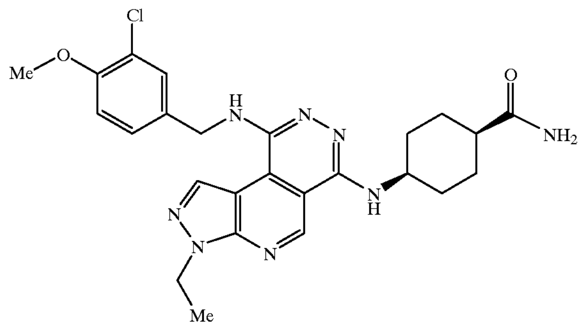 | 92 | 3.32 | m/z (M + H) 509 |
| 102 | 1-[9-[[(3-Chloro-4-methoxyphenyl)-methyl]-amino]-3-ethyl-3H-pyrazolo[4',3':5,6]-pyrido-[3,4-d]pyridazin-6-yl]-3-(N-morpholino)-propyldiamine | 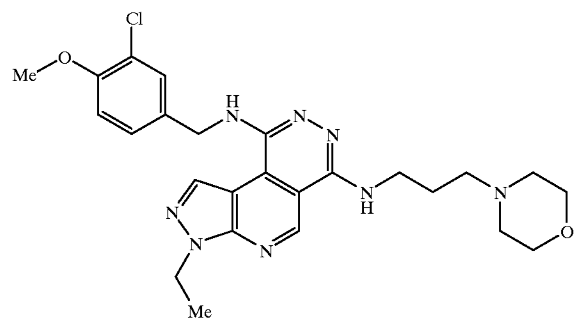 | 97 | 3.02 | m/z (M + H) 511 |
| 103 | 1-[9-[[(3-Chloro-4-methoxyphenyl)-methyl]-amino]-3-ethyl-3H-pyrazolo[4',3':5,6]-pyrido-[3,4-d]pyridazin-6-yl]-2-(piperidinyl)-ethyldiamine | 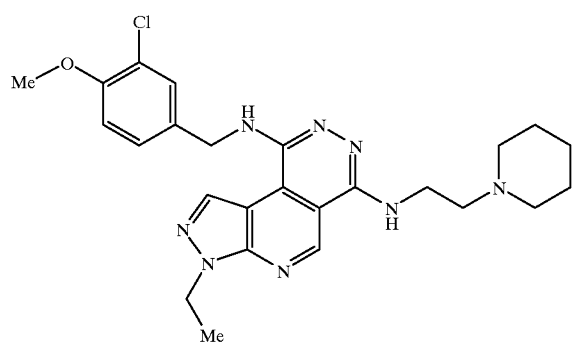 | 89 | 2.85 | m/z (M + H) 495 |
| 104 | 1-[9-[[(3-Chloro-4-methoxyphenyl)-methyl]-amino]-3-ethyl-3H-pyrazolo[4',3':5,6]-pyrido-[3,4-d]pyridazin-6-yl]-4-cis-aminocyclohexyl-1-carboxylic acid | 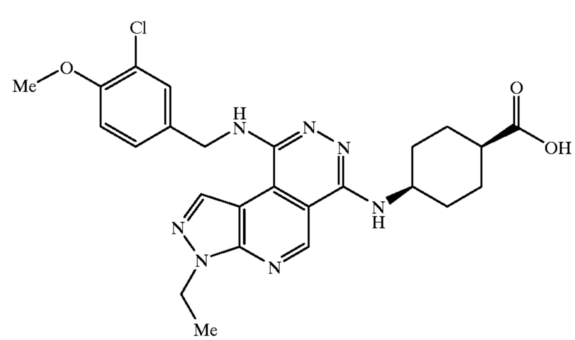 | 95 | 2.91 | m/z (M + H) 510 |

TABLE 1-continued

| NUMBER | NAME | STRUCTURE | PURITY (%) | HLPC (retention time, minutes) | OTHER DATA |
|---|---|---|---|---|---|
| 105 | 1-[9-[[(3-Chloro-4-methoxyphenyl)-methyl]-amino]-3-ethyl-3H-pyrazolo[4'3':5,6]-pyrido-[3,4-d]pyridazin-6-yl)-methyl ether | 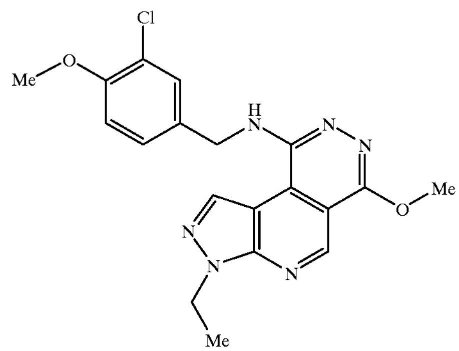 | 93 | 3.60 | m/z (M + H) 399 |
| 106 | 1-[9-[[(3-Chloro-4-methoxyphenyl)-methyl]-amino]-3-ethyl-3H-pyrazolo[4',3':5,6]-pyrido-[3,4-d]pyridazin-6-yl]-4-(2-ethylamino)-tetrahydropuran | 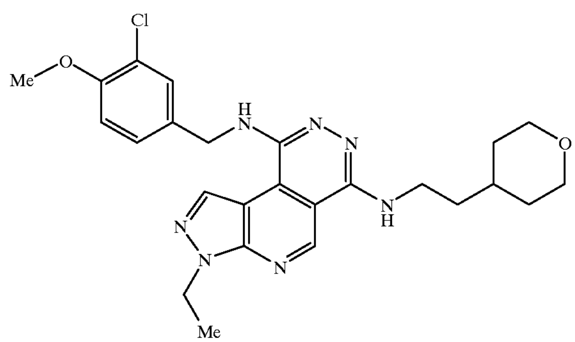 | 90 | 3.11 | m/z (M + H) 496 |
| 107 | 1-[9-[[(3-Chloro-methoxyphenyl)methyl]-yl]-amino]-3-ethyl-3H-pyrazolo[4',3':5,6]-pyri-do-[3,4-d]pyridazin-6-yl]-N-1H-imidazole-4-dimethyl)methylamine | 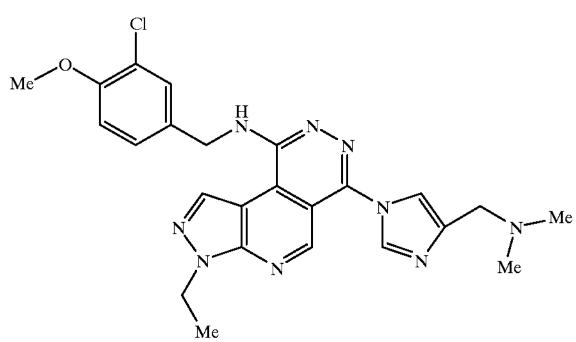 | 91 | 2.40 | m/z (M + H) 492 |
| 108 | 1-[9-[(4-methylcarboxylate)-N-1H-imidazole]-3-ethyl-3H-pyrazolo[4',3':5,6]-pyri-do-[3,4-d]pyridazin-6-yl]-3-Chloro-4-methoxyphenyl)methyl-amine | 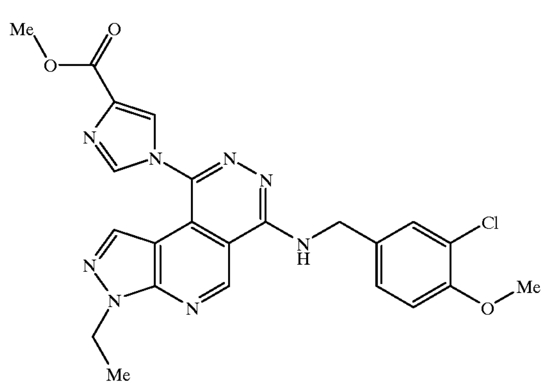 | 90 | 3.20 | m/z (M + H) 493 |

TABLE 1-continued

| NUMBER | NAME | STRUCTURE | PURITY (%) | HLPC (retention time, minutes) | OTHER DATA |
|---|---|---|---|---|---|
| 109 | 1-[9-[[(3-Chloro-4-methoxyphenyl)methyl]-amino]-3-ethyl-3H-pyrazolo[4',3':5,6]pyri-do-[3,4-d]pyridazin-6-yl]-N-1H-imidazole-4-(pentafluorophenolic carboxylate ester | 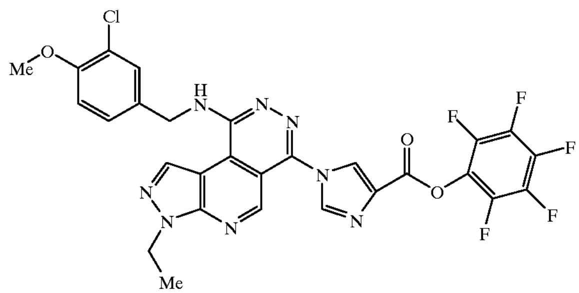 | 90 | 4.00 | m/z (M + H) 645 |
| 110 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N-cyclopentyl)piperizine | 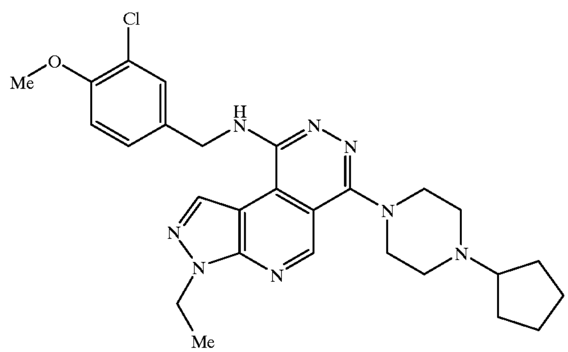 | 91 | 2.35 | m/z (M + H) 521 |
| 111 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N-isopropyl)piper-izine | 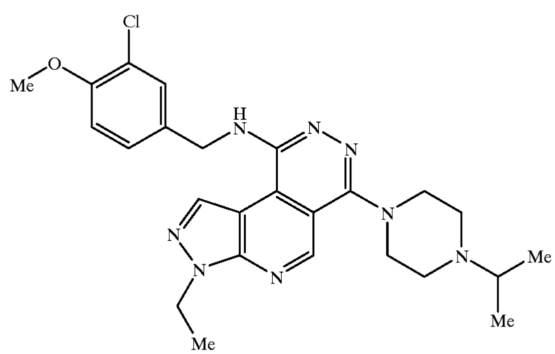 | 93 | 2.22 | m/z (M + H) 495 |
| 112 | 1-[9-[[(3-Chloro-4-methoxyphenyl)-methyl]amino]-3-ethyl-3H-pyrazolo[4',3':5,6]pyrido-[3,4-d]pyridazin-6-yl]-1-[4-(1-N-pyrrolidinyl)piper-idine | 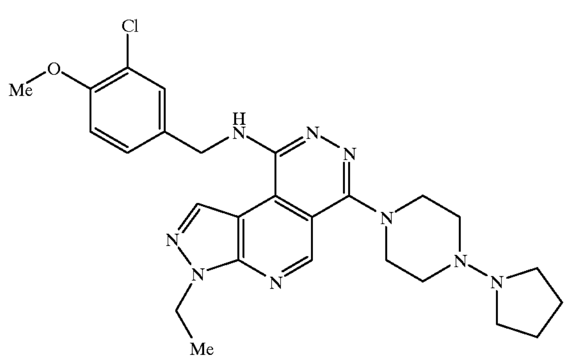 | 90 | 2.28 | m/z (M + H) 521 |

TABLE 1-continued

| NUMBER | NAME | STRUCTURE | PURITY (%) | HLPC (retention time, minutes) | OTHER DATA |
|---|---|---|---|---|---|
| 113 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N-ethylcarboxylate) piperizine | 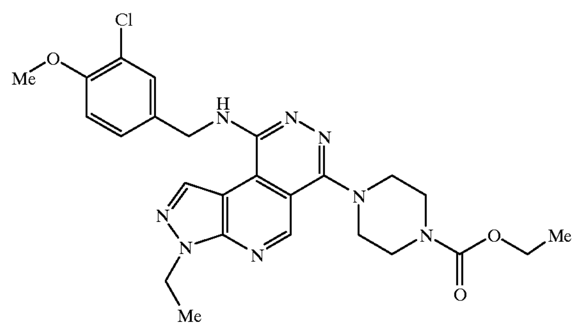 | 84 | 3.18 | m/z (M + H) 525 |
| 114 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N-methyl) diazopine | 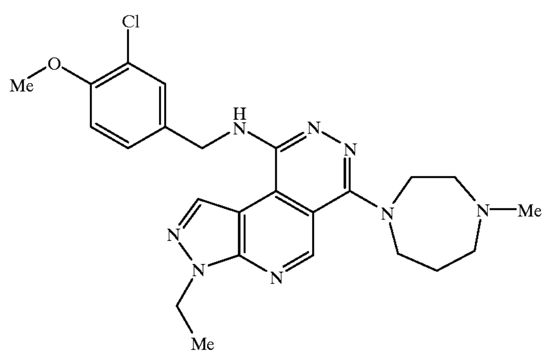 | 91 | 2.57 | m/z (M+ H) 481 |
| 115 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N-formyl piperidine | 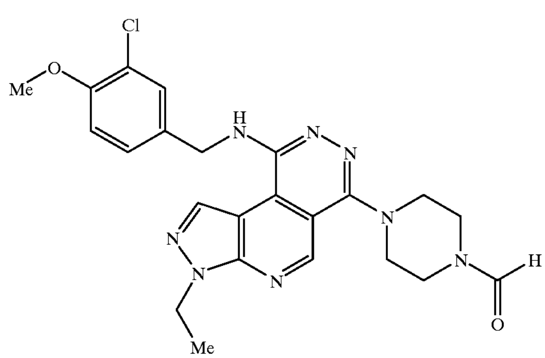 | 88 | 2.64 | m/z (M + H) 481 |
| 116 | 1-[9-[[(3-Chloro-4-methoxyphenyl)-methyl]amino]-3-ethyl-3H-pyrazolo[4',3':5,6]pyrido-[3,4-d]pyridazin-6-yl]-1-(4-N pipizinyl)-2-furfuryl-carboxamide | 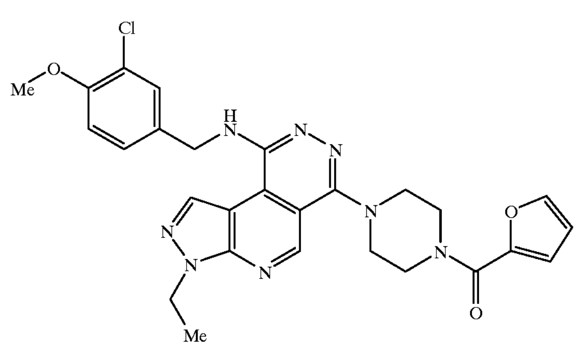 | 88 | 3.01 | m/z (M + H) 547 |

TABLE 1-continued

| NUMBER | NAME | STRUCTURE | PURITY (%) | HLPC (retention time, minutes) | OTHER DATA |
|---|---|---|---|---|---|
| 117 | 1-[9-[[(3-Chloro-4-methoxyphenyl)-methyl]amino]-3-ethyl-3H-pyrazolo[4',3':5,6]pyrido-[3,4-d]pyridazin-6-yl]-N-1H-imidazole-4-formaldehyde | 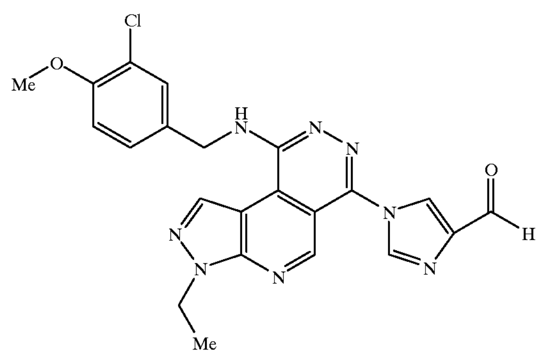 | 90 | 3.42 | m/z (M + H) 463 |
| 118 | 1-[9-[[(3-Chloro-4-methoxyphenyl)-methyl]amino]-3-ethyl-3H-pyrazolo[4',3':5,6]pyrido-[3,4-d]pyridazin-6-yl]-N-1H-imidazole-4-pyrrolidinyl carboxamide | 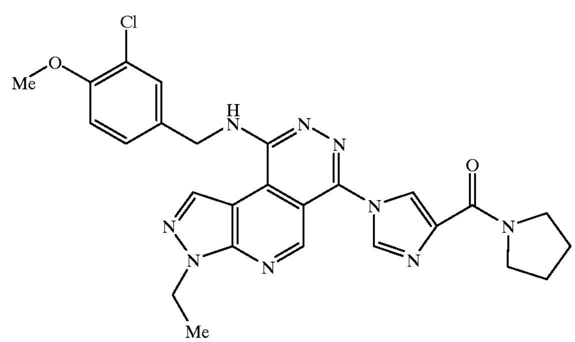 | 95 | 3.30 | m/z (M + H) 532 |
| 119 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(2,6-dimethylpiperizinyl) carboxamide | 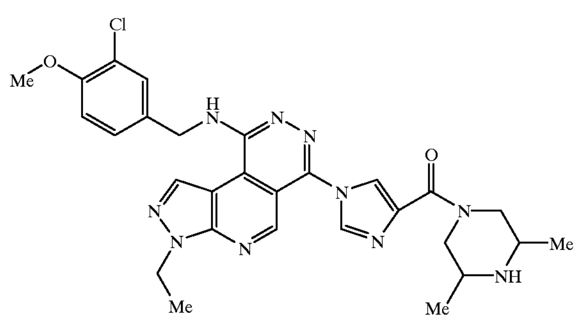 | 95 | 3.1 | m/z (M + H) 575 |
| 120 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-N,N-dimethyl hydrazide | 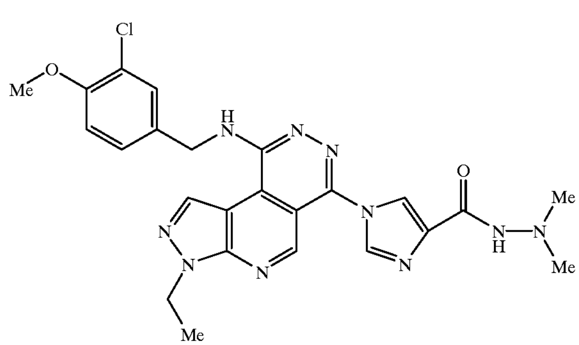 | 90 | 2.78 | m/z (M + H) 521 |

TABLE 1-continued

| NUMBER | NAME | STRUCTURE | PURITY (%) | HLPC (retention time, minutes) | OTHER DATA |
|---|---|---|---|---|---|
| 121 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(S-3-aminopyrrolidinyl) carboxamide | 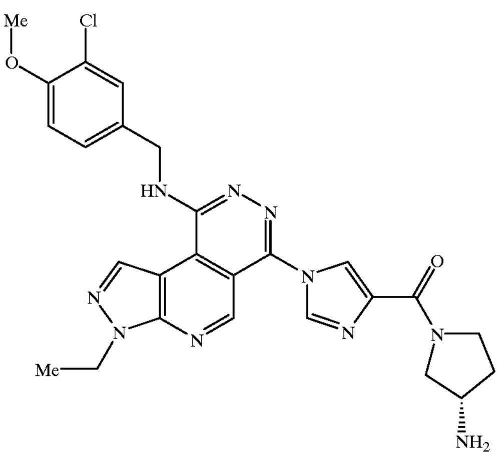 | 98 | 3.0 | m/z (M + H) 547 |
| 122 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(R-3-t-butoxycarbonyl-aminopyrrolidinyl carboxamide | 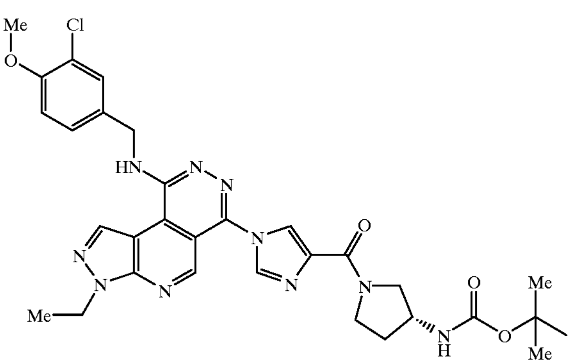 | 647 | 3.4 | m/z (M + H) 647 |
| 123 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(N'-methyl)hydrazide | 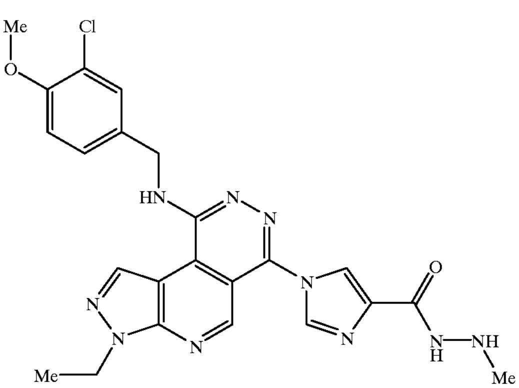 | 95 | 2.5 | m/z (M + H) 507 |

TABLE 1-continued

| NUMBER | NAME | STRUCTURE | PURITY (%) | HLPC (retention time, minutes) | OTHER DATA |
|---|---|---|---|---|---|
| 124 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-carboxylate guanidine | 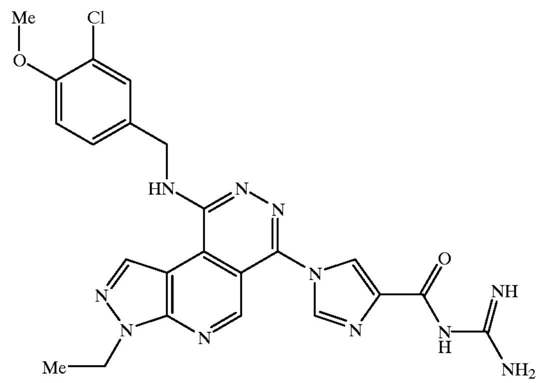 | 95 | 2.5 | m/z (M + H) 520 |
| 125 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(S-3-N,N-dimethylaminopyrrol-idinyl)carboxamide | 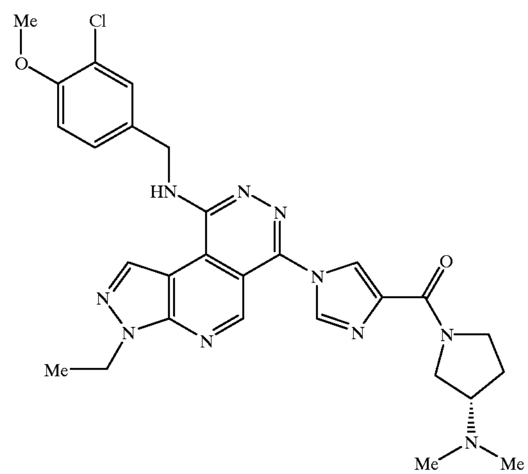 | 91 | 3.0 | m/z (M + H) 575 |
| 126 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-N-(S-3-t-butoxycarbonylamino-pyrrolidinyl)carboxamide | 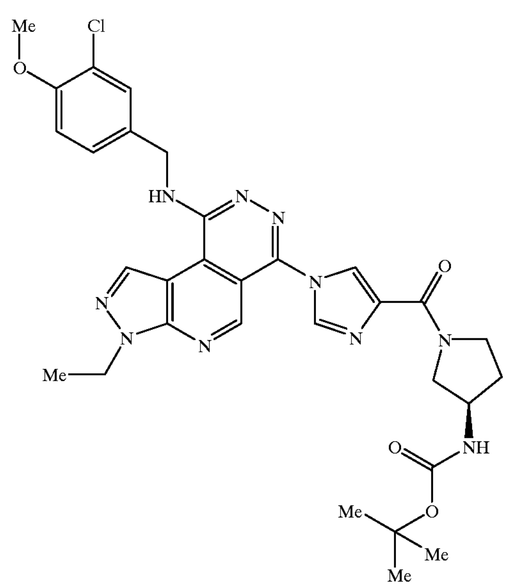 | 95 | 4.0 | m/z (M + H) 647 |

TABLE 1-continued

| NUMBER | NAME | STRUCTURE | PURITY (%) | HLPC (retention time, minutes) | OTHER DATA |
|---|---|---|---|---|---|
| 127 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(N,N-diethylethylenedi-amino)carboxamide | 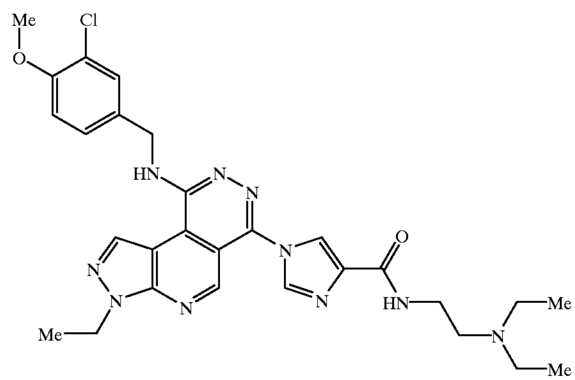 | 99 | 3.1 | m/z (M + H) 577 |
| 128 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(3-methylaminopyrroli-dinyl)carboxamide | 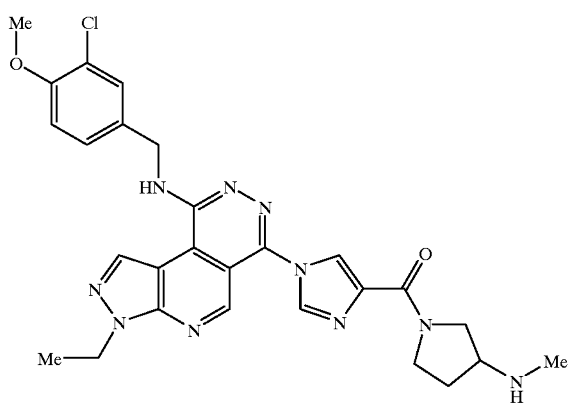 | 96 | 3.0 | m/z (M + H) 561 |
| 129 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-aminomorpholinyl)carboxamide | 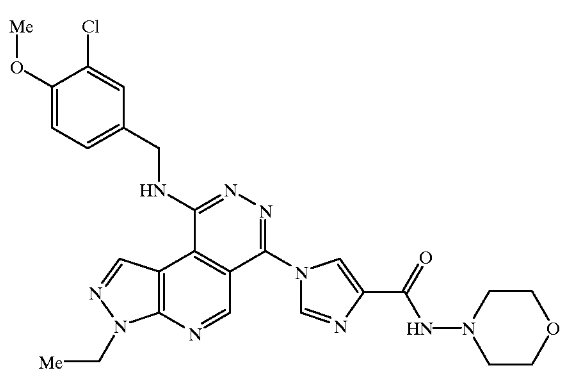 | 97 | 3.6 | m/z (M + H) 563 |

TABLE 1-continued

| NUMBER | NAME | STRUCTURE | PURITY (%) | HLPC (retention time, minutes) | OTHER DATA |
|---|---|---|---|---|---|
| 130 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(R-3-N,N-dimethylaminopyrrolidinyl)carboxamide | 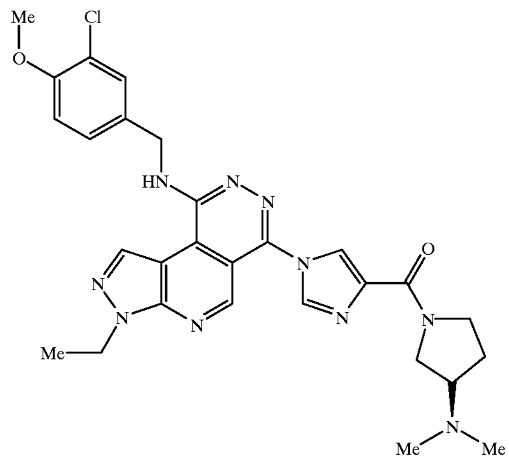 | 100 | 3.0 | m/z (M + H) 575 |
| 131 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(R-3-aminopyrrolidinyl)carboxamide | 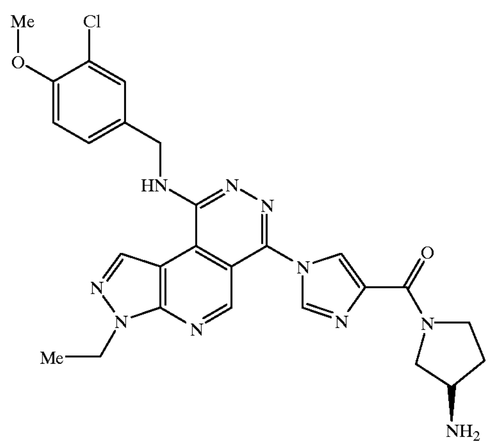 | 100 | 3.0 | m/z (M + H) 547 |
| 132 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1,4,5,6-tetrahydropyrimidinyl) carboxamide | 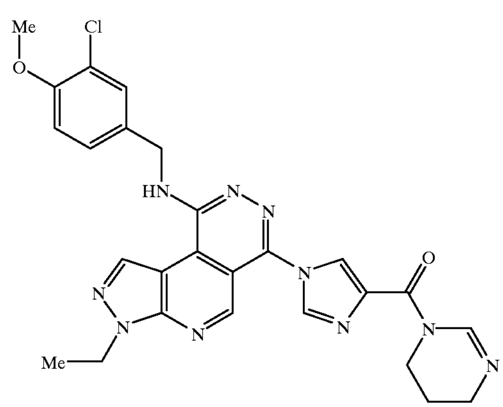 | 96 | 3.2 | m/z (M + H) 545 |

TABLE 1-continued

| NUMBER | NAME | STRUCTURE | PURITY (%) | HLPC (retention time, minutes) | OTHER DATA |
|---|---|---|---|---|---|
| 133 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-cyclopropylamino carboxamide | 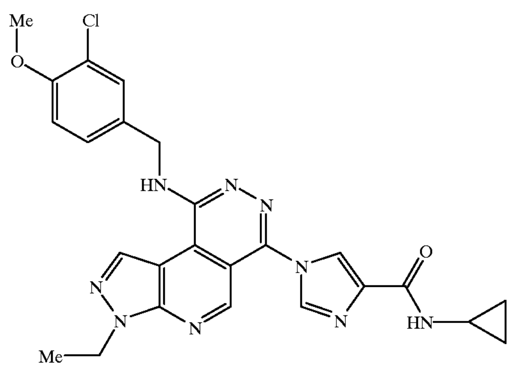 | 99 | 3.8 | m/z (M + H) 518 |
| 134 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(4,5-dihydro-4,4-dimethyl-1H-imidazol-1-yl) carboxamide | 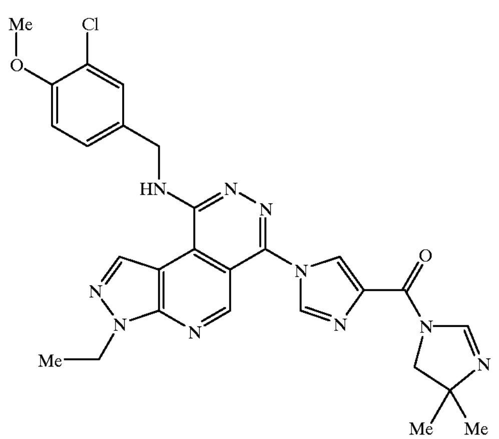 | 93 | 3.2 | m/z (M + H) 559 |
| 135 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(N-methyl)amidine | 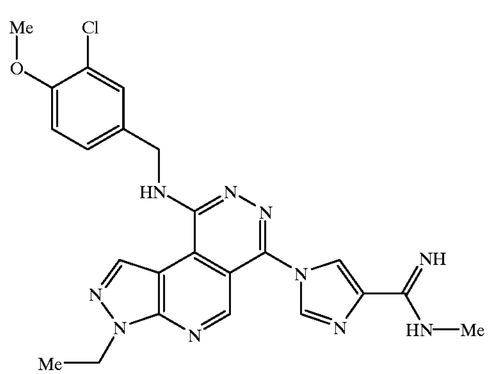 | 98 | 2.9 | m/z (M + H) 491 |

TABLE 1-continued

| NUMBER | NAME | STRUCTURE | PURITY (%) | HLPC (retention time, minutes) | OTHER DATA |
|---|---|---|---|---|---|
| 136 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(3-hydroxypyrrolidinyl)carboxamide | 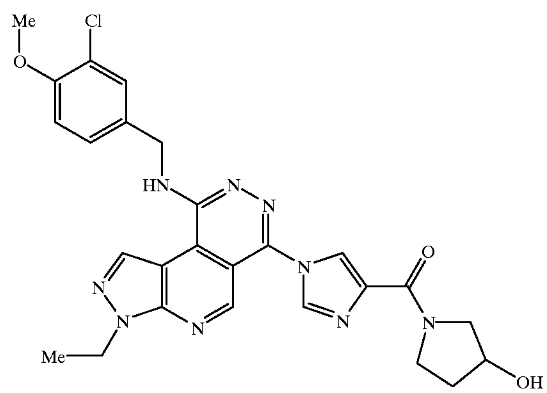 | 96 | 3.0 | m/z (M + H) 548 |
| 137 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-[R-1-amino-2(methoxymethyl)pyrrolidinyl)hydrazide | 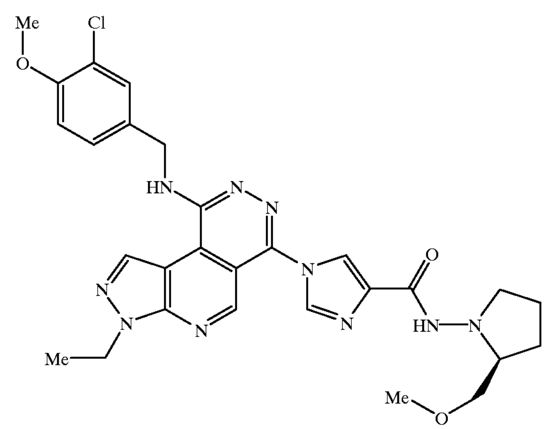 | 86 | 3.2 | m/z (M + H) 591 |
| 138 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-aminopyrrolindinyl)carboxamide | 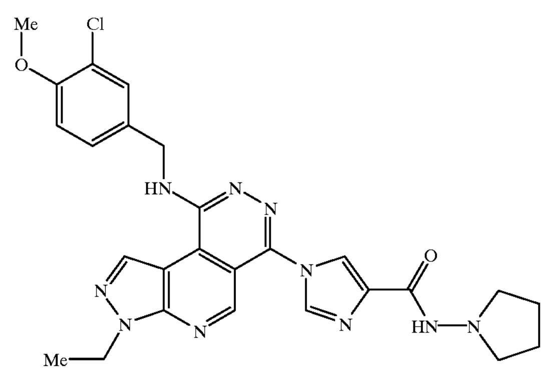 | 92 | 2.9 | m/z (M + H) 547 |

TABLE 1-continued

| NUMBER | NAME | STRUCTURE | PURITY (%) | HLPC (retention time, minutes) | OTHER DATA |
|---|---|---|---|---|---|
| 139 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(2-methyl-2-imidazolinyl) carboxamide | 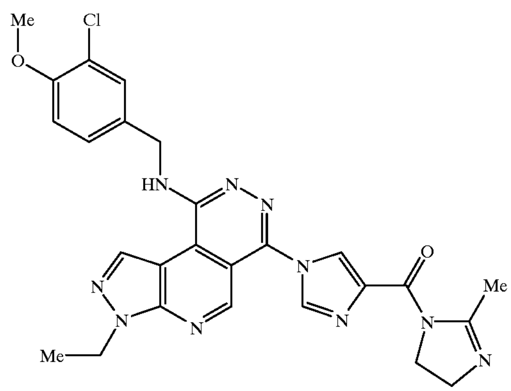 | 90 | 3.2 | m/z (M + H) 545 |
| 140 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(R-2-methoxymethyl-pyrrolidinyl) carboxamide | 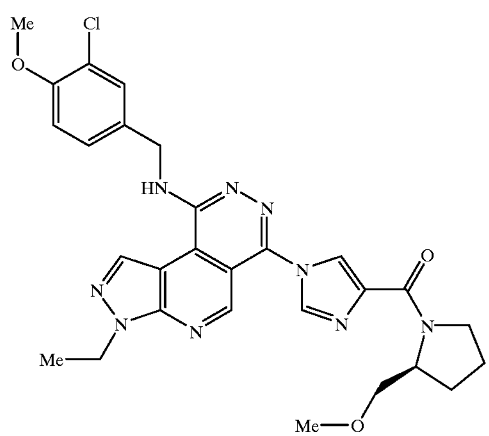 | 96 | 4.0 | m/z (M + H) 576 |
| 141 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-S-3-(pyrrolidinyl) amino carboxamide | 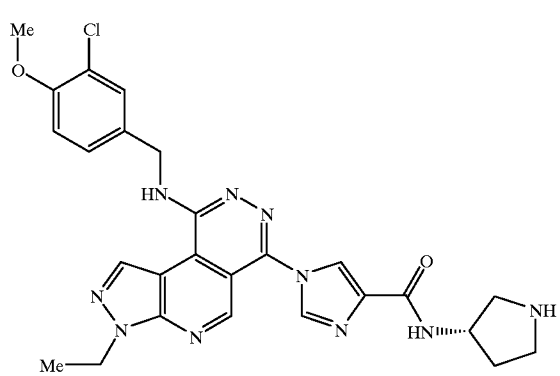 | 92 | 3.0 | m/z (M + H) 547 |

TABLE 1-continued

| NUMBER | NAME | STRUCTURE | PURITY (%) | HLPC (retention time, minutes) | OTHER DATA |
|---|---|---|---|---|---|
| 142 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-[S-1-(2-pyrrolidinylmethyl)pyrrolidinyl]carboxamide | 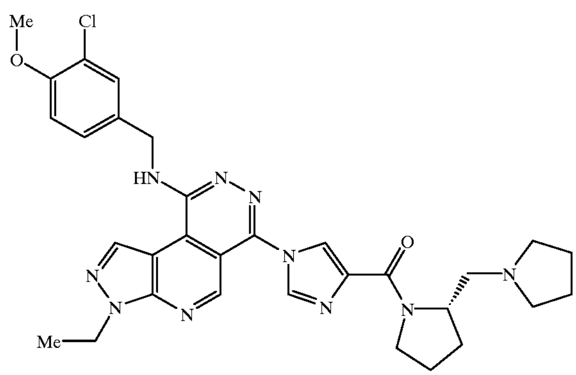 | 93 | 3.2 | m/z (M + H) 615 |
| 143 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(S-3-hydroxymethylpyrrolidinyl)carboxamide | 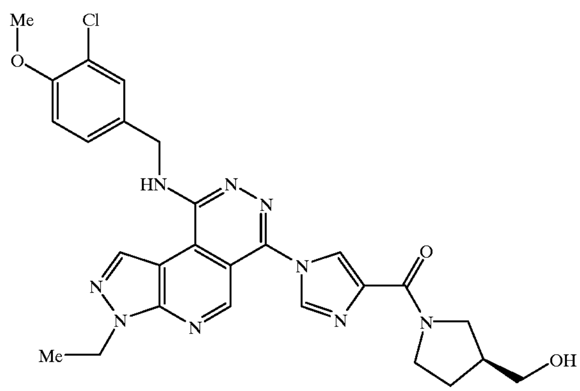 | 94 | 3.2 | m/z (M + H) 562 |
| 144 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(3-pyrrolinyl)carboxamide | 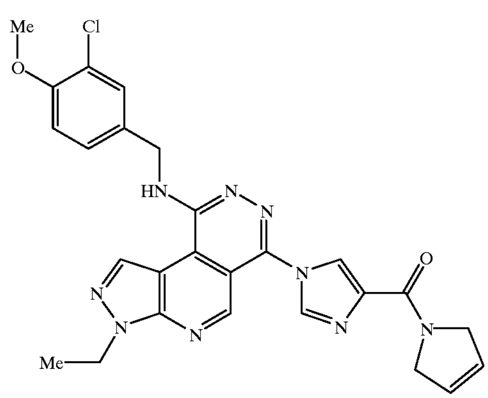 | 80 | 3.4 | m/z (M + H) 530 |

TABLE 1-continued

| NUMBER | NAME | STRUCTURE | PURITY (%) | HLPC (retention time, minutes) | OTHER DATA |
|---|---|---|---|---|---|
| 145 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(cis-3,4-dihydroxypyrrolidinyl) carboxamide | 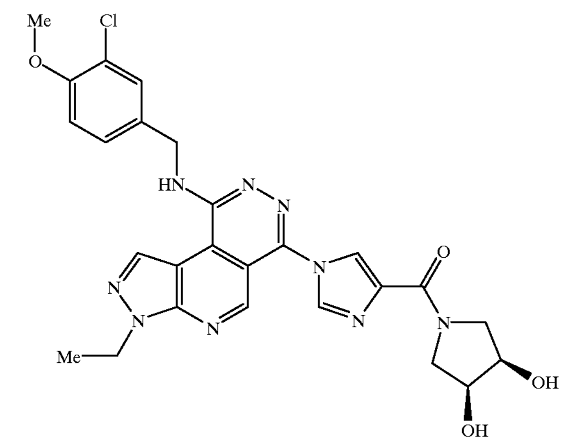 | 95 | 2.9 | m/z (M + H) 564 |
| 146 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-pyrazolyl) carboxamide | 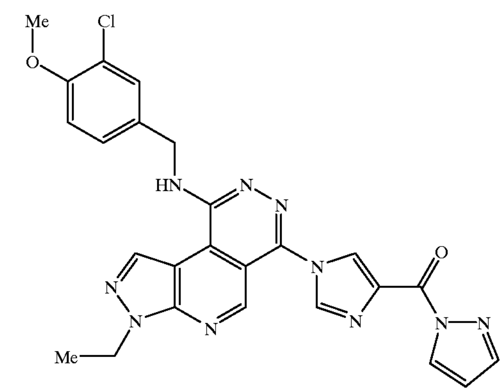 | 93 | 3.5 | m/z (M + H) 529 |
| 147 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(3-amino-hexahydro-2-azepinonyl) carboxamide | 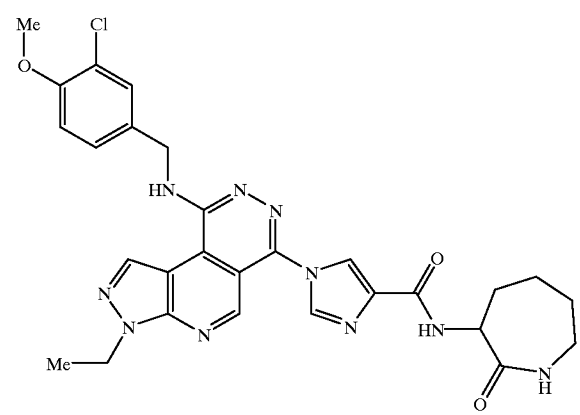 | 94 | 3.2 | m/z (M + H) 589 |

TABLE 1-continued

| NUMBER | NAME | STRUCTURE | PURITY (%) | HLPC (retention time, minutes) | OTHER DATA |
|---|---|---|---|---|---|
| 148 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-[1-(2,3,4,5-tetrahydropyrazolyl)]carboxamide | 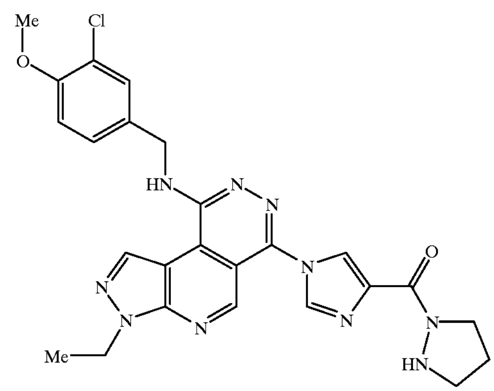 | 80 | 2.8 | m/z (M + H) 533 |
| 149 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-amino-ethylenediamino)carboxamide | 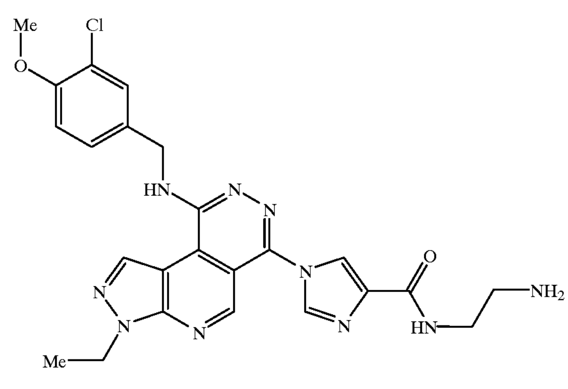 | 91 | 3.1 | m/z (M + H) 521 |
| 150 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-acetic acid | 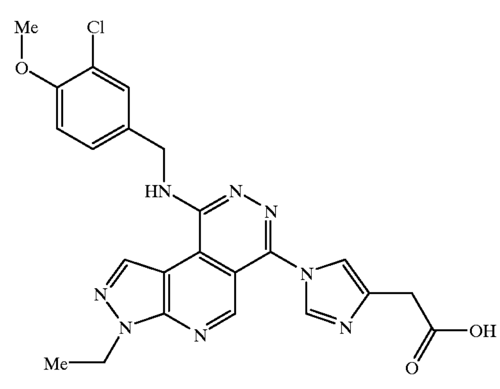 | 89 | 2.9 | m/z (M + H) 493 |

TABLE 1-continued

| NUMBER | NAME | STRUCTURE | PURITY (%) | HLPC (retention time, minutes) | OTHER DATA |
|---|---|---|---|---|---|
| 151 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-methylene-N-pyrrolidine | 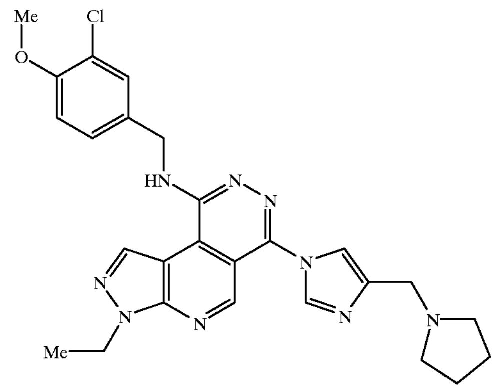 | 94 | 2.5 | m/z (M + H) 518 |
| 152 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-ethyl alcohol | 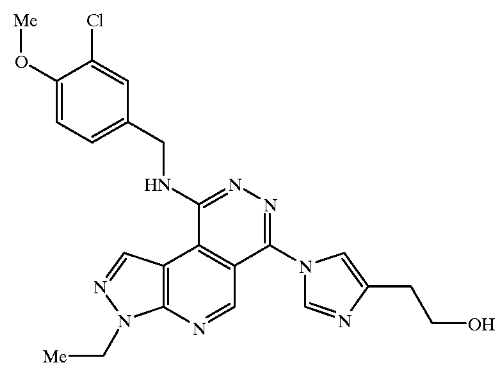 | 89 | 2.4 | m/z (M + H) 479 |
| 153 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(N-methanesulfonyl) carboxamide | 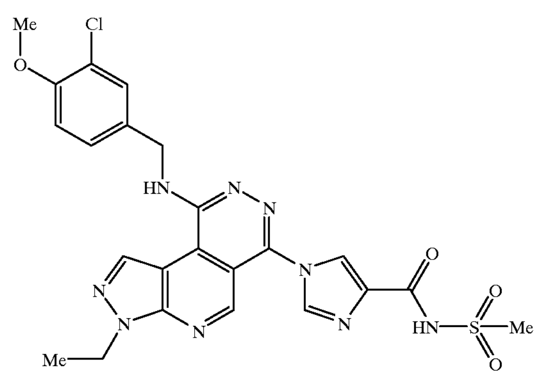 | 96 | 3.0 | m/z (M + H) 556 |
| 154 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-methyl acetylcarboxylate | 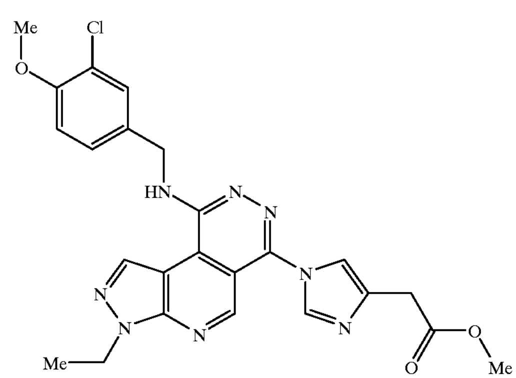 | 90 | 2.8 | m/z (M + H) 507 |

TABLE 1-continued

| NUMBER | NAME | STRUCTURE | PURITY (%) | HLPC (retention time, minutes) | OTHER DATA |
|---|---|---|---|---|---|
| 155 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-ethylamine | 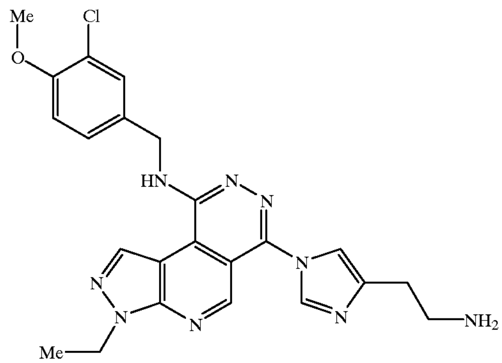 | 94 | 2.3 | m/z (M + H) 478 |
| 156 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-methylacetamide | 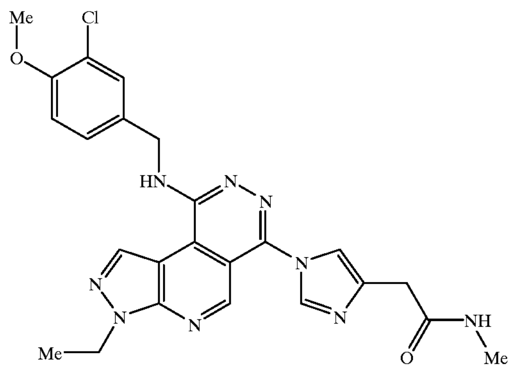 | 84 | 2.5 | m/z (M + H) 506 |
| 157 | 1-[9-[[(3-Chloro-4-methoxyphenyl)-methyl]amino]-3-ethyl-3H-pyrazolo[4',3':5,6]pyrido-[3,4-d]pyridazin-6-yl]-1H-imidazole-4-ethylamino phthalimide | 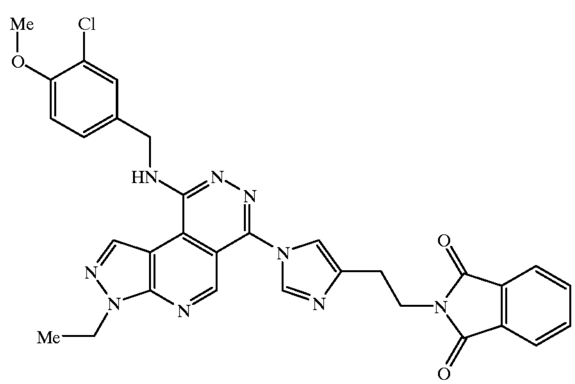 | 91 | 3.1 | m/z (M + H) 608 |
| 158 | 1-[9-[[(3-Chloro-4-methoxyphenyl)-methyl]amino]-3-ethyl-3H-pyrazolo[4',3':5,6]pyrido-[3,4-d]pyridazin-6-yl]-N-ω-histamine | 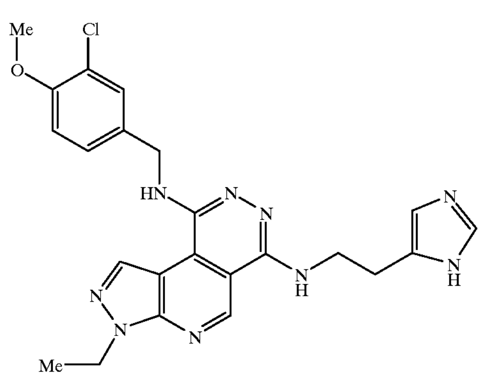 | 94 | 2.0 | m/z (M + H) 478 |

TABLE 1-continued

| NUMBER | NAME | STRUCTURE | PURITY (%) | HLPC (retention time, minutes) | OTHER DATA |
|---|---|---|---|---|---|
| 159 | 1-[9-[[(3-Chloro-4-methoxyphenyl)-methyl]amino]-3-ethyl-3H-pyrazolo[4',3':5,6]pyrido-[3,4-d]pyridazin-6-yl]-4-trans-aminocyclohexyl-1-carboxylic acid | 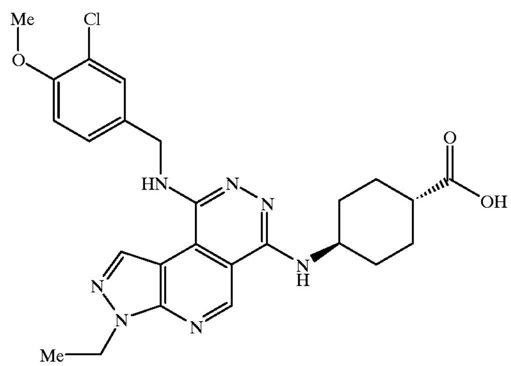 | 89 | 3.00 | m/z (M + H) 510 |
| 160 | 1-[9-[[(3-chloro-4-methoxyphenyl)-methyl]amino]-3-ethyl-3H-pyrazolo[4',3':5,6]pyrido-[3,4-d]pyridazin-6-yl]-4-trans-aminocyclohexyl-1-ethylcarboxylate | 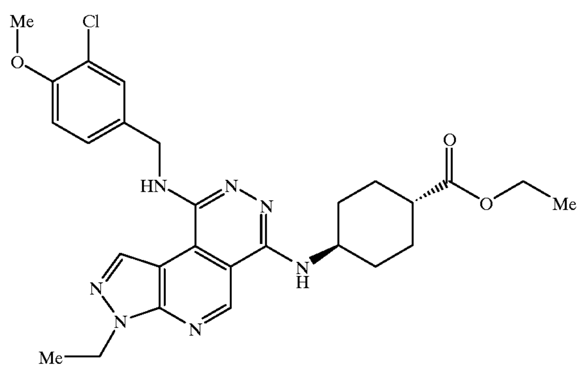 | 98 | 3.2 | m/z (M + H) 538 |
| 161 | 1-[9-[[(3-Chloro-4-methoxyphenyl)-methyl]amino]-3-ethyl-3H-pyrazolo[4',3':5,6]pyrido-[3,4-d]pyridazin-6-yl]-N-1H-imidazole-4-hydroxamid acid | 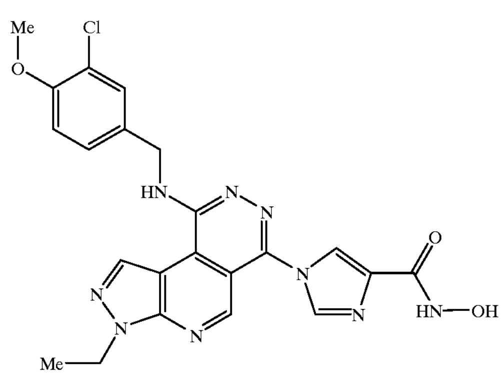 | 95 | 2.8 | m/z (M + H) 494 |

TABLE 1-continued

| NUMBER | NAME | STRUCTURE | PURITY (%) | HLPC (retention time, minutes) | OTHER DATA |
|---|---|---|---|---|---|
| 162 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-methyl carboxamide | 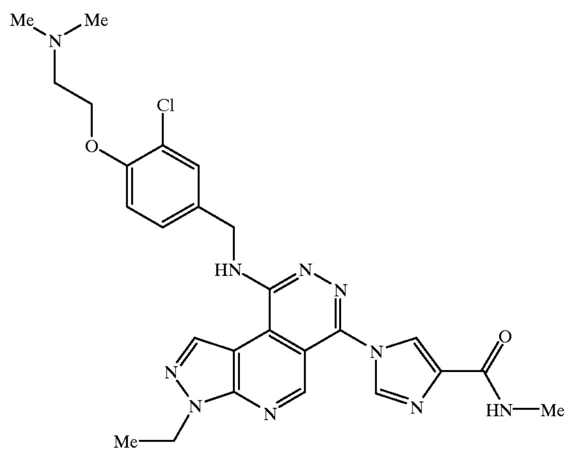 | 78 | 2.1 | m/z (M + H) 549 |
| 163 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-morpholinoethylene diamino) carboxamide | 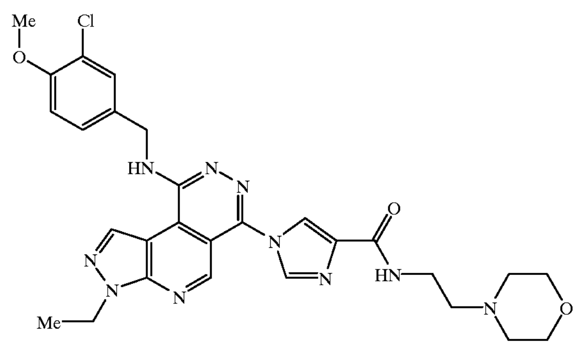 | 90 | 2.5 | m/z (M + H) 591 |
| 164 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-(1-pyrrolidino ethylenediamino) carboxamide | 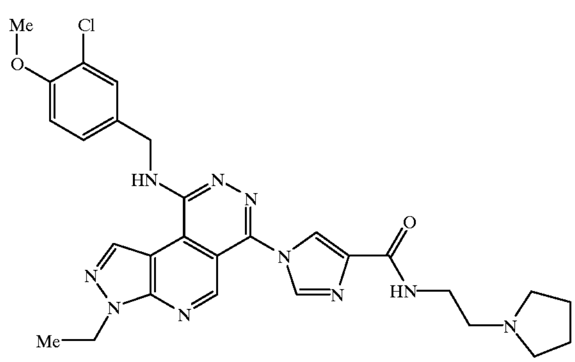 | 93 | 2.5 | m/z (M + H) 575 |

TABLE 1-continued

| NUMBER | NAME | STRUCTURE | PURITY (%) | HLPC (retention time, minutes) | OTHER DATA |
|---|---|---|---|---|---|
| 165 | 1-[9-[[(3-Chloro-4-methoxyphenyl)-methyl]amino]-3-ethyl-3H-pyrazolo[4',3':5,6]pyrido-[3,4-d]pyridazin-6-yl]-N-1H-imidazole-4-carboxamide | 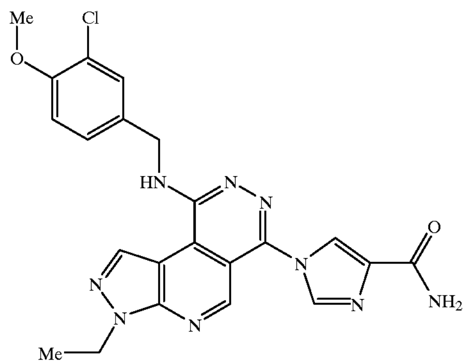 | 91 | 3.0 | m/z (M + H) 478 |
| 166 | 1-[9-[[(3-Chloro-4-methoxyphenyl)-methyl]amino]-3-ethyl-3H-pyrazolo[4',3':5,6]pyrido-[3,4-d]pyridazin-6-yl]-N-1H-imidazole-4-acetylhydroxamic acid | 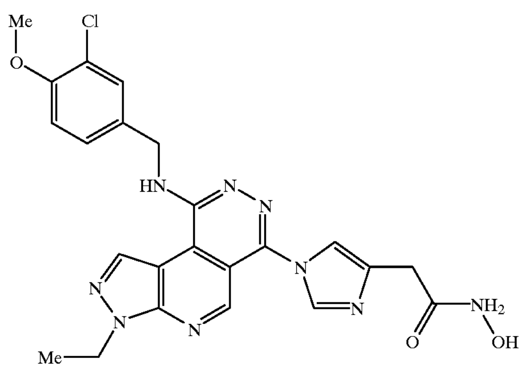 | 88 | 2.3 | m/z (M + H) 508 |
| 167 | 1-[9-[[(3-chloro-4-methoxyphenyl)-methyl]amino]-3-ethyl-3H-pyrazolo[4',3':5,6]pyrido-[3,4-d]pyridazin-6-yl]-N-2-aminopyridine | 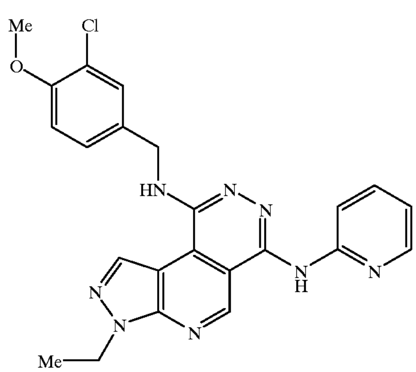 | 90 | 2.7 | m/z (M + H) 461 |
| 168 | 1-[9-[[(3-chloro-4-methoxyphenyl)-methyl]amino]-3-ethyl-3H-pyrazolo[4',3':5,6]pyrido-[3,4-d]pyridazin-6-yl]-1H-imidazole-4-ethylene-N-morpholine | 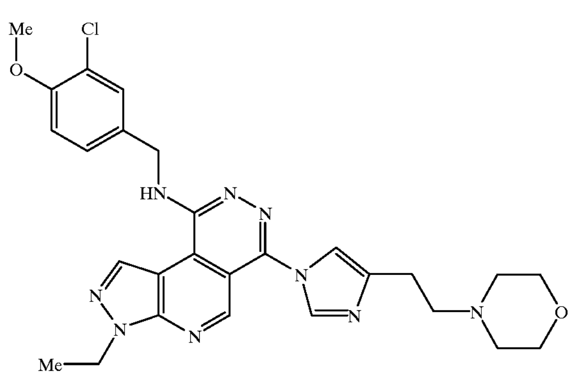 | 80 | 2.0 | m/z (M + H) 548 |

TABLE 1-continued

| NUMBER | NAME | STRUCTURE | PURITY (%) | HLPC (retention time, minutes) | OTHER DATA |
|---|---|---|---|---|---|
| 169 | 1-[9-[[(3-chloro-4-methoxyphenyl)methyl]amino]-3-ethyl-3H-pyrazolo[4',3':5,6]pyrido-[3,4-d]pyridazin-6-yl]-1H-imidazole-4-(2-N,N-dimethylethylenediamino)acetamide | 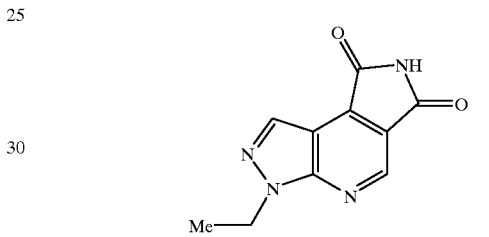 | 92 | 2.1 | m/z (M + H) 563 |

EXAMPLE 170

1-[9-[[(3-Chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide

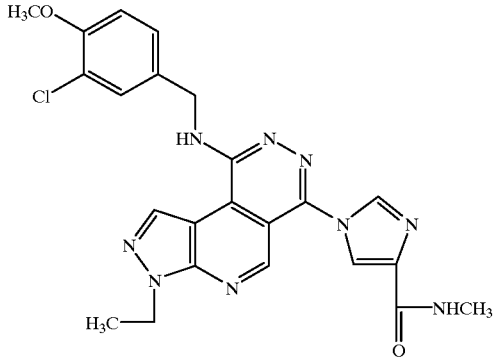

a) (1-Ethylpyrazol-5-ylamino)-N,N-dimethylformamidine

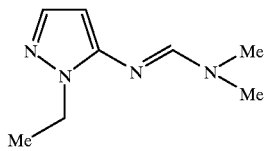

A neat solution of 5-amino-1-ethylpyrazole (60.0 g, 540.5 mmol) and N,N-dimethylformamide-dimethoxyacetal (84.0 mL, 594.5 mmol) was heated at reflux for 5 h. The resulting brown solution was considered 100% converted and was used directly in the following reaction.

b) 3-Ethyl-3H-pyrazolo[4',3':5,6]pyrido[3,4-d]succinamide-6,8-dione

To a solution of (1-Ethylpyrazol-5-ylamino)-N,N-dimethylformamidine (540.5 mmol) in water (200 mL) in a beaker (2.0 L) was added maleimide (131.0 g, 1350.0 mmol) dissolved in water (700 mL). This solution was stirred vigrously at r.t. for 12 h while air was bubbled through rapidly. The light yellow solid was collected by filtration and rinsed thoroughly with water. This material was >97% as judged by HPLC (79.0 g, 65% for 2 steps after oven drying) and was used directly for the following reaction.

c) 3-Ethyl-7,8-dihydro-3H-pyrazolo[4',3':5,6]pyrido[3,4-d]pyridazine-6,9-dione (See Preparations 9 and 10)

To a suspension of 3-Ethyl-3H-pyrazolo[4',3':5,6]pyrido[3,4-d]succinamide-6,8-dione (79.0 g, 366.0 mmol) in 1:1 ethanol-water (1 L) was added hydrazine monohydrate (50 mL, 1000 mmol). The resulting yellow solution was heated to reflux for 0.5 h and cooled to ~40° C. The yellow solution was acidified with HCl (conc.) to pH~4. White suspension was formed. The thick suspension was cooled to r.t. before being filtered. The white solid was dried at 40° C. vacuum oven for 24 h (72.0 g, 311.0 mmol). This material was transformed to 6,9-Dichloro-3-ethyl-3H-pyrazolo[4',3':5,6]pyrido[3,4-d]pyridazine as discussed in Preparation 10 and subsequently used in the following reactions.

d) N-Methyl-1-(9-chloro-3-ethyl-3H-pyrazolo[4',3':5,6]pyrido[3,4-d]pyridazin-6-yl)imidazole-4-carboximide To a suspension of 6,9-dichloropyrazolo-pyridopyridazine (30.0 g, 112.0 mmol) in N-methylpyrrolidinone (300 mL) in a 1 L pressure glass reactor was added 4-methylimidazolecarboxamide (14.7 g, 118.0 mmol) and diisopropylethylamine (58.0 mL, 336.0 mmol). The reaction mixture was placed in a preheated oil bath at 105° C. for 2 hours. The content was poured onto ice (approximately 1 kg). Unreacted 6,9-dichloropyrazolopyridopyridazine precipitated as a light yellow solid and was collected by filtration. Diethyl ether (500 mL) was used to extract the aqueous solution once to further remove the 6,9-dichloropyrazolo-pyridopyridazine. The aqueous solution was then saturated with ammonium sulfate followed by the extraction with ethyl acetate (3×1 L). The combined organic portions were washed with water (2×1 L) and dried over anhydrous sodium sulfate. The solvent was subsequently removed under reduced pressure. The resulting solid was 80% pure as judged by reverse phase HPLC and LC-MS (m/z 358) and was used without further purification. The yield was 20% after correcting for the purity.

e) 1-[9-[[(3-Chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide To a suspension of the product from step (d) (26.5 g, 74.0 mmol) in N-methylpyrrolidinone (265 mL) in a 1 L pressure glass reactor was added (3-chloro-4-methoxyphenyl) methylamine hydrogen chloride (18.7 g, 89.0 mmol) and diisopropylethylamine (43.0 mL, 244.0 mmol). The reaction mixture was placed in a preheated oil bath at 120° C. for 2 hours. The content was poured onto ice (approximately 1 kg) and a light yellow solid formed. The aqueous suspension was allowed to stand at room temperature for 20 minutes and then filtered. The solid was washed with water thoroughly. This wet solid was dissolved in ethanol (75 mL) and was subsequently heated to boiling. White solid began to form and became a thick slurry. The suspension was cooled briefly at room temperature and was filtered. The solid was resuspended in ethanol (50 mL) and was heated to boiling for 10 minutes and filtered. The product was obtained as a white solid (22.5 g, 62% yield) with a purity of 99% as judged by reverse phase HPLC: mp 181–183° C. and 206–207° C.; LRMS m/z 491; $^{13}$C NMR (CDCl$_3$), δ 162.7, 154.2, 149.3, 146.2, 143.0, 138.4, 137.3, 131.1, 130.6, 129.9, 127.6, 122.8, 122.5, 118.1, 113.8, 112.3, 104.1, 99.9, 56.2, 45.6, 43.3, 25.8, 15.0. Anal. Calcd for C$_{23}$H$_{22}$ClN$_9$O$_2$: C, 56.16; H, 4.51; N, 25.63; Cl, 7.21. Found: C, 55.72; H, 4.32; N, 25.94; Cl, 7.23.

Steps b), d) and e) in the above synthesis were also carried out by the following preferred procedure.

b') 3-Ethyl-3H-pyrazolo[4',3':5,6]pyrido[3,4-d]succinamide-6,8-dione

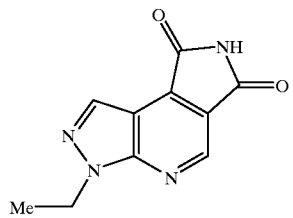

To a solution of (1-Ethylpyrazol-5-ylamino-N,N-dimethylformamidine (540.5 mmol) in water (200 mL) in a beaker (2.0 L) was added maleimide (131.0 g, 1350.0 mmol) dissolved in water (700 mL). This solution was stirred vigrously at r.t. for 12 h while air was bubbled through rapidly. The light yellow solid was collected by filtration and rinsed thoroughly with water. This material was >97% as judged by HPLC (79.0 g, 65% for 2 steps after oven drying) and was used directly for the following reaction.

c') This step was identical to step c) above.

d') N-Methyl-1-(9-chloro-3-ethyl-3H-pyrazolo[4',3':5,6]pyrido[3,4-d]pyridazin-6-yl) imidazole-4-carboximide A solution of 4-methylimidazolecarboxamide (5.3 g, 42.1 mmol) in N,N-dimethylformamide (20 mL) was prepared. In a 1 L, 3-neck jacketed reactor vessel, a slurry of 6,9-dichloropyrazolo-pyridopyridazine (10.0 g, 37.3 mmol) in N,N-dimethylformamide (40 mL) was cooled to 0–2° C. To the above mixture, was added 10% of the 4-methylimidazolecarboxamide solution over 15 min. followed by the addition of 325 mesh K$_2$CO$_3$ (15.3 g, 111.7 mmol). The resulting mixture was stirred vigorously at 2–4° C. The remaining 4-methylimidazolecarboxamide solution was added over 6 h and additional 325 mesh K$_2$CO$_3$ (2×7.6 g, 111.7 mmol) was added in two portions at 3 h intervals. After stirring for 7 h at 2–4° C., the reaction mixture was warmed up to 10° C. and stirred for another 16 h at this temperature. A thick slurry was formed. The reaction was stopped when the remaining 6,9-dichloropyrazolo-pyridopyridazine was less than 8%, quantified by HPLC analysis of a sample filtrate.

Cold water (120 ml) was slowly added into the agitated reaction mixture. The temperature of the mixture was maintained below 25° C. throughout the addition. After 1 h stirring, the mixture was filtered through a medium poresity glass frit. The solid cake was washed by slurrying with DMF/H$_2$O (1/4, 3×30 mL) and H$_2$O (50 mL). The cake was dried in a vacuum oven (25"Hg vacuum, 50° C.) over 1–2 days to a constant weight. The weight of the crude solid was 8.7 g with 85% purity.

The crude solid was dissolved in N,N-dimethylformamide (60 mL) at 120–123° C. The solution was slowly cooled to 90° C. and stirred for 2 h at this temperature to form a seed bed. At 65–70° C., to the mixture was added EtOAc (60 mL) over 30 min. The mixture was slowly cooled to 25° C. over 3–4 h and stirred at room temperature for 16–20 h. The solid was collected on a medium poresity glass frit and washed with EtOAc (2×30 mL) to afford an off-white solid in 5.8 g, 43% yield. This material has a purity of 97.4% by HPLC analysis and LC-MS (m/z 358).

e') 1-[9-[[(3-Chloro-4-methoxyphenyl)methyl]amino]-3-ethyl-3H-pyrazolo-[4',3':5,6]pyrido[3,4-d]pyridazin-6-yl]-N-methyl-1H-imidazole-4-carboxamide To a suspension of the product from step (d) (26.5 g, 74.0 mmol) in N-methylpyrrolidinone (185 mL) in a 1 L pressure glass reactor was added (3-chloro-4-methoxyphenyl) methylamine hydrogen chloride (18.7 g, 89.0 mmol) and duisopropylethylamine (43.0 mL, 244.0 mmol). The reaction mixture was placed in a preheated oil bath at 110° C. for 4 hours. The reaction mixture was cooled to room temperature and 370 ml of water was added slowly over a period of 30 minutes. The aqueous suspension was allowed to stir at room temperature for 2 hours and then filtered. The solid was washed with water thoroughly and suction dried overnight. This solid was suspended in ethanol (330 ml) and heated to boiling for 5 hours. The suspension was cooled to 0–5° C., stirred for 2 hours and was filtered. The product was obtained as a pale yellow solid (33.2 g, 91% yield) with a purity of 99% as judged by reverse phase HPLC: mp 181–183° C. and 206–207° C.; LRMS m/z 491; $^{13}$C NMR (CDCl$_3$), δ 162.7, 154.2, 149.3, 146.2, 143.0, 138.4, 137.3, 131.1, 130.6, 129.9, 127.6, 122.8, 122.5, 118.1, 113.8, 112.3, 104.1, 99.9, 56.2, 45.6, 43.3, 25.8, 15.0. Anal. Calcd for C$_{23}$H$_{22}$ClN$_9$O$_2$: C, 56.16; H, 4.51; N, 25.63; Cl, 7.21. Found: C, 55.72; H, 4.32; N, 25.94; Cl, 7.23.

EXAMPLE 171

1-[9-[[(3-Chloro-4-methoxyphenyl)methyl]amino]-3-ethyl-3H-prazolo[4',3':5,6]pyrido[3,4-d]pyridazin-6-yl]-N-methyl-1H-imidazole-4-carboxamide, methanesulfonate (1:1)

To a suspension of the product from Example 170 (10.0 g, 20.3 mmol) in ethanol (200 mL) was added methanesulfonic acid (4.5 mL, 69.3 mmol) at 20° C. while stirring. The yellow slurry became thinner first and gradually turned into a thick off-white slurry. The slurry was stirred at 25° C. for 15 h, and DSC analysis on a filtered wet sample showed a melt endotherm at ~235° C. The slurry was stirred at r.t. for 0.5 h and filtered. The filter cake was washed with 300 mL of ethanol and dried at 45° C. vacuum oven for 24 h. The product was obtained as a pale yellow solid (11.4 g, 95% yield) with a HPLC purity of 99%; mp 233–235° C.; moisture LOD 3.9%; Anal. Calcd for $C_{23}H_{22}ClN_9O_2 \cdot CH_4SO_3$: C, 49.02; H, 4.46; N, 21.44; Cl, 6.03; S, 5.45. Found: C, 47.44; H, 4.81; N, 21.51; Cl, 5.78; S, 5.38.

EXAMPLE 172

1-[9-[[(3-Chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide, hydrobromide(1:1)

To a suspension of the product from Example 170 (1.0 g, 2.0 mmol) in ethanol (16.6 mL) was added hydrobromic acid solution (30 wt % in acetic acid, 2.0 mL, 10.0 mmol) at 20° C. while stirring. The yellow slurry was stirred at r.t. for 3 h, and DSC analysis on a filtered wet sample showed a melt endotherm at ~260° C. The slurry was filtered, and the filter cake was washed with 40 mL of ethanol and dried at 45° C. vacuum over for 24 h. The product was obtained as a pale yellow solid (1.1 g, 92% yield) with a HPLC purity of 99%; mp 244–248° C.; Anal. Calcd for $C_{23}H_{22}ClN_9O_2 \cdot HBr$: C, 48.22; H, 4.05; N, 22.01; Cl, 6.19; Br, 13.95. Found: C, 48.02; H, 3.98; N, 21.87; Cl, 6.13; Br, 13.83.

EXAMPLE 173

1-[9-[[(3-Chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide, hydrochloride(1:1)

To a suspension of the product from Example 170 (1.7 g, 3.5 mmol) in ethanol (35 mL) was added hydrochloric solution (37 wt % in water, 1.4 mL, 16.9 mmol) at 20° C. while stirring. The yellow slurry was heated to reflux for 1 h. A thick off-white slurry was gradually formed. The slurry was cooled to r.t., stirred for 20 h and filtered. The filter cake was washed with 40 mL of ethanol and dried at 45° C. vacuum oven for 24 h. The product was obtained as a pale yellow solid (1.8 g, 95% yield) with a HPLC purity of 99%; mp 202–208° C.; Anal. Calcd for $C_{23}H_{22}ClN_9O_2 \cdot HCl$: C, 52.28; H, 4.39; N, 23.86; Cl, 13.42. Found: C, 52.05; H, 4.41; N, 23.61; Cl, 13.09.

What is claimed is:

1. A compound of the formula

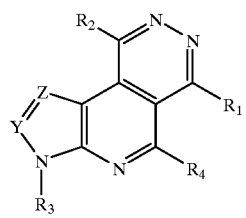

(I)

or a pharmaceutically acceptable salt thereof wherein:

Y is nitrogen or —C($R_5$)—;

Z is nitrogen or —C($R_6$)— provided that at least one of Y and Z is nitrogen;

$R_1$ and $R_2$ are independently selected from the group consisting of hydrogen, chloro, —$SR_7$, —$OR_7$, —$NR_8R_9$, and

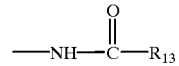

with the proviso that at least one of $R_1$ or $R_2$ is —$NR_8R_9$;

$R_3$ is hydrogen, alkyl, substituted alkyl, arylalkyl, or substituted arylalkyl;

$R_4$ is hydrogen, halogen, alkyl, substituted alkyl, —$OR_{10}$, or —$NR_{11}R_{12}$;

$R_5$ and $R_6$ are independently selected from the group consisting of hydrogen, halogen, alkyl or substituted alkyl;

$R_7$, $R_8$, and $R_9$ are independently selected from the group consisting of hydrogen, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl and heteroarylalkyl;

$R_8$ and $R_9$ together with the N atom to which they are attached can form a heterocyclo ring, a substituted or unsubstituted imidazole, a substituted or unsubstituted pyrazole, or a substituted or unsubstituted triazole;

$R_{10}$, $R_{11}$ and $R_{12}$ are independently selected from the group consisting of hydrogen, alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl and heteroarylalkyl;

$R_{13}$ is alkyl, substituted alkyl, cycloalkyl, substituted cycloalkyl, cycloalkylalkyl, substituted cycloalkylalkyl, aryl, substituted aryl, arylalkyl, substituted arylalkyl, heterocyclo, heterocycloalkyl, heteroaryl, or heteroarylalkyl;

the term "substituted alkyl" refers to straight or branched chain groups of 1 to 12 carbons having one, two, or three substituents selected from the group consisting of halo, —(CH$_2$)$_m$-hydroxy, cyano, alkoxy, alkylthio, amino, —NH(alkyl), —NH(cycloalkyl), —N(alkyl)$_2$, —C(O)—NH$_2$, —C(O)—NH(alkyl), —C(O)—N-(alkyl)$_2$, carboxy, and —CO$_2$-alkyl;

the terms "substituted cycloalkyl" and "substituted cycloalkylalkyl" refer to cycloalkyl rings having one, two, or three substituents selected from the group consisting of alkyl, alkoxy, alkylthio, halo, hydroxy, cyano, amino, —NH(alkyl), —NH(cycloalkyl), —N(alkyl)$_2$, —C(O)—NH$_2$, —C(O)—NH(alkyl), —C(O)—N(alkyl)$_2$, carboxy, —CO$_2$-alkyl, aryl, substituted aryl, arylalkyl, substituted arylalkyl, heterocyclo, heterocycloalkyl, heteroaryl, heteroarylalkyl, keto, =N—OH, =N—O-lower alkyl, and a five or six membered ketal;

the terms "substituted aryl" and "substituted arylalkyl" refer to aryl rings having one, two, or three substituents selected from the group consisting of alkyl, substituted alkyl, alkoxy, alkylthio, cycloalkyl, halo, hydroxy, nitro, cyano, amino, —NH(alkyl), —NH(cycloalkyl), —N(alkyl)₂, carboxy, —CO₂-alkyl, —C(O)—NH₂, —C(O)—NH(alkyl), —C(O)—NH(cycloalkyl), —C(O)—N(alkyl)₂, carboxy, —CO₂-alkyl, —C(O)-alkyl, —O—C(O)-alkyl, —NH—CH₂-carboxy, —NH—CH₂—CO₂-alkyl, phenyl, benzyl, phenylethyl, phenyloxy, phenylthio, heterocyclo, heterocycloalkyl, heteroaryl, and heteroarylalkyl, and pentafluorophenyl;

the terms "heterocyclo" and "heterocycloalkyl" refer to substituted and unsubstituted saturated or partially saturated 3 to 7 membered monocyclic groups, 7 to 11 membered bicyclic groups, and 10 to 15 membered tricyclic groups provided that said monocyclic group or at least one of said bicyclic or tricyclic groups contains one or two oxygen or sulfur atoms and/or from one to four nitrogen atoms provided that the total number of heteroatoms in each ring is four or less and further provided that said ring contains at least one carbon atom, the fused rings completing said bicyclic and tricyclic groups may contain one carbon atoms and may be saturated, partially saturated or unsaturated, said nitrogen and sulfur atoms may be oxidized and said nitrogen atoms may be quaternized, said heterocyclo ring is attached at any available nitrogen or carbon atom of any of said rings, and said heterocyclo ring may contain one, two or three substituents selected from the group consisting of halo, formyl, amino, cyano, alkyl, substituted alkyl, cycloalkyl, substituted cycloalkyl, —NH(alkyl), —NH(cycloalkyl), —NH (substituted alkyl), —N(alkyl)₂, alkoxy, alkylthio, hydroxy, nitro, phenyl, substituted phenyl, phenylalkyl, substituted phenyl-alkyl, phenyloxy, phenylthio, carboxy, —CO₂-alkyl, —C(O)NH-substituted alkyl, —C(O)—NH₂, —C(O)—NH(alkyl), —NH—CO₂-alkyl, —C(O)—NH(cycloalkyl), —C(O)—N(alkyl)₂, —C(O)-alkyl, —C(O)-aryl, —C(O)-substituted aryl, —C(O)-heteroaryl, —C(O)-heterocyclo; —O—C(O)-alkyl, —NH—CH₂-carboxy, —NH—CH₂—CO₂-alkyl, heterocyclo, heteroaryl, heteroarylalkyl, keto, =N—OH, =N—O-lower alkyl, and a five or six membered ketal;

the terms "heteroaryl" and "heteroarylalkyl" refers to substituted and unsubstituted aromatic 5 or 6 membered monocyclic groups, 9 or 10 membered bicyclic groups, and 11 to 14 membered tricyclic groups provided that said monocyclic group or at least one of said bicyclic or tricyclic groups contains one or two oxygen or sulfur atoms and/or from one to nitrogen atoms provided that the total number of heteroatoms in each ring is four or less, the fused rings completing said bicyclic and tricyclic groups may contain only carbon atoms and may be saturated, partially saturated, or unsaturated, said nitrogen and sulfur atoms may be oxidized and said nitrogen atom may be quaternized, said heteroaryl group is attached at any available nitrogen or carbon atom of any ring, and said heteroaryl group may have one, two, or three substituents selected from the group consisting of halo, formyl, amino, cyano, alkyl, substituted alkyl, —NH(alkyl), —NH (cycloalkyl), —NH(substituted cycloalkyl), —NH (substituted alkyl), —NH(heterocycloalkyl), —N(alkyl)₂, alkoxy, alkylthio, cycloalkyl, substituted cycloalkyl, hydroxy, nitro, phenyl, phenylalkyl, substituted phenyl, substituted phenyl-alkyl, phenyloxy, phenylthio, carboxy, —CO₂-alkyl, —C(O)—NH₂, —C(O)—NH(alkyl), —C(O)—NH(cycloalkyl), —C(O)-alkyl, —O—C(O)-alkyl, —CO₂-aryl, —CO₂-(substituted aryl), —CH=N-hydroxy, —CH=N—O-alkyl, —CH=N—NH₂, —CH=N—NH(alkyl), —CH=N—N(alkyl)₂, —C(O)—NH(substituted alkyl), —C(O)-heterocyclo, —C(O)-aryl,

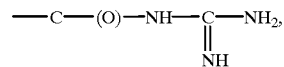

—C(O)—NH(heterocyclo),

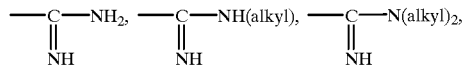

—C(O)—NH—OH, —C(O)—NH—O-alkyl, —C(O)—NH—NH₂, —C(O)—NH—NH(alkyl), —C(O)—NH—N (alkyl)₂, —C(O)—NH-(heterocycloalkyl), —CH₂—C(O)—NH—OH, —CH₂—C(O) —NH—O-alkyl, —CH₂—C(O)—NH—(substituted alkyl), —C(O)—NH—SO₂-alkyl, heterocyclo, heterocycloalkyl, heteroaryl, and heteroarylalkyl;

the term "substituted phenyl" and "substituted phenylalkyl" refer to a phenyl ring having one, two or three substituents selected from the group consisting of lower alkyl, lower alkoxy, lower alkylthio, halo, cyano, hydroxy, substituted lower alkyl, nitro, amino, —NH (lower alkyl), —NH(cycloalkyl), and —N(lower alkyl)₂, and/or one substituent selected from the group consisting of phenyl, benzyl, phenylethyl, phenyloxy, phenylthio, carboxy, —CO₂-lower alkyl, —C(O)—NH₂, —C(O)—NH(lower alkyl), —C(O)—NH(cycloalkyl), —C(O)—N(lower alkyl)₂, —C(O)-(lower alkyl), —O—C—(O)-(lower alkyl), —NH—CH₂-carboxy, —NH—CH₂—CO₂-lower alkyl, and —(CH₂)ₘ-heteroaryl, and pentafluorophenyl;

the term "substituted imidazole" refers to an imidazole, an aryl-fused imidazole, or a heteroaryl-fused imidazole having one or two substituents selected from the group consisting of alkyl, substituted alkyl, alkoxy, alkylthio, cycloalkyl, substituted cycloalkyl, halo, formyl, hydroxy, nitro, cyano, amino, —NH(alkyl), —NH (cycloalkyl), —NH(heterocycloalkyl), —NH (substituted cycloalkyl), —NH(substituted alkyl), —N(alkyl)₂, carboxy, —CO₂-alkyl, —C(O)—NH₂, —C(O)—NH(alkyl), —C(O)—NH(cycloalkyl), —C(O)—N(alkyl)₂, —C(O)-alkyl, —C(O)-aryl, —C(O)-substituted aryl, —O—C(O)-alkyl, phenyl, substituted phenyl, phenylalkyl, (substituted phenyl)-alkyl, —CH=N—OH, —CH=N—O-alkyl, —CH=N—NH₂, —CH=N—NH(alkyl), —CH=N—N(alkyl)₂, —C(O)—NH(substituted alkyl), —C(O)—(CH₂)ₘ-heteroaryl, —C(O)—(CH₂)ₘ-heterocyclo, CH₂—C(O)—NH (alkyl), —CO₂-aryl, —CO₂-substituted aryl,

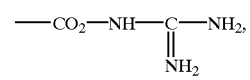

—C(O)—NH-heterocyclo,

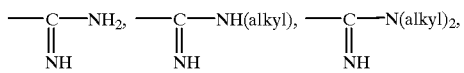

—C(O)—NH—OH, —C(O)—NH—O-alkyl, —C(O)—NH—NH$_2$, —C(O)—NH—NH(alkyl), —C(O)—NH—N(alkyl)$_2$, —C(O)—NH(heterocycloalkyl), —CH$_2$—C(O)—NH—OH, —CH$_2$—C(O)—NH—O-alkyl, —CH$_2$—C(O)—NH(substituted alkyl), —C(O)—NH—SO$_2$-alkyl, phenyloxy, phenylthio, heterocyclo, heterocycloalkyl, heteroaryl, and heteroarylalkyl;

the term "substituted pyrazole" refers to a pyrazole, an aryl-fused pyrazole, or a heteroaryl-fused pyrazole having one or two substituents selected from the group consisting of alkyl, substituted alkyl, alkoxy, alkylthio, halo, hydroxy, nitro, cyano, amino, —NH(alkyl), —N(alkyl)$_2$, —NH(cycloalkyl), carboxy, —CO$_2$-alkyl, —C(O)—NH$_2$, —C(O)—NH(alkyl), —C(O)—NH(cycloalkyl), —C(O)—N(alkyl)$_2$, —C(O)-alkyl, —O—C(O)-alkyl, —NH—CH$_2$-carboxy, —NH—CH$_2$—CO$_2$-alkyl, phenyl, benzyl, phenylethyl, phenyloxy, phenylthio, heterocyclo, heterocycloalkyl, heteroaryl, and heteroarylalkyl;

the term "substituted triazole" refers to a triazole having one substituent selected from the group consisting of alkyl, substituted alkyl, alkylthio, halo, hydroxy, nitro, cyano, amino, —NH(alkyl), —NH(cycloalkyl), —N(alkyl)$_2$, carboxy, —CO$_2$-alkyl, —C(O)—NH$_2$, —C(O)—NH(alkyl), —C(O)—NH(cycloalkyl), —C(O)—N(alkyl)$_2$, —C(O)-alkyl, —O—C(O)-alkyl, —NH—CH$_2$-carboxy, —NH—CH$_2$—CO$_2$-alkyl, phenyl, benzyl, phenylethyl, phenyloxy, phenylthio, heterocyclo, heterocycloalkyl, heteroaryl, and heteroarylalkyl; and m is zero or an integer from 1 to 4.

2. A compound of claim 1 or a pharmaceutically acceptable salt thereof wherein:

Y is nitrogen or —C(R$_5$)—;

Z is nitrogen or —C(R$_6$)— provided that at least one of Y and Z is nitrogen;

R$_1$ and R$_2$ are independently selected from the group consisting of —NR$_8$R$_9$, hydrogen, and chloro with the proviso that at least one of R$_1$ or R$_2$ is —NR$_8$R$_9$;

R$_3$ is hydrogen, alkyl, substituted alkyl, —(CH$_2$)$_n$-phenyl, or —(CH$_2$)$_n$-substituted phenyl;

R$_4$ is hydrogen, halogen, substituted alkyl, —OR$_{10}$ or —NR$_{11}$R$_{12}$;

R$_5$ and R$_6$ are independently selected from the group consisting of hydrogen, halogen, alkyl, and substituted alkyl;

R$_8$ and R$_9$ are independently selected from the group consisting of hydrogen, alkyl, substituted alkyl, —(CH$_2$)$_m$-cycloalkyl, —(CH$_2$)$_m$-substituted cycloalkyl, —(CH$_2$)$_m$-phenyl, —(CH$_2$)$_m$-substituted phenyl, —(CH$_2$)$_m$-heterocyclo, and —(CH$_2$)$_m$-heteroaryl or R$_8$ and R$_9$ taken together with the N atom to which they are attached can form a heterocyclo ring, a substituted or unsubstituted imidazole, a substituted or unsubstituted pyrazole, or a substituted or unsubstituted triazole;

R$_{10}$, R$_{11}$ and R$_{12}$ are independently selected from the group consisting of hydrogen, alkyl, —(CH$_2$)$_m$-phenyl, —(CH$_2$)$_m$-substituted phenyl, and —(CH$_2$)$_m$-heteroaryl;

m is zero or an integer from 1 to 4;

n is an integer from 1 to 4;

the term "substituted alkyl" and "substituted lower alkyl" refer to such groups having one, two or three substituents selected from the group consisting of halo, —(CH$_2$)$_m$-hydroxy, cyano, lower alkoxy, lower alkylthio, amino, —NH(lower alkyl), —N(lower alkyl)$_2$, —C(O)—NH$_2$, —C(O)—NH(lower alkyl), —C(O)—N(lower alkyl)$_2$, carboxy, and —CO$_2$-lower alkyl;

the term "substituted cycloalkyl" refers to fully saturated rings of 3 to 7 carbon atoms having one, two or three substituents selected from the group consisting of lower alkyl, lower alkoxy, lower alkylthio, halo, —(CH$_2$)$_m$-hydroxy, cyano, amino, —NH(lower alkyl), —NH(cycloalkyl), —N(lower alkyl)$_2$, —C(O)—NH$_2$, —C(O)—NH(lower alkyl), carboxy, —CO$_2$-lower alkyl, —(CH$_2$)$_m$-phenyl, —(CH$_2$)$_m$-substituted phenyl, —(CH$_2$)$_m$-heteroaryl, keto, =N—OH, =N—O-lower alyl, —(CH$_2$)$_m$-heterocyclo, and a five or six membered ketal;

the term "substituted phenyl" refers to a phenyl ring having one, two or three substituents selected from the group consisting of lower alkyl, lower alkoxy, lower alkylthio, halo, cyano, hydroxy, substituted lower alkyl, nitro, amino, —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, —CO$_2$-lower alkyl, —C(O)—NH$_2$, —C(O)—NH(lower alkyl), —C(O)—NH(cycloalkyl), —C(O)—N(lower alkyl)$_2$, —C(O)-lower alkyl, —O—C—(O)-lower alkyl, —NH—CH$_2$-carboxy, —NH—CH$_2$—CO$_2$-lower alkyl, and —(CH$_2$)$_m$-heteroaryl, and pentafluorophenyl;

the term "heterocyclo" refers to substituted and unsubstituted saturated or partially saturated 3 to 7 membered monocyclic rings having one or two O or S atoms and/or one to four N atoms provided that the total number of heteroatoms is four or less and that the heterocyclo ring contains at least one carbon atom, said nitrogen and sulfur atoms may be oxidized and said nitrogen atoms may be quaternized, said heterocyclo ring is attached at any available nitrogen or carbon atom, and said heterocyclo ring may contain one, two or three substituents attached to an available carbon or nitrogen atom and selected from the group consisting of halo, hydroxy, cyano, lower alkyl, cycloalkyl, substituted lower alkyl, lower alkoxy, lower alkylthio, keto, formyl, nitro, amino, —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, substituted phenyl, substituted phenyl-CH$_2$—, substituted phenyl-CH$_2$—CH$_2$—, —CO$_2$-lower alkyl, —C(O)—NH$_2$, —C(O)—NH(lower alkyl), —C(O)—NH(cycloalkyl), —C(O)-heteroaryl, —C(O)—N(lower alkyl)$_2$, —NH—CO$_2$-(lower alkyl), —C(O)-lower alkyl, —O—C(O)-(lower alkyl), —NH—CH$_2$-carboxy, —NH—CH$_2$—CO$_2$-lower alkyl, —(CH$_2$)$_m$-heterocyclo, —(CH$_2$)$_m$-heteroaryl, =N—OH, =N—O-lower alkyl, and a five or six membered ketal;

the term "heteroaryl" refers to 5 or 6 membered substituted or unsubstituted monocyclic aromatic rings and 9 or 10 membered substituted or unsubstituted bicyclic rings wherein at least one of said nitrogen rings is aromatic, provided that said monocyclic ring and at least one of said bicyclic rings have one or two O or S atoms and/or one to four N atoms provided that the total number of heteroatoms is four or less, said nitrogen and sulfur atoms may be oxidized and said nitrogen atom may be quaternized, said heteroaryl substituent is attached to an available carbom atom and is one, two or three substituents selected from the group consisting of halo, cyano, lower alkyl, cycloalkyl, substituted lower alkyl, lower alkoxy, lower alkylthio, hydroxy, nitro, formyl, amino, —NH(lower alkyl), —NH(cycloalkyl), and —N(lower alkyl)$_2$, and/or one substituent selected from the group consisting of phenyl, benzyl, phenylethyl, phenyloxy, phenylthio, carboxy, substituted phenyl, substituted phenyl-CH$_2$—, substituted phenyl-CH$_2$—CH$_2$, —CO$_2$-lower alkyl, —C(O)—NH$_2$, —C(O)—NH(lower alkyl), —C(O)—NH(cycloalkyl), —C(O)—N(lower alkyl)$_2$, —C(O)-lower alkyl, —O—C(O)-lower alkyl, —NH—CH$_2$-carboxy, —NH—CH$_2$—CO$_2$-lower alkyl, —(CH$_2$)$_m$-heterocyclo, and —(CH$_2$)$_m$-heteroaryl;

the term "substituted imidazole" refers to an imidazole, an aryl-fused imidazole or a heteroaryl-fused imidazole having one or two substituents selected from the group consisting of lower alkyl, cycloalkyl, substituted lower alkyl, lower alkoxy, lower alkylthio, nitro, halo, cyano, formyl, amino, —NH(lower alkyl), —NH(cycloalkyl), —NH(substituted lower alkyl), and —N(lower alkyl)$_2$, and/or one substituent selected from the group consisting of phenyl, benzyl, phenylethyl, substituted phenyl, substituted phenyl-CH$_2$—, substituted phenyl-CH$_2$—CH$_2$—, phenyloxy, phenylthio, carboxy, —CO$_2$-lower alkyl, —C(O)—NH$_2$, —CH=N—OH, —CH=N—O-lower alkyl, —C(O)—NH(lower alkyl), —C(O)—NH(cycloalkyl), —C(O)—N(lower alkyl)$_2$, —C(O)-lower alkyl, —O—C(O)-lower alkyl, —CH=N—NH$_2$, —CH=N—NH(lower alkyl), —CH=N—N(lower alkyl)$_2$, —C(O)—NH(substituted lower alkyl), —C(O)—(CH$_2$)$_m$-heterocyclo, —CO$_2$-phenyl, —CO$_2$-substituted phenyl,

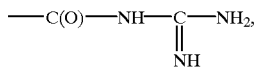

—C(O)—NH—(CH$_2$)$_m$-heterocyclo, —C(O)—(CH$_2$)$_m$-heteroaryl,

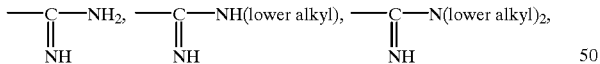

—C(O)—NH—OH, —C(O)—NH—O-lower alkyl, —C(O)—NH—NH$_2$, —C(O)—NH—NH(lower alkyl), —C(O)—NH—N(lower alkyl)$_2$,

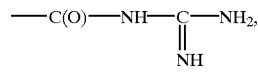

—C(O)—NH—SO$_2$-(lower alkyl), —CH$_2$—C(O)—NH—OH, —CH$_2$—C(O)—NH(substituted lower alkyl), —NH—CH$_2$-carboxy, —NH—CH$_2$—CO$_2$-lower alkyl, —(CH$_2$)$_m$-heterocyclo, and —(CH$_2$)-heteroaryl;

the term "substituted pyrazole" refers to a pyrazole, an aryl-fused pyrazole, or a heteroaryl-fused pyrazole having one or two substituents selected from the group consisting of lower alkyl, substituted lower alkyl, lower alkoxy, lower alkylthio, nitro, hydroxy, halo, cyano, amino, —NH(lower alkyl), —NH(cycloalkyl), and —N(lower alkyl)$_2$, and/or one substituent selected from the group consisting of phenyl, benzyl, substituted phenyl, substituted phenyl-CH$_2$—, substituted phenyl-CH$_2$—CH$_2$—, phenylethyl, phenyloxy, phenylthio, carboxy, —CO$_2$-lower alkyl, —C(O)—NH$_2$, —C(O)—NH(lower alkyl), —C(O)—NH(cycloalkyl), —C(O)—N(lower alkyl)$_2$, —C(O)-lower alkyl, —O—C(O)-lower alkyl, —NH—CH$_2$-carboxy, —NH—CH$_2$—CO$_2$-lower alkyl, —(CH$_2$)$_m$-heteroaryl, and —(CH$_2$)$_m$-heteroaryl; and the term "substituted triazole" refers to a triazole having one substituent selected from the group consisting of lower alkyl, substituted lower alkyl, lower alkoxy, lower alkylthio, hydroxy, halo, cyano, amino, —NH(lower alkyl), —NH(cycloalkyl), —N(lower alkyl)$_2$, phenyl, benzyl, phenylethyl, substituted phenyl, substituted phenyl-CH$_2$—, substituted phenyl-CH$_2$—CH$_2$—, phenyloxy, phenylthio, carboxy, —CO$_2$-lower alkyl, —C(O)—NH$_2$, —C(O)—NH(lower alkyl), —C(O)—NH(cycloalkyl), —C(O)—N-(lower alkyl)$_2$, —C(O)-lower alkyl, —O—C(O)-lower alkyl, —NH—CH$_2$-carboxy, —NH—CH$_2$—CO$_2$-lower alkyl, —(CH$_2$)$_m$-heterocyclo, and —(CH$_2$)$_m$-heteroaryl.

3. A compound of claim 2 or a pharmaceutically acceptable salt thereof wherein:

Y is nitrogen;

Z is —C(R$_6$)—;

R$_1$ and R$_2$ are independently selected from the group consisting of —R$_8$R$_9$, hydrogen and chloro with the proviso that at least one of R$_1$ or R$_2$ is —NR$_8$R$_9$;

R$_3$ is hydrogen, lower alkyl, —(CH$_2$)$_n$-phenyl, or —(CH$_2$)$_n$-substituted phenyl;

R$_4$ is hydrogen;

R$_6$ is hydrogen;

R$_8$ and R$_9$ are independently selected from the group consisting of hydrogen, lower alkyl, substituted lower alkyl, —(CH$_2$)$_m$-cyclohexyl, —(CH$_2$)$_m$-substituted cyclohexyl, —(CH$_2$)$_m$-phenyl, —(CH$_2$)$_m$-substituted phenyl, —(CH$_2$)$_m$-heterocyclo, and —(CH$_2$)$_m$-heteroaryl or R$_8$ and R$_9$ taken together with the N atom to which they are attached can form a heterocyclo ring or a substituted or unsubstituted imidazole;

m is zero or an integer from 1 to 4;

n is an integer from 1 to 4;

the term "substituted lower alkyl" refers to such groups having one substituent selected from the group consisting of halo, —(CH$_2$)$_m$-hydroxy, lower alkoxy, amino, —NH(lower alkyl), —NH(cycloalkyl of 3 to 6 carbons), —N(lower alkyl)$_2$, carboxy, —CO$_2$-lower alkyl, —C(O)—NH$_2$, —C(O)—NH(lower alkyl), and —C(O)—N(lower alkyl)$_2$;

the term "substituted phenyl" refers to a phenyl ring having one, two, or three substituents selected from the group consisting of halo, cyano, lower alkyl, lower alkoxy, —(CH$_2$)m-hydroxy, trifluoromethyl, amino, —NH(lower alkyl), —NH(cycloalkyl of 3 to 6 carbons), and —N(lower alkyl)$_2$, and/or one substituent selected from the group consisting of carboxy, —CO$_2$-lower alkyl, —C(O)—NH$_2$, —C(O)—NH(lower alkyl), —C(O)—NH(cycloalkyl of 3 to 6 carbons), —C(O)—N(lower alkyl)$_2$, —C(O)-lower alkyl, and —O—C(O)-lower alkyl, and pentafluorophenyl;

the term "heterocyclo" refers to 3 to 7 membered substituted or unsubstituted monocyclic saturated or partially saturated rings having one or two O or S atoms and/or one to four N atoms provided that the total number of heteroatoms in the ring is four or less and that the ring contains at least one carbon atom, said nitrogen and sulfur atoms may be oxidized and the nitrogen atom may be quaternized, said heterocyclo substituents are attached to an available carbon or nitrogen atom and are one or two members selected from the group consisting of halo, keto, hydroxy, cyano, lower alkyl, substituted lower alkyl, cycloalkyl of 3 to 6 carbons, lower alkoxy, trifluoromethyl, amino, —NH (lower alkyl), —NH(cycloalkyl of 3 to 6 carbons) and —N(lower alkyl) $_2$, and/or one member selected from the group consisting of carboxy, —CO$_2$-lower alkyl, —C(O)—NH$_2$, —C(O)—NH(lower alkyl), —C(O)—NH(cycloalkyl of 3 to 6 carbons), —C(O)—N(lower alkyl)$_2$, —C(O)-lower alkyl, —O—C(O)-lower alkyl, tetrazolyl,

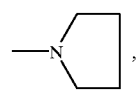

=N—OH, =N—O-lower alkyl, —NH—CH$_2$—CO$_2$-lower alkyl, 1,3-dioxolane, 1,3-dioxolane fused to a phenyl ring, 1,3-dioxane, and 1,3-dioxane fused to a phenyl ring;

the term "heteroaryl" refers to 5 or 6 membered substituted or unsubstituted monocyclic aromatic rings and 9 or 10 membered substituted or unsubstituted bicyclic rings wherein at least one of said rings is aromatic, provided that said monocyclic ring and at least one of said bicyclic rings has one or two O or S atoms and/or one to four N atoms provided that the total number of heteroatoms in the ring is four or less, said nitrogen and sulfur atoms may be oxidized and said nitrogen atom may be quaternized, said heteroaryl substituents are attached to an available carbon or nitrogen atom and are one or two members selected from the group consisting of halo, hydroxy, cyano, lower alkyl, substituted lower alkyl, cycloalkyl of 3 to 6 carbons, lower alkoxy, trifluoromethyl, amino, —NH (lower alkyl), —N(lower alkyl)$_2$, and —NH(cycloalkyl of 3 to 6 carbons), and/or one substituent selected from the group consisting of carboxy, —CO$_2$-lower alkyl, —C(O)—NH$_2$, —C(O)—NH(lower alkyl), —C(O)—NH(cycloalkyl of 3 to 6 carbons), —C(O)—N(lower alkyl)$_2$, —C(O)-lower alkyl, and —O—C(O)-lower alkyl;

the term "substituted cyclohexyl", refers to a cyclohexyl ring have one or two substituents selected from the group consisting of lower alkyl, lower alkoxy, lower alkylthio, halo, keto, —(CH$_2$)$_m$-hydroxy, cyano, amino, —NH(lower alkyl) and —N(lower alkyl)$_2$ and/or one substituent selected from the group consisting of carboxy, —CO$_2$-lower alkyl, =N—OH, =N—O-lower alkyl, 1,3-dioxolane, 1,3-dioxane, —C(O)—NH$_2$, —C(O)—NH(lower alkyl), and —C(O)—N(lower alkyl)$_2$;

the term "substituted imidazole" refers to an imidazole having one or two substituents selected from the group consisting of lower alkyl, substituted lower alkyl, lower alkoxy, halo, —(CH$_2$)$_m$-hydroxy, cyano, formyl, trifluoromethyl, amino, —NH(lower alkyl), N-(lower alkyl)$_2$, and —NH(cycloalkyl of 3 to 6 carbons), and/or one substituent selected from the group consisting of carboxy, —CO$_2$-lower alkyl,

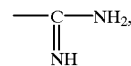

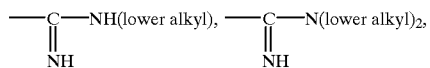

—CO$_2$-phenyl, —CO$_2$-(substituted phenyl,

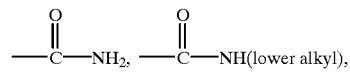

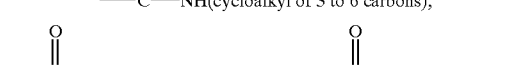

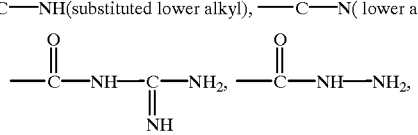

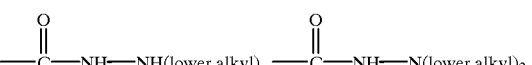

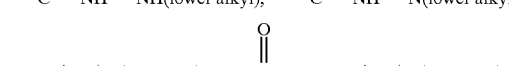

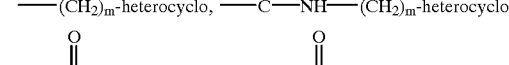

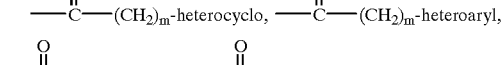

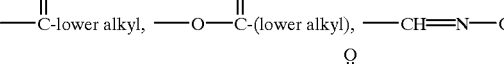

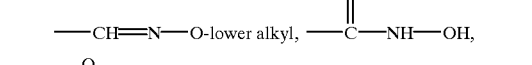

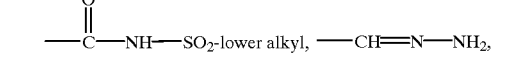

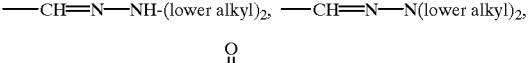

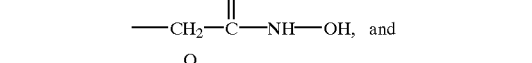

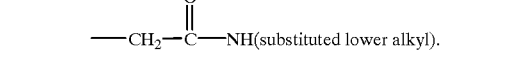

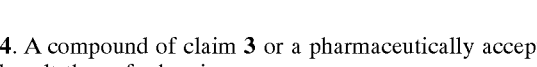

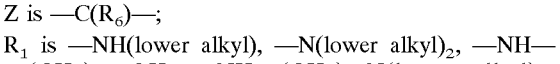

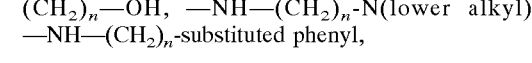

4. A compound of claim 3 or a pharmaceutically acceptable salt thereof wherein:

Y is nitrogen;

Z is —C(R$_6$)—;

R$_1$ is —NH(lower alkyl), —N(lower alkyl)$_2$, —NH—(CH$_2$)$_n$—OH, —NH—(CH$_2$)$_n$-N(lower alkyl)$_2$, —NH—(CH$_2$)$_n$-substituted phenyl,

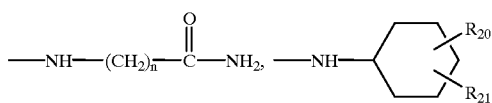

-continued

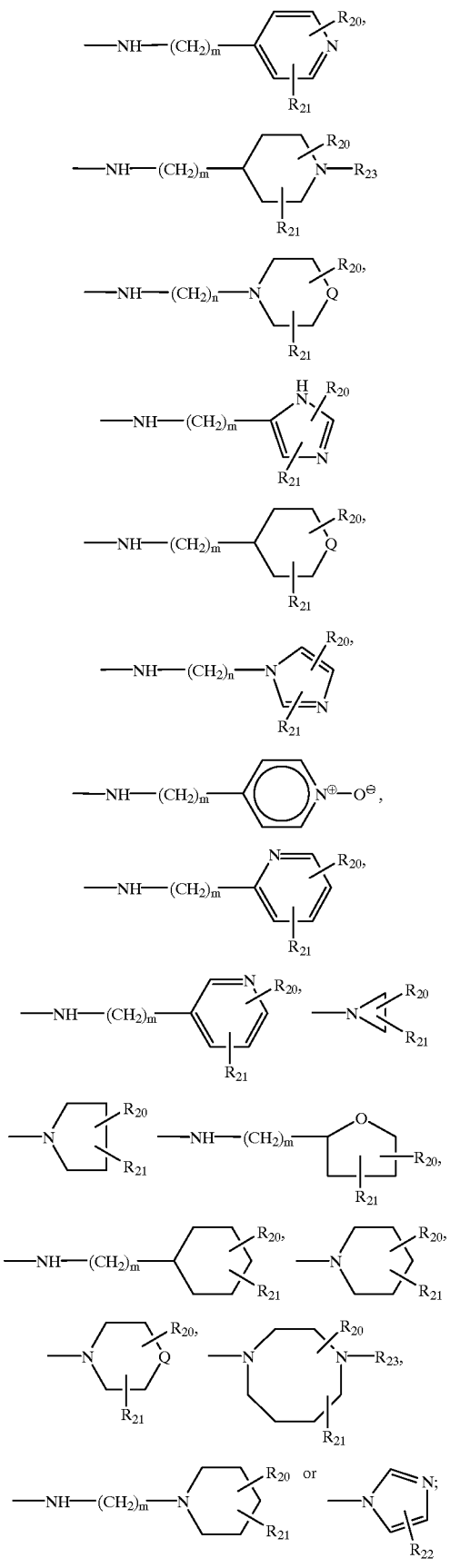

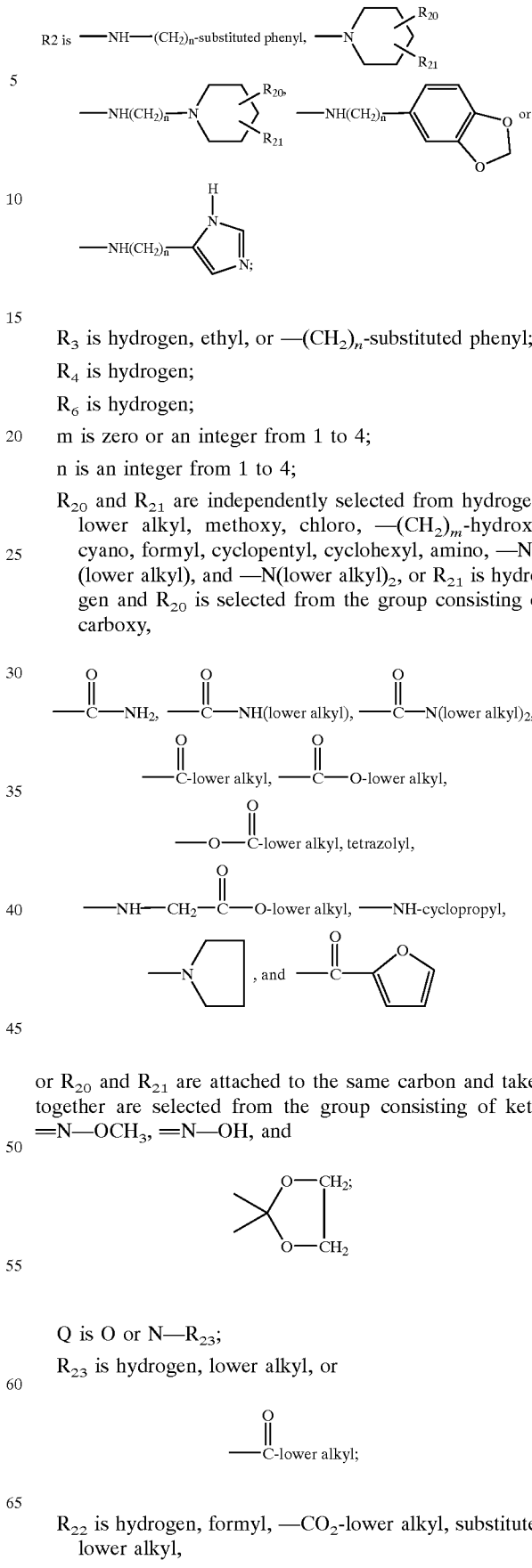

R$_3$ is hydrogen, ethyl, or —(CH$_2$)$_n$-substituted phenyl;

R$_4$ is hydrogen;

R$_6$ is hydrogen;

m is zero or an integer from 1 to 4;

n is an integer from 1 to 4;

R$_{20}$ and R$_{21}$ are independently selected from hydrogen, lower alkyl, methoxy, chloro, —(CH$_2$)$_m$-hydroxy, cyano, formyl, cyclopentyl, cyclohexyl, amino, —NH(lower alkyl), and —N(lower alkyl)$_2$, or R$_{21}$ is hydrogen and R$_{20}$ is selected from the group consisting of carboxy, or R$_{20}$ and R$_{21}$ are attached to the same carbon and taken together are selected from the group consisting of keto, =N—OCH$_3$, =N—OH, and Q is O or N—R$_{23}$;

R$_{23}$ is hydrogen, lower alkyl, or

R$_{22}$ is hydrogen, formyl, —CO$_2$-lower alkyl, substituted lower alkyl,

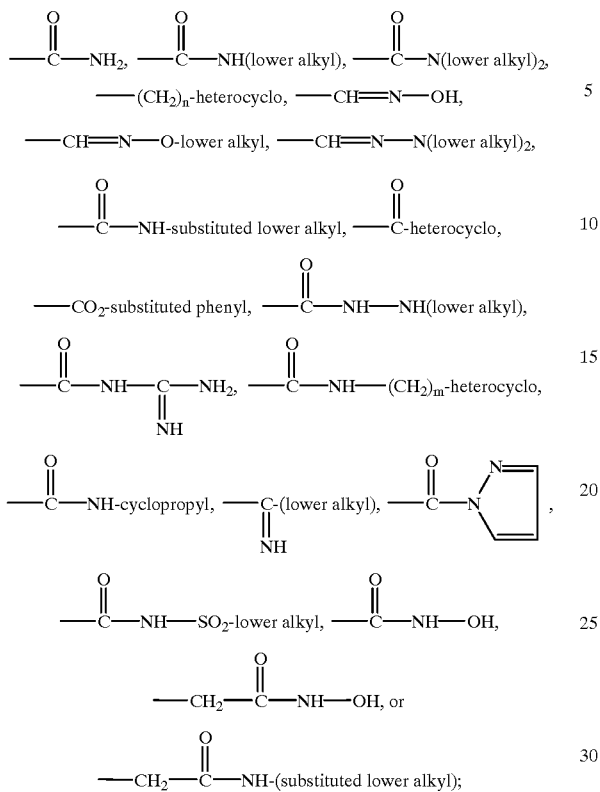

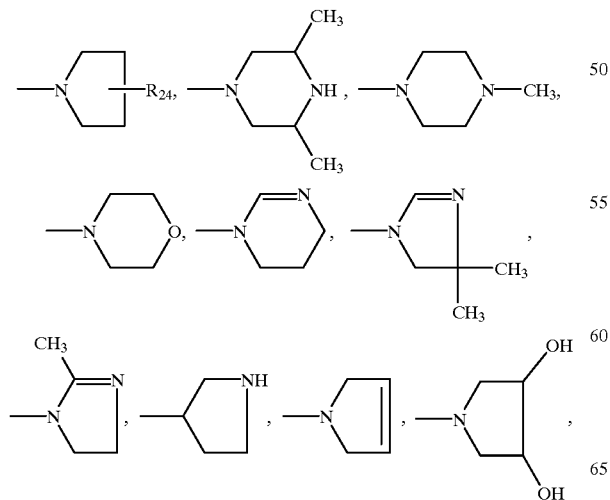

the term "substituted lower alkyl" refers to such groups having a substituent selected from the group consisting of hydroxy, carboxy, amino, —NH(lower alkyl), —N(lower alkyl)$_2$, —CO$_2$-lower alkyl, —C(O)—NH$_2$, —C(O)NH$_2$, —C(O)—NH(lower alkyl), and —C(O)—N(lower alkyl)$_2$;

the term "substituted phenyl" refers to a phenyl ring having one or two substituents selected from the group consisting of methoxy, chloro, and fluoro, and pentafluorophenyl;

the term heterocyclo refers to the following

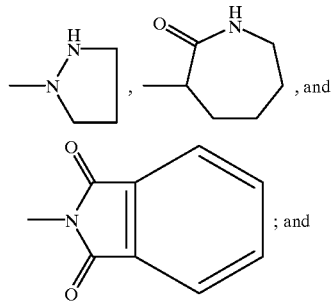
, and $R_{24}$ is hydrogen, amino, —NH—CO$_2$-lower alkyl, —N(lower alkyl)$_2$, —NH(lower alkyl), methoxymethyl, hydroxy, hydroxymethyl, or

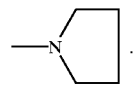

5. A compound of claim 4 or a pharmaceutically acceptable salt thereof of the formula:

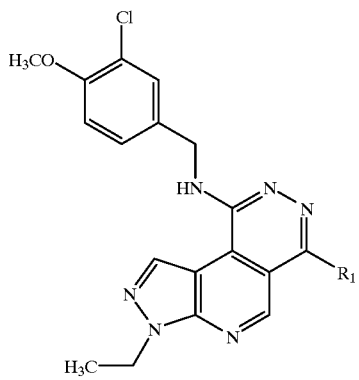

wherein:

$R_1$ is

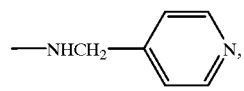

—NH(CH$_2$)$_3$—OH,

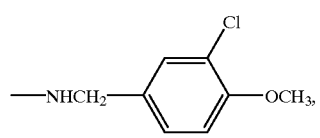

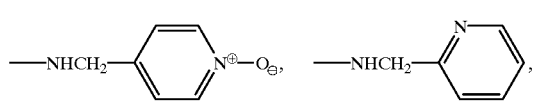

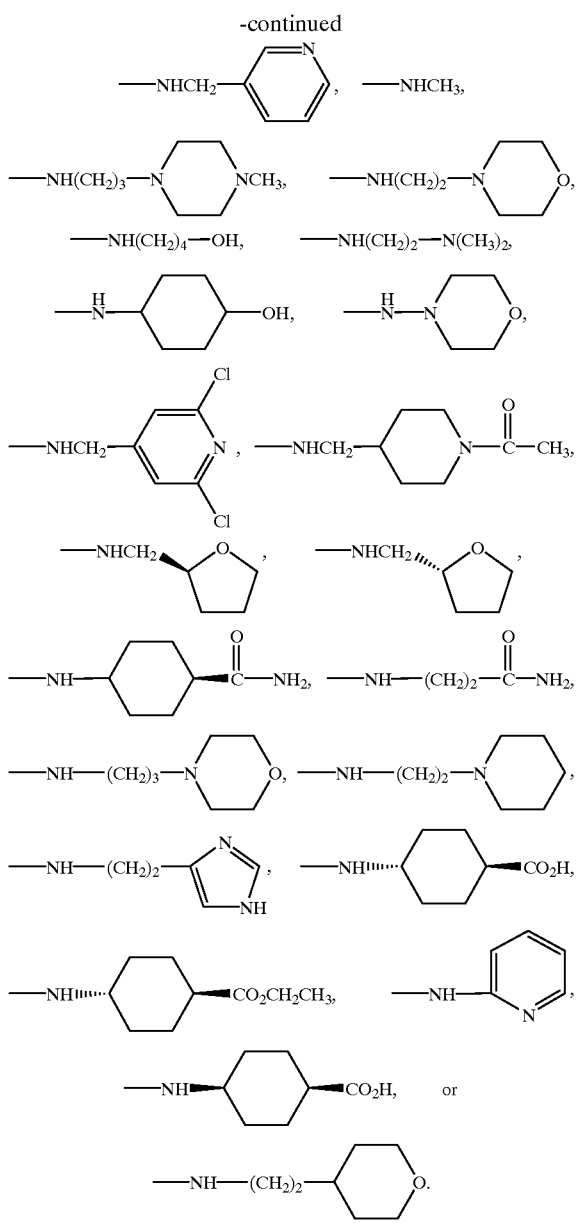
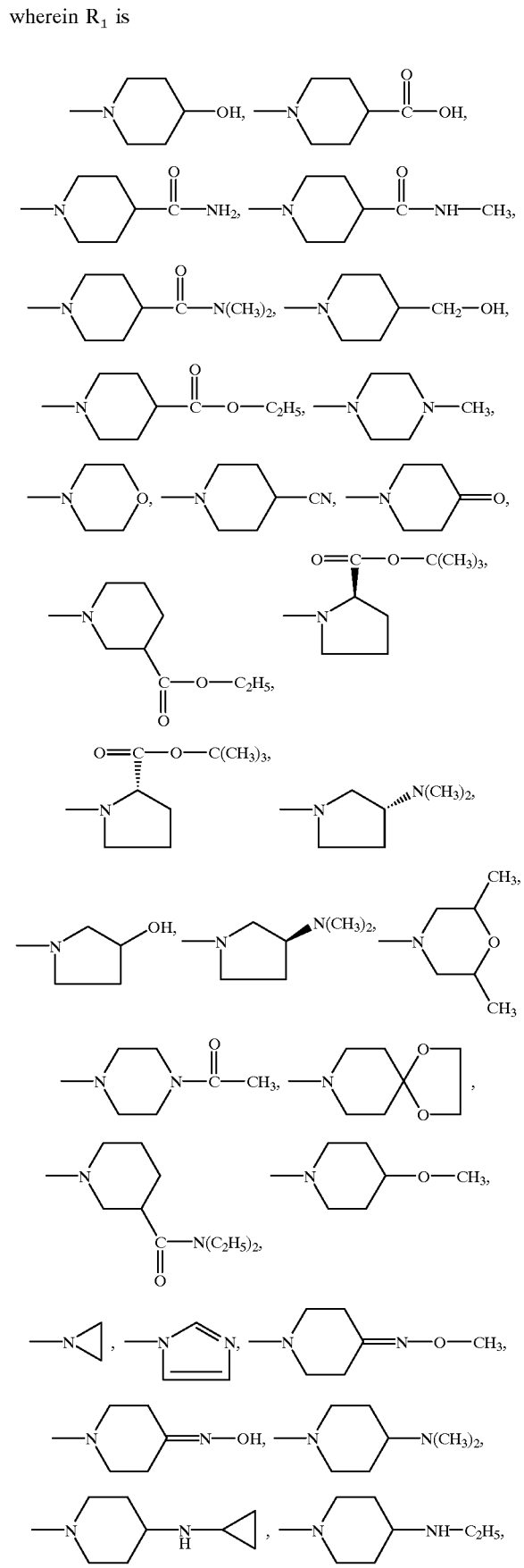
6. A compound of claim 4 or a pharmaceutically acceptable salt thereof of the formula
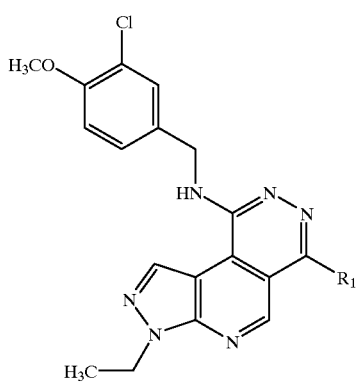
wherein $R_1$ is

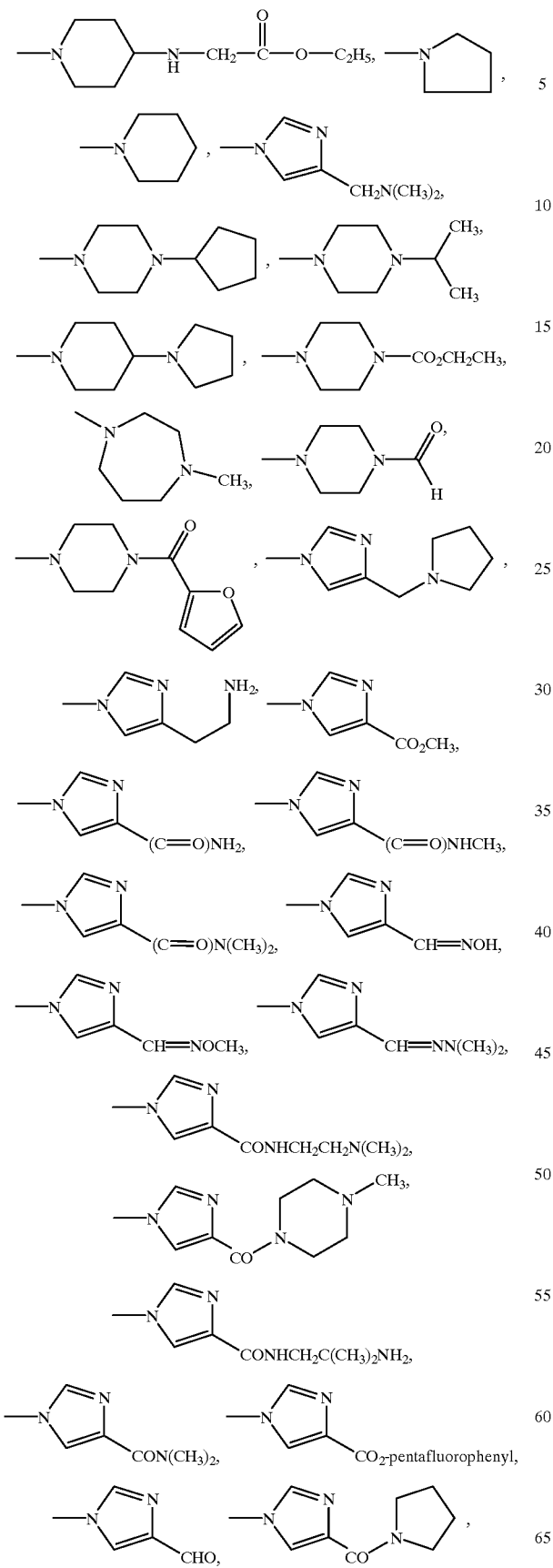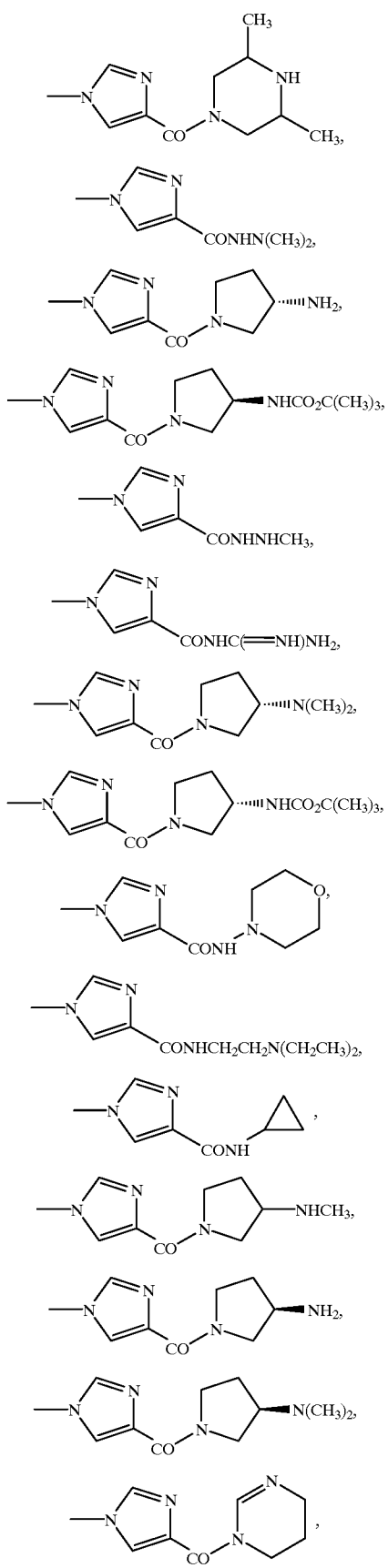

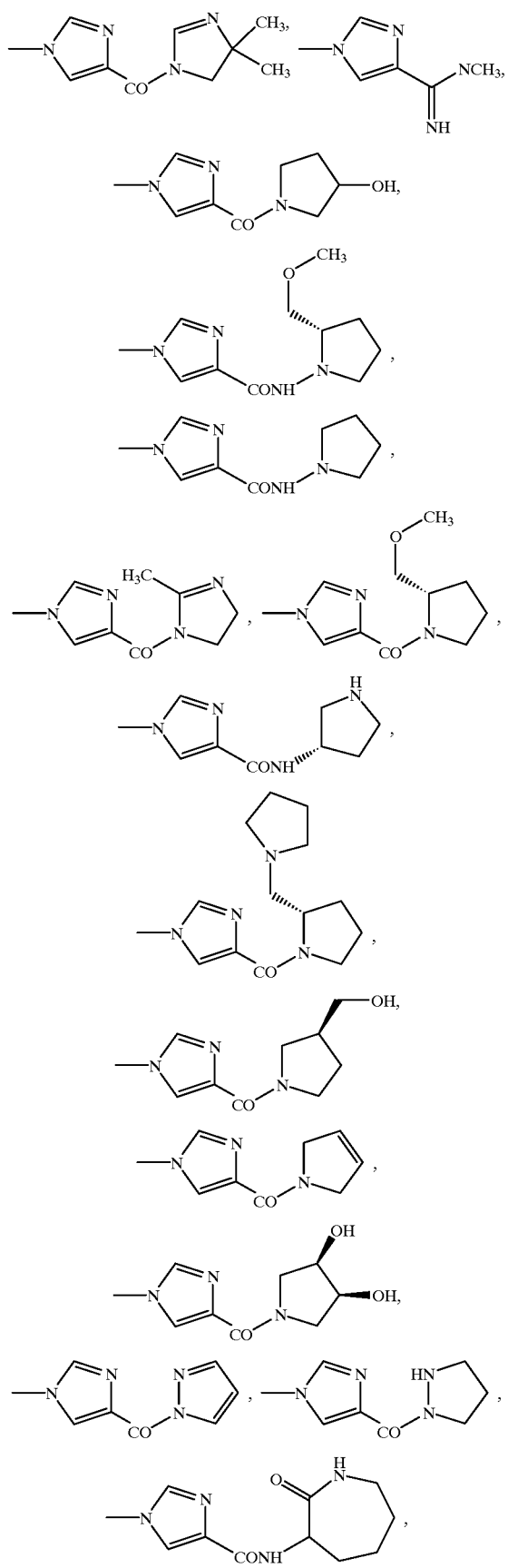
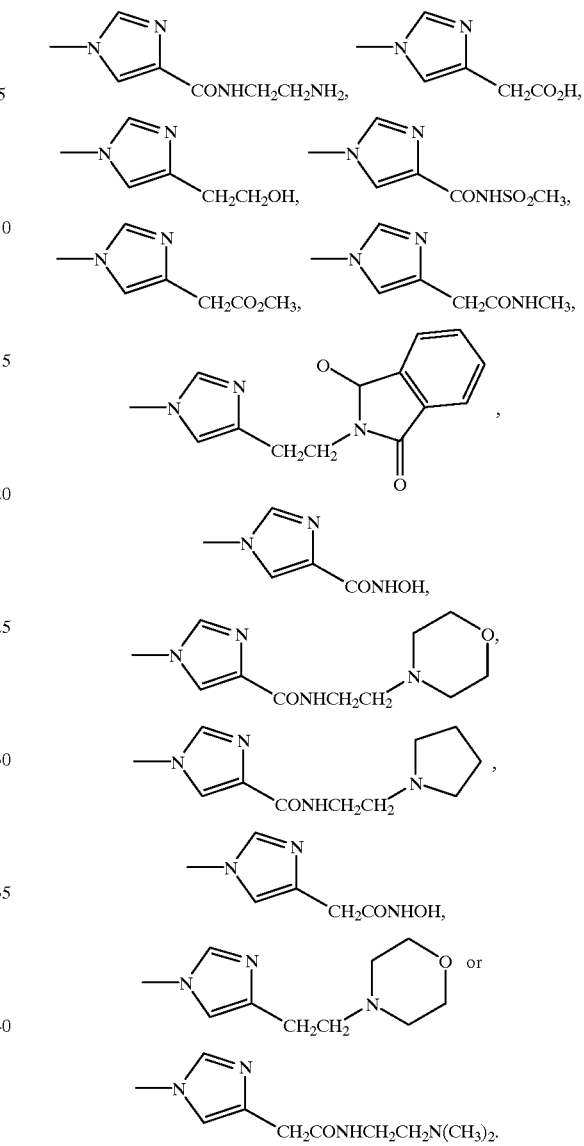
7. A compound of claim 4 or a pharmaceutically acceptable salt thereof of the formula
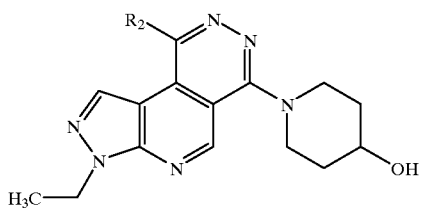
wherein
R₂ is —NHCH₂—⟨⟩—OCH₃, —NHCH₂—⟨⟩—F, -continued

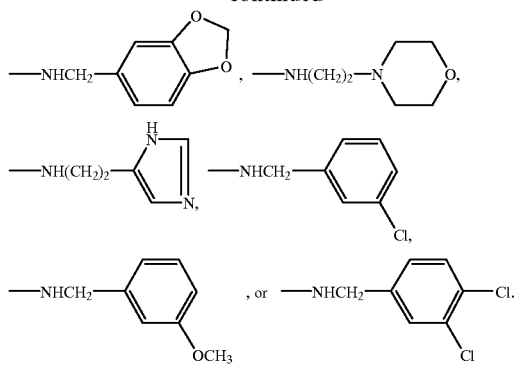

8. The compound of claim 4:
1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide;
1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide, methanesulfonate (1:1);
$N^9$-[(3-chloro-4-methoxyphenyl)methyl]-3-ethyl-$N$-$^6$-(4-pyridinylmethyl)-3H-pyrazolo[4',3':5,6]pyrido[3,4-d]pyridazine-6,9-diamine;
1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-methanol;
1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-(N,N-dimethylethylene)carboxamide;
1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-(N-methylpiperidinyl)carboxamide;
1-[9-[[(3-chloro-4-methoxyphenyl)methyl]amino]-3-ethyl-3H-pyrazolo[4',3':5,6]pyrido[3,4-d]pyridazin-6-yl]-N-1H-imidazole-4-pyrrolidinyl carboxamide;
1-[9-[[(3-chloro-4-methoxyphenyl)methyl]amino]-3-ethyl-3H-pyrazolo[4',3':5,6]pyrido[3,4-d]pyridazin-6-yl]-1H-imidazole-4-[R-1-amino-2-(methoxymethyl)pyrrolidinyl]hydrazide; or
1-[9-[[(3-chloro-4-methoxyphenyl)methyl]amino]-3-ethyl-3H-pyrazolo[4',3':5,6]pyrido[3,4-d]pyridazin-6-yl]-1H-imidazole-4-acetic acid.

9. The compound of claim 8:
1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide.

10. The compound of claim 8:
1-[9-[[(3-chloro-4-methoxyphenyl)methyl]amino]-3-ethyl-3H-pyrazolo[4',3':5,6]pyrido[3,4-d]pyridazin-6-yl]-N-methyl-1H-imidazole-4-carboxamide, methansulfonate (1:1).

11. A pharmaceutical composition comprising one or more compounds of claim 1 or a pharmaceutically acceptable salt thereof and a pharmaceutically acceptable carrier.

12. A method of treating a cGMP-associated condition comprising administering to a mammal in need thereof an effective amount of a composition of claim 11.

13. A method of treating sexual dysfunction in a male or female mammal comprising administering an effective amount of a composition of claim 11.

14. A method of treating erectile dysfunction comprising administering to a mammal in need thereof an effective amount of a composition of claim 11.

15. A compound of the formula

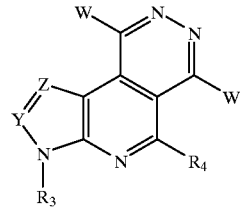

wherein:

W is chloro, bromo, or iodo;

Y is nitrogen or —C($R_5$)—;

Z is nitrogen or —C($R_6$)— provided that at least one of Y and Z is nitrogen; and $R_3$, $R_4$, $R_5$ and $R_6$ are as defined in claim 1.

16. A compound of claim 15 wherein:

W is chloro.

17. A compound of the formula

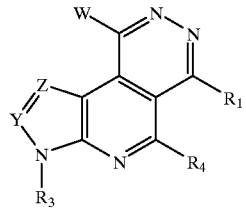

wherein:

W is chloro, bromo, or iodo;

Y is nitrogen or —C($R_5$)—;

Z is nitrogen or —C($R_6$)— provided that at least one of Y and Z is nitrogen;

$R_1$ is —$SR_7$, —$OR_7$, —$NR_8R_9$, or

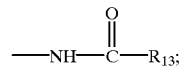

and $R_3$, $R_4$, $R_5$, $R_6$, $R_7$, $R_8$, $R_9$ and $R_{13}$ are as defined in claim 1.

18. A compound of claim 17 wherein:

W is chloro.

19. A process for preparing a compound of claim 1 which comprises: the sequential addition of an amine, thiol or alcohol of the formulas $R_1H$: and $R_2H$ to the compound of the formula

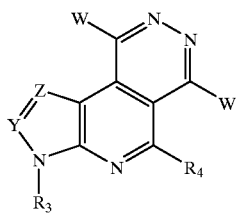

wherein Y, Z, R$_3$ and R$_4$ are as defined in claim 1 and W is chloro, bromo, or iodo; and said additions are performed in the presence of an inert solvent and a base.

20. A process of claim 19 wherein:

a) a compound of the formula

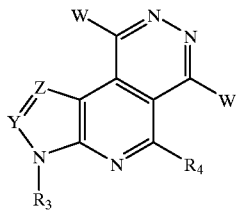

is reacted with an amine, thiol or alcohol of the formula R$_1$H in an inert solvent at a temperature of from about 0° C. to about 110° C. in the presence of a base selected from trialkylamines, 1,8-diazabicyclo undec-7-ene, and a carbonate to give the compound of the formula

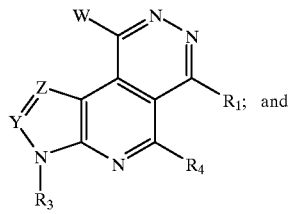

b) the product from step (a) is reacted with an amine, thiol or alcohol of the formula R$_2$H in an inert solvent under elevated temperature in the presence of a base selected from trialkylamines and 1,8-diazabicyclo undec-7-ene.

* * * * *

UNITED STATES PATENT AND TRADEMARK OFFICE
CERTIFICATE OF CORRECTION

PATENT NO.    : 6,316,438 B1                                              Page 1 of 1
DATED         : November 13, 2001
INVENTOR(S)   : Yu et al.

It is certified that error appears in the above-identified patent and that said Letters Patent is hereby corrected as shown below:

Column 149,
Line 60,

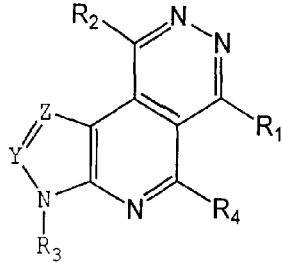 should read 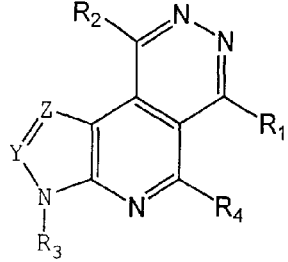

Column 152,
Line 5, —C(O) -substituted aryl, should be inserted after —C(O) -aryl, Signed and Sealed this Twenty-ninth Day of October, 2002

Attest:

JAMES E. ROGAN
Attesting Officer    Director of the United States Patent and Trademark Office